US010611747B2

(12) United States Patent
Teng et al.

(10) Patent No.: US 10,611,747 B2
(45) Date of Patent: Apr. 7, 2020

(54) PYRONE BASED COMPOUNDS FOR TREATING BACTERIAL INFECTIONS

(71) Applicant: FORGE THERAPEUTICS, INC., San Diego, CA (US)

(72) Inventors: Min Teng, San Diego, CA (US); Baskar Nammalwar, San Diego, CA (US); Konstantin Taganov, San Diego, CA (US); David T. Puerta, San Diego, CA (US)

(73) Assignee: FORGE THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 15/773,976

(22) PCT Filed: Nov. 9, 2016

(86) PCT No.: PCT/US2016/061198
§ 371 (c)(1),
(2) Date: May 4, 2018

(87) PCT Pub. No.: WO2017/083434
PCT Pub. Date: May 18, 2017

(65) Prior Publication Data
US 2018/0319761 A1 Nov. 8, 2018

Related U.S. Application Data

(60) Provisional application No. 62/252,795, filed on Nov. 9, 2015.

(51) Int. Cl.
C07D 309/40 (2006.01)
C07D 405/06 (2006.01)
C07D 405/12 (2006.01)
C07D 487/04 (2006.01)
C07D 498/08 (2006.01)
A61P 31/04 (2006.01)
C07D 491/08 (2006.01)

(52) U.S. Cl.
CPC ............ *C07D 309/40* (2013.01); *A61P 31/04* (2018.01); *C07D 405/06* (2013.01); *C07D 405/12* (2013.01); *C07D 487/04* (2013.01); *C07D 491/08* (2013.01); *C07D 498/08* (2013.01)

(58) Field of Classification Search
CPC .. C07D 309/40; C07D 405/06; C07D 405/12; C07D 487/04; C07D 491/08; C07D 498/08; A61P 31/04
See application file for complete search history.

(56) References Cited

U.S. PATENT DOCUMENTS

| | | | | |
|---|---|---|---|---|
| 5,543,534 A | * | 8/1996 | Vuligonda | C07C 17/10 549/421 |
| 7,579,486 B2 | * | 8/2009 | Puerta | A61K 31/167 549/418 |
| 7,786,316 B2 | * | 8/2010 | Puerta | A61K 31/167 546/290 |
| 9,145,381 B2 | * | 9/2015 | Fanelli | C07D 309/40 |
| 10,130,714 B2 | * | 11/2018 | Wong | A61K 31/351 |
| 2003/0181472 A1 | | 9/2003 | Clark et al. | |
| 2007/0117848 A1 | * | 5/2007 | Puerta | A61K 31/167 514/337 |
| 2007/0149556 A1 | | 6/2007 | Mikamiyama et al. | |
| 2012/0035255 A1 | * | 2/2012 | Fanelli | C07D 309/40 514/459 |
| 2012/0041032 A1 | | 2/2012 | Puerta et al. | |
| 2012/0329741 A1 | | 12/2012 | Oyelere et al. | |
| 2014/0038990 A1 | | 2/2014 | Buschmann et al. | |
| 2014/0079666 A1 | | 3/2014 | Webb et al. | |
| 2015/0202208 A1 | | 7/2015 | Kiyama et al. | |
| 2017/0088532 A1 | * | 3/2017 | Cohen | C07D 213/81 |
| 2018/0319761 A1 | * | 11/2018 | Teng | C07D 405/06 |
| 2018/0327365 A1 | * | 11/2018 | Teng | C07D 403/12 |
| 2019/0106398 A1 | * | 4/2019 | Cohen | C07D 309/32 |

FOREIGN PATENT DOCUMENTS

| | | | |
|---|---|---|---|
| WO | WO-2004062601 A2 | 7/2004 | |
| WO | WO-2005110399 A2 * | 11/2005 | ........... A61K 31/167 |
| WO | WO-2006028523 A2 * | 3/2006 | ........... A61K 31/167 |
| WO | WO-2008027466 A1 | 3/2008 | |
| WO | WO-2008045668 A1 | 4/2008 | |
| WO | WO-2008154642 A2 | 12/2008 | |
| WO | WO-2010059838 A2 | 5/2010 | |
| WO | WO-2010100475 A1 | 9/2010 | |
| WO | WO-2012151567 A1 | 11/2012 | |
| WO | WO-2012177638 A1 | 12/2012 | |
| WO | WO-2013151923 A1 | 10/2013 | |
| WO | WO-2014117090 A1 | 7/2014 | |
| WO | WO-2014160649 A1 | 10/2014 | |
| WO | WO-2015024010 A2 | 2/2015 | |
| WO | WO-2015085238 A1 * | 6/2015 | |
| WO | WO-2015099107 A1 | 7/2015 | |
| WO | WO-2017083431 A2 | 5/2017 | |
| WO | WO-2017083434 A1 | 5/2017 | |
| WO | WO-2018208985 A2 | 11/2018 | |
| WO | WO-2018208987 A2 | 11/2018 | |

OTHER PUBLICATIONS

T. Storr et al., 14 Bioconjugate Chem., 212-221 (2008) (Year: 2008).*
Y. Li et al., 158 European Journal of Medicinal Chemistry, 753-766 (2018) (Year: 2018).*
Bingi et al. One-pot catalyst free synthesis of novel kojic acid tagged 2-aryl/alkyl substituted-4H-chromenes and evaluation of their antimicrobial and anti-biofilm activities. Bioorganic & Medicinal Chemistry Letters25(9):1915-1919 (2015).
PCT/US2015/061198 Preliminary Report on Patentability dated May 24, 2018.
PCT/US2016/061195 International Preliminary Report on Patentability dated May 24, 2018.
PCT/US2018/031896 International Search Report and Written Opinion dated Nov. 7, 2018.

(Continued)

*Primary Examiner* — Alexander R Pagano
(74) *Attorney, Agent, or Firm* — Wilson Sonsini Goodrich & Rosati

(57) ABSTRACT

The present teachings relate to pyrone derivatives, pharmaceutical compositions thereof, and methods of using such compounds to treat bacterial infections.

14 Claims, 19 Drawing Sheets

(56) References Cited

OTHER PUBLICATIONS

PCT/US2018/031898 International Search Report and Written Opinion dated Nov. 7, 2018.
Aytemir et al. Synthesis and Evaluation of Anticonvulsant and Antimicrobial Activities of 3-Hydroxy-6-methyl-2-substituted 4H-Pyran-4-one Derivatives. Archiv Der Pharmazie 337(5):281-288 (2004).
Emami et al. Mannich bases of 7-piperazinylquinolones and kojic acid derivatives: Synthesis, in vitro antibacterial activity and in silico study. EP J Med Chem 68:185-191 (2010).
Us et al. 4H-Pyran-4-one derivatives:; leading molecule for preparation of compounds with antimycobacterial potential. Turkish Journal of Chemistry 30:803-812 (2009).
Us et al. Mannich base derivatives of 3-hydroxy-6-methyl-4H-pyran-4-one with antimicrobial activity. Turkish Journal of Chemistry 33:447-456 (2010).
U.S. Appl. No. 15/773,975 Office Action dated Jan. 29, 2019.
Ding et al. Design, synthesis and biological evaluation of LpxC inhibitors with novel hydrophilic terminus. Chinese Chemical Letters 26(6):763-767 (2015).
PCT/US2016/061195 International Search Report and Written Opinion dated Jul. 31, 2017.
PCT/US2016/061198 International Search Report and Written Opinion dated Feb. 15, 2017.
Ravin. Chapter 76: Preformulation. Remington's Pharmaceutical Sciences, 17th ed., Mack Publishing Company, Easton, Pa. (pp. 1409-1423) (1985).
Yan et al. Synthesis of hydroxypyrone- and hydroxythiopyrone-based matrix metalloproteinase inhibitors: Developing a structure-activity relationship. Bioorg. Med. Chem. Lett. 19(7):1970-1976 (2009).
Di Francesco et al. Development of 2-t butyl-N-methyl pyrimidones as potent inhibitors of HIV integrase. Bioorg Med Chem Lett 18(8):2709-13 (2008).
Krivonogov et al. Aminomethylation of pyrimidines. Russian Journal of Organic Chemistry 36(8):1219-1224 Chemical Abstracts CAS No. 345959-90-2P (2000).
Hale et al. Exploring the UDP pocket of LpxC through amino acid analogs. Bioorg Med Chem Lett. 23:2362-2367 (2013).
PCT/US2019/052021 International Search Report and Written Opinion dated Jan. 6, 2020.

\* cited by examiner

PYRONE BASED COMPOUNDS FOR TREATING BACTERIAL INFECTIONS

CROSS-REFERENCE TO RELATED APPLICATIONS

This application is filed pursuant to 35 U. SC. § 371 as a United States National Phase Application of International Application No. PCT/US2016/061198, filed Nov. 9, 2016; which claims the benefit of U.S. Provisional Patent Application No. 62/252,795, filed Nov. 9, 2015, all of which are incorporated herein by reference in their entirety.

BACKGROUND OF THE INVENTION

Metalloproteins influence a vast diversity of biological systems, biological processes, and diseases. For example, UDP-{3-O—[(R)-3-hydroxymyristoyl]}-N-acetylglucosamine deacetylase (LpxC) is an essential enzyme involved in the first committed step in lipid A biosynthesis for gram-negative bacteria. Lipid A is an essential component of the outer membrane of Gram-negative bacteria. LpxC is a zinc(II)-dependent metalloenzyme, with two histidines and an aspartic acid residue bound to the zinc(II) ion. Structures of LpxC show the zinc(II) ion is bound to two water molecules, both of which have been implicated in the mechanism of the enzyme. LpxC is highly conserved across strains of Gram-negative bacteria. This makes LpxC an attractive target to treat Gram-negative infections.

Many LpxC inhibitors developed to date have issues including lack of cell permeability, off-target toxicity, and efflux.

In recent years, there has been an increase in resistant and multi-drug resistant strains of bacteria. Thus, there is a need for new antibiotics, especially with new mechanisms of action. There remains a need for metalloprotein modulators of LpxC useful in the field of therapeutics, diagnostics, and research.

SUMMARY OF THE INVENTION

Provided herein in some embodiments are compounds and compositions useful for treating bacterial infections. Some embodiments provided herein describe a compound having the structure of Formula VIII:

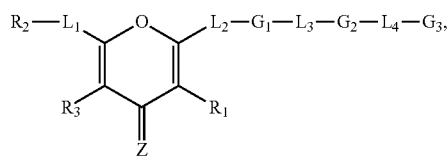

VIII or a pharmaceutically acceptable salt thereof,
wherein:
$R_1$ is —OH, —NH$_2$, or SH;
$R_2$ is H, —OR$^a$, $C_{1-6}$ alkyl, or $C_{1-6}$ alkoxy;
$R_3$ is H or $C_{1-6}$ alkyl;
Z is O or S;
$L_1$ is a bivalent radical selected from a bond, —C(=O)—, —C(=O)O—, —OC(=O)—, —C(=O)NR$^b$—, —N(R$^b$)C(=O)—, —N(R$^b$)—, —S(=O)$_2$—, —(C$_{1-4}$ alkylene)-, —(C$_{1-4}$ alkylene)-O—, —(C$_{1-4}$ alkylene)-N(R$^b$)—, —(C$_{1-4}$ alkylene)-S—, or —(C$_{1-4}$ alkylene)-S(=O)$_2$—;

$L_2$ is a bivalent radical selected from —(C(R$_4$)(R$_5$))$_n$— (C$_{0-3}$ alkylene)-, —(C(R$_4$)(R$_5$))$_n$—C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-C(=O)NR$_5$)—, —(C(R$_4$)(R$_5$))$_n$—(C$_{0-3}$ alkylene)-N(R$_5$)C(=O)—, —(C(R$_4$)(R$_5$))$_n$—(C$_{0-3}$ alkylene)-O—, —(C(R$_4$)(R$_5$))—(C$_{0-3}$ alkylene)-N(R$_5$)—, —(C(R$_4$)(R$_5$))$_n$—(C$_{0-3}$ alkylene)-S(=O)$_2$—, —(C(R$_4$)(R$_5$))$_n$—(C$_{0-3}$ alkylene)-S(=O)$_2$N(R$_5$)—, or —(C(R$_4$)(R$_5$))$_n$—(C$_{0-3}$ alkylene)-N(R$_5$)S(=O)$_2$—;

wherein each $R_4$ is H or optionally substituted $C_{1-6}$ alkyl; and each $R_5$ is independently H, an optionally substituted $C_{1-6}$ alkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —(C$_{0-4}$ alkylene)-OR$^f$, —(C$_{0-4}$ alkylene)-(C$_{1-4}$ alkene), —(C$_{0-4}$ alkylene)-(C$_{1-4}$ alkyne), $C_2$-$C_7$ heterocycle, —(C$_{0-4}$ alkylene)-C(=O)—(C$_1$-C$_6$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene)-N(R$^f$)$_2$, —(C$_{0-4}$ alkylene)-S(=O)$_2$—(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)-C(=O)NR$^b$R$^f$ or —(C$_{0-4}$ alkylene)-NR$^b$C(=O)R$^f$;

wherein each R$^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$L_3$ is a bivalent radical selected from —(C$_{2-6}$ alkenylene)-, or —(C$_{2-6}$ alkynylene)-;

$L_4$ is a bivalent radical selected from a bond, —C(=O)—, —(C(=O)O)—, —(C(=O)NR$^e$)—N(R$^e$)C(=O)—, or —(C$_{1-4}$ alkylene)-;

$G_1$ and $G_2$ are each independently, at each occurrence, a bivalent radical selected from —(C$_{6-14}$ arylene)- or -(5- to 14-membered heteroarylene)-;

$G_3$ is H, $C_{1-6}$ alkyl, $C_{3-7}$ cycloalkyl, $C_{3-10}$ heterocycloalkyl, $C_{6-14}$ aryl, 5- to 14-membered heteroaryl ene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl);

R$^a$, R$^b$, R$^c$, R$^d$, and R$^e$ are each independently, at each occurrence, H or $C_{1-6}$ alkyl; and n is 1 or 2.

In some embodiments, $R_1$ is —OH; $R_2$ is H or $C_{1-6}$ alkyl; $R_3$ is H or $C_{1-6}$ alkyl; Z is O; $L_1$ is a bond; $L_2$ is a bivalent radical is selected from —(C(R$_4$)(R$_5$))$_n$—(C$_{0-3}$ alkylene), or —C(R$_4$)(R$_5$))$_n$—(C$_{0-3}$ alkylene)-N(R$_5$)—; wherein R$_4$ is H or $C_{1-6}$ alkyl; R$_5$ is independently H or $C_{1-6}$ alkyl; $L_3$ is a bivalent radical selected from —(C$_{2-6}$ alkenylene)-, or —(C$_{2-6}$ alkynylene)-; $L_4$ is a bivalent radical selected from a bond, —C(=O)—, —(C(=O)O)—, —(C(=O)NR$^e$)—, —N(R$^e$)C(=O)—, or —(C$_{1-4}$ alkylene)-; $G_1$ and $G_2$ are each independently, at each occurrence, a bivalent radical selected from —(C$_{6-14}$ arylene)- or -(5- to 14-membered heteroarylene)-; $G_3$ is H, $C_{1-6}$ alkyl, $C_{3-7}$ cycloalkyl, $C_{3-10}$ heterocycloalkyl, $C_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl); R$^c$ and R$^e$ are each independently, at each occurrence, H or $C_{1-6}$ alkyl; and n is 1 or 2.

In other embodiments, $L_2$ is a bivalent radical selected from —(C(R$_4$)(R$_5$))$_n$—(C$_{0-3}$ alkylene)-(C(=O)NR$_5$)—, —(C(R$_4$)(R$_5$))$_n$—(C$_{0-3}$ alkylene)-N(R$_5$)C(=O)—, or —(C(R$_4$)(R$_5$))$_n$—(C$_{0-3}$ alkylene)-N(R$_5$)—; L$_3$ is a bivalent radical —(C$_{1-6}$ alkynylene)-; L$_4$ is a bivalent radical selected from a bond, —C(=O)—, —(C(=O)O)—, —C(=O)NR$^e$)—, —N(R$^e$)C(=O)—, or —(C$_{1-4}$ alkylene)-; G$_1$ and G$_2$ are each independently, at each occurrence, a bivalent radical selected from —(C$_6$ arylene)- or -(5- to 6-membered heteroarylene)-; and G$_3$ is H, C$_{1-6}$ alkyl, C$_{3-7}$ cycloalkyl, C$_{3-10}$ heterocycloalkyl, 5- to 6-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl).

Other embodiments provided herein describe a compound having the structure of Formula IX:

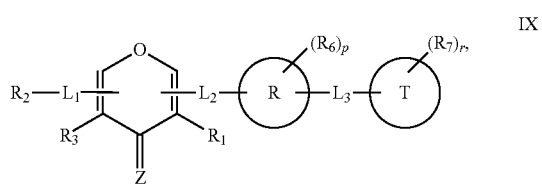

or a pharmaceutically acceptable salt thereof,
wherein:
R$_1$ is H, C$_{1-6}$ alkyl, —OH, —NH$_2$, or SH;
R$_2$ is H, —OR$^a$, C$_{1-6}$ alkyl, or C$_{1-6}$ alkoxy;
R$_3$ is H, C$_{1-6}$ alkyl, —OH, —NH$_2$, or SH;
R$_6$ and R$_7$ are each independently, at each occurrence, —OH, —NH$_2$, —CN, —NO$_2$, —C(=O)OR$^b$, —C(=O)N(R$^b$)$_2$, —N(R$^b$)C(=O)OR$^b$, halo, C$_{1-6}$ alkyl, C$_{1-6}$ alkoxy, or =O;
ring R is C$_{3-7}$ cycloalkyl, C$_{3-10}$ heterocycloalkyl, C$_{6-14}$ aryl, or a 5- to 14-membered heteroaryl;
ring T is C$_{3-7}$ cycloalkyl, C$_{3-10}$ heterocycloalkyl, C$_{6-14}$ aryl, or a 5- to 14-membered heteroaryl;
Z is O or S;
L$_1$ is a bivalent radical selected from a bond, —C(=O)—, —(C(=O)O)—, —OC(=O)—, —(C(=O)NR$^c$)—, —N(R$^c$)C(=O)—, —N(R$^c$)—, —S(=O)$_2$—, —(C$_{1-4}$ alkylene)-, —(C$_{1-4}$ alkylene)-O—, —(C$_{1-4}$ alkylene)-N(R$^c$)—, —(C$_{1-4}$ alkylene)-S—, or —(C$_{1-4}$ alkylene)-S(=O)$_2$—;
L$_2$ is a bivalent radical selected from —(C(R$_4$)(R$_5$))$_n$—(C$_{0-3}$ alkylene)-, —(C(R$_4$)(R$_5$))$_n$C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-(C(=O)NR$_5$)—, —(C(R$_4$)(R$_5$))$_n$—(C$_{0-3}$ alkylene)-N(R$_5$)C(=O)—, —(C(R$_4$)(R$_5$))$_n$—(C$_{0-3}$ alkylene)-O—, or —(C(R$_4$)(R$_5$))$_n$—(C$_{0-3}$ alkylene)-N(R$_5$)—;
wherein each R$_4$ is H or optionally substituted C$_{1-6}$ alkyl; and
each R$_5$ is independently H, an optionally substituted C$_{1-6}$ alkyl, an optionally substituted C$_{1-6}$ alkenyl, an optionally substituted C$_{1-6}$ alkynyl, an optionally substituted C$_{6-14}$ aryl, an optionally substituted 5- to 14-membered heteroaryl, an optionally substituted C$_3$-C$_8$ cycloalkyl, on optionally substituted —(C$_{0-4}$ alkylene)-OR$^f$, —(C$_{0-4}$ alkylene)-(C$_{1-4}$ alkene), —(C$_{0-4}$ alkylene)-(C$_{1-4}$ alkyne), C$_2$-C$_7$ heterocycle, —(C$_{0-4}$ alkylene)-C(=O)—(C$_1$-C$_6$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene)-N(R$^f$)$_2$, —(C$_{0-4}$ alkylene)-S(=O)$_2$—(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)-C(=O)NR$^b$R$^f$ or —(C$_{0-4}$ alkylene)-NR$^b$C(=O)R$^f$;

wherein each R$^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;
L$_3$ is a bivalent radical selected from a bond, —(C$_{1-6}$ alkylene)-, —(C$_{2-6}$ alkenylene)-, or —(C$_{2-6}$ alkynylene)-, —(C$_{3-10}$ heterocycloalkylene)-, —(C$_{6-14}$ arylene)-, -(5- to 14-membered heteroarylene)-;
R$^a$, R$^b$, R$^c$, R$^d$, and R$^e$ are each independently, at each occurrence, H or C$_{1-6}$ alkyl;
n is 1 or 2;
p is 0, 1, 2, or 3; and
r is 0, 1, 2, or 3,
provided that R$_1$ or R$_3$ is —OH, —NH$_2$, or SH.

Also provided herein in some embodiments is a method of modulating the activity of UDP-{3-O—[(R)-3-hydroxymyristoyl]}—N-acetylglucosamine deacetylase in a subject in need thereof comprising administering a therapeutically effective amount of a compound described herein or a pharmaceutically acceptable salt thereof.

Other embodiments provided herein describe a method of treating a gram-negative bacterial infection in a subject comprising administering to the subject a pharmaceutical composition comprising a compound described herein, or a pharmaceutically acceptable salt thereof.

Also provided herein in some embodiments is a pharmaceutical composition comprising a therapeutically effective amount of a compound described herein and a pharmaceutically acceptable excipient.

DETAILED DESCRIPTION OF THE INVENTION

Definitions

Figure 1:
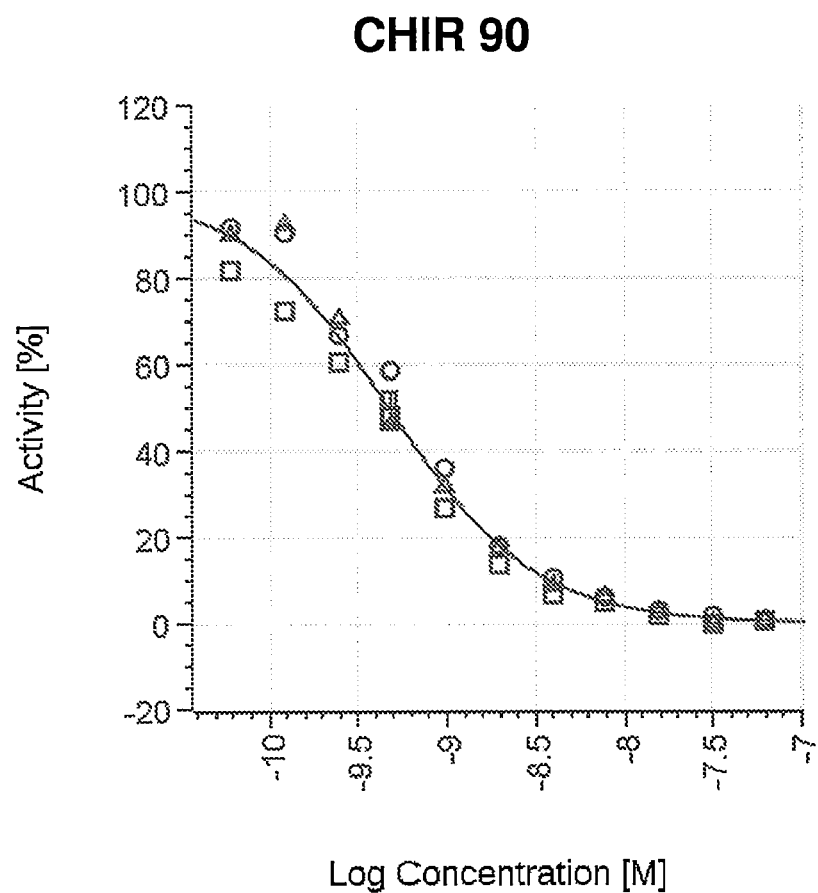
FIG. 1 shows a dose response curve for compound CHIR-090 in an LpxC inhibition assay.
Figure 2:
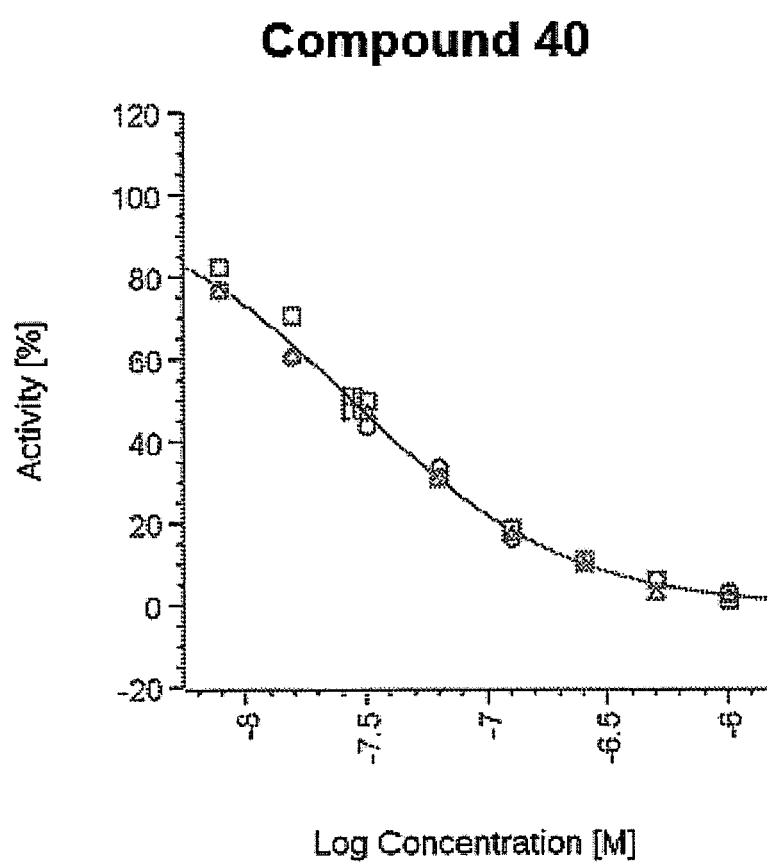
FIG. 2 shows a dose response curve for compound 40 in an LpxC inhibition assay.
Figure 3:
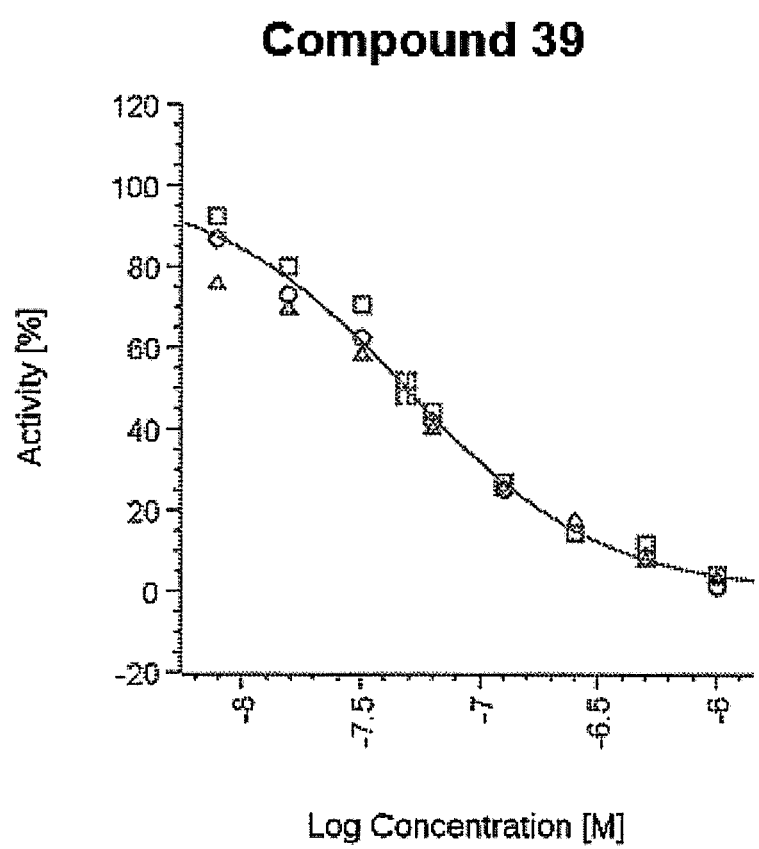
FIG. 3 shows a dose response curve for compound 39 in an LpxC inhibition assay.
Figure 4:
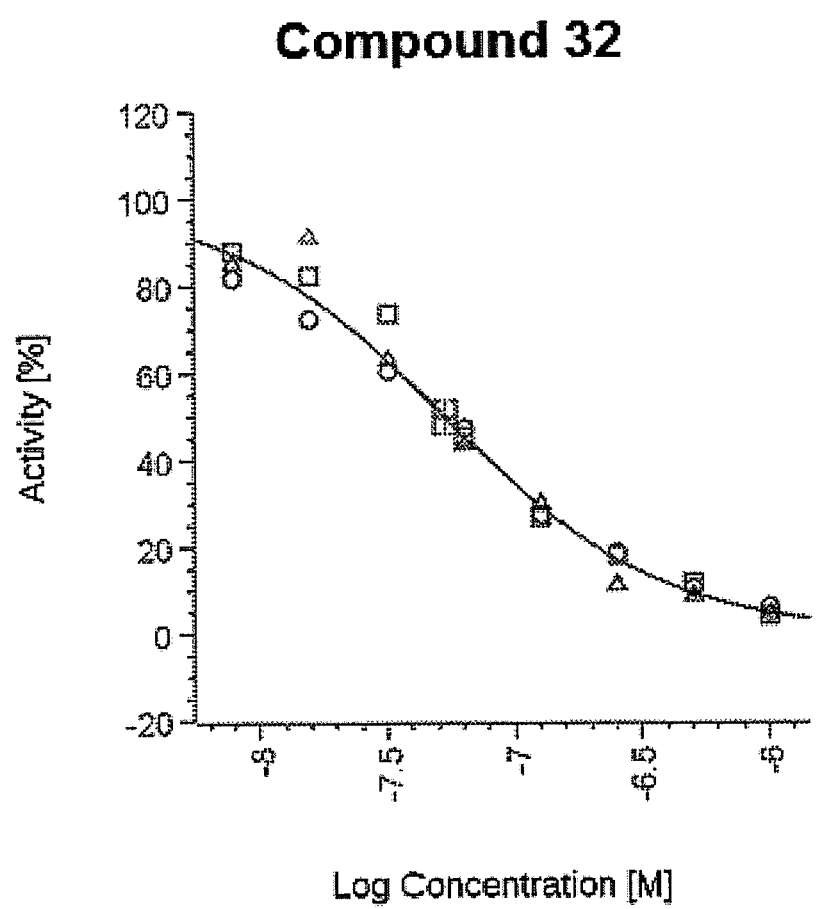
FIG. 4 shows a dose response curve for compound 32 in an LpxC inhibition assay.
Figure 5:
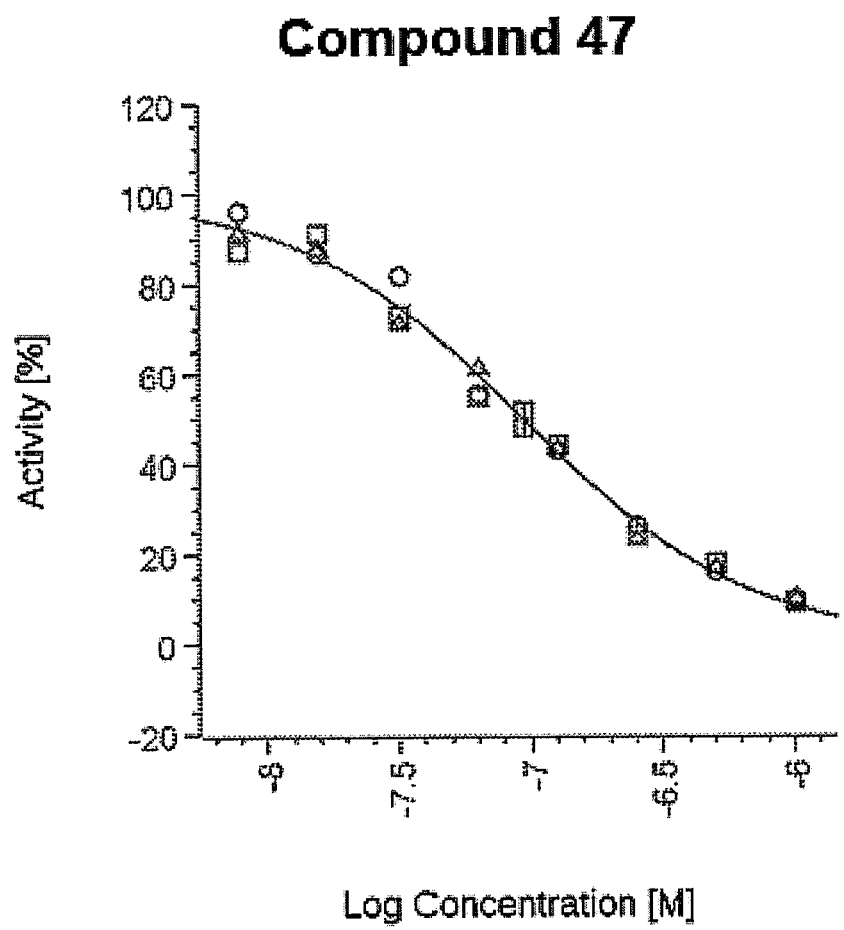
FIG. 5 shows a dose response curve for compound 47 in an LpxC inhibition assay.
Figure 6:
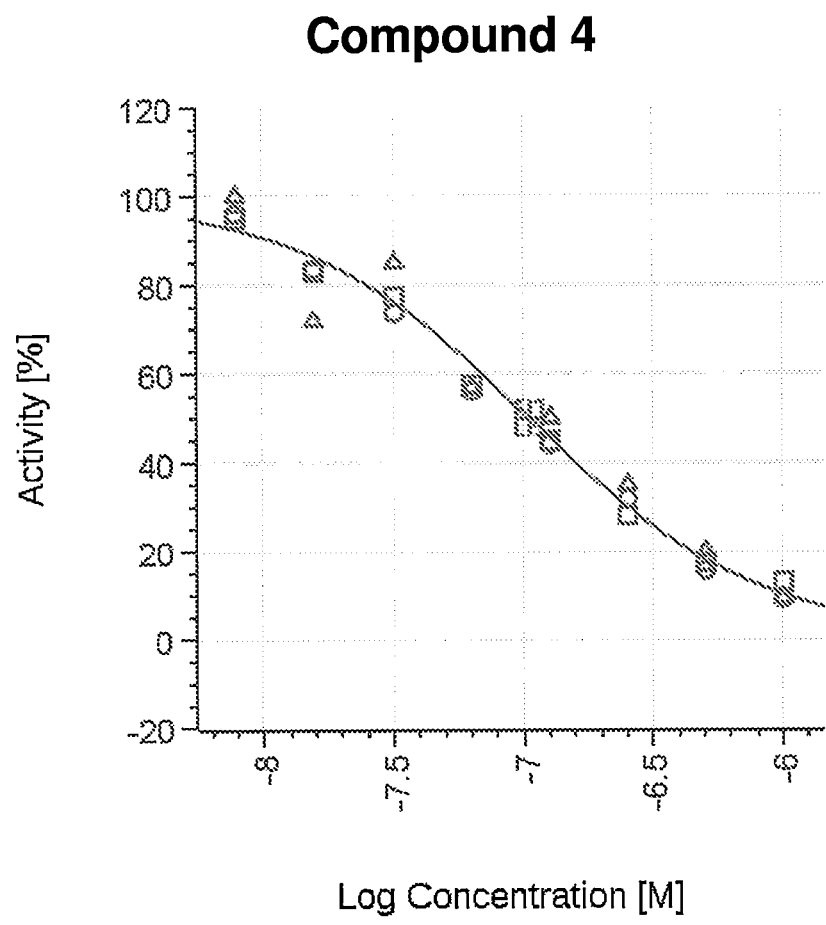
FIG. 6 shows a dose response curve for compound 4 in an LpxC inhibition assay.
Figure 7:
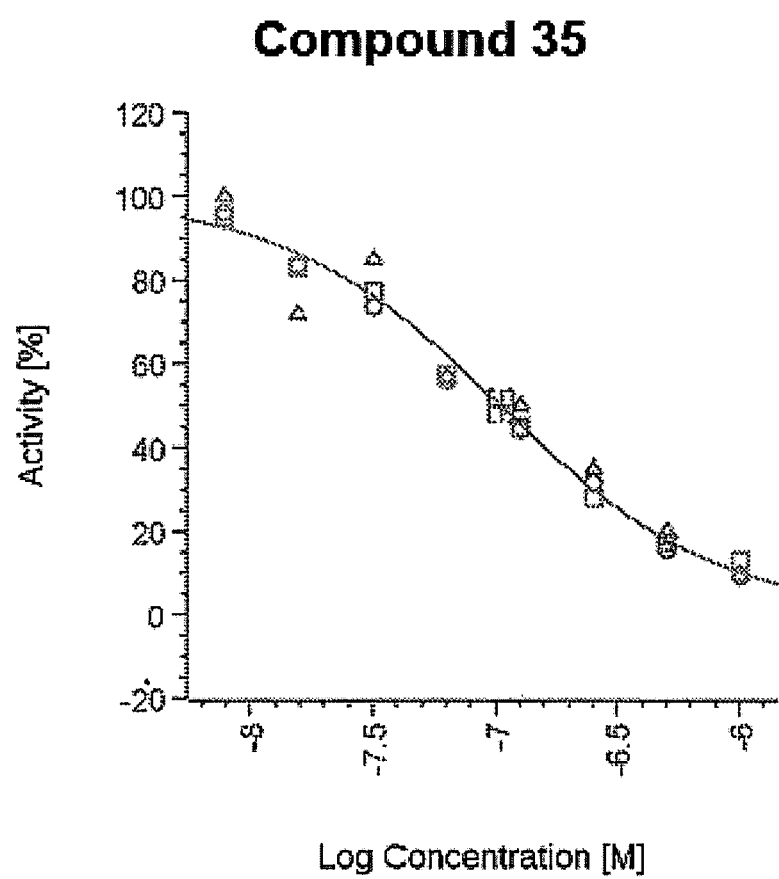
FIG. 7 shows a dose response curve for compound 35 in an LpxC inhibition assay.
Figure 8:
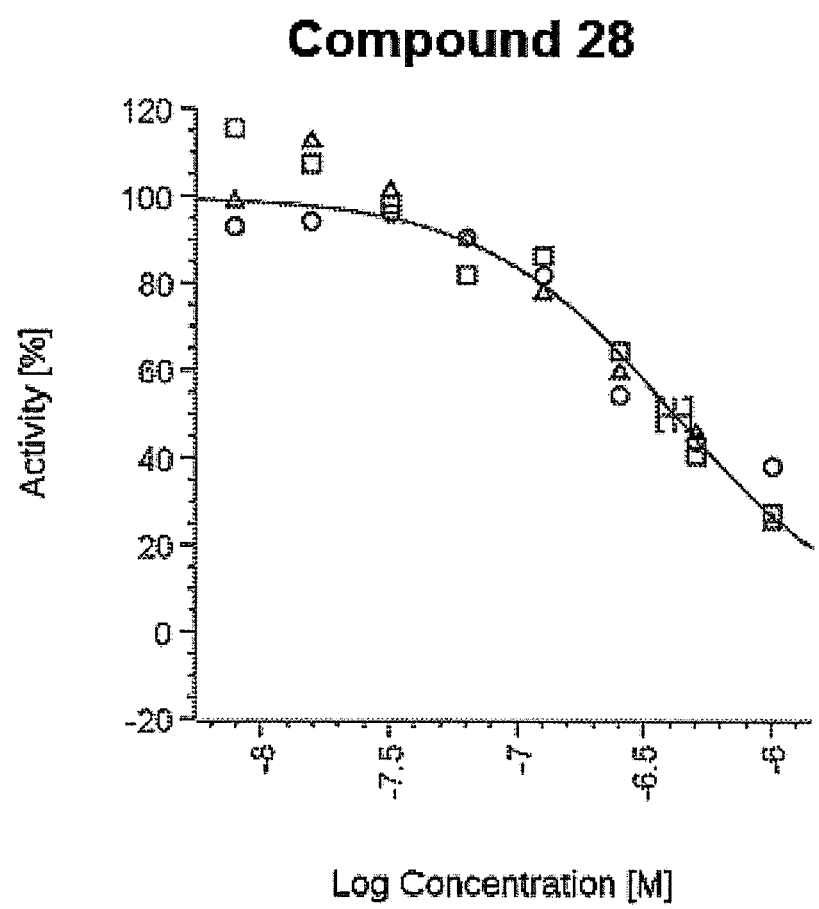
FIG. 8 shows a dose response curve for compound 28 in an LpxC inhibition assay.
Figure 9:
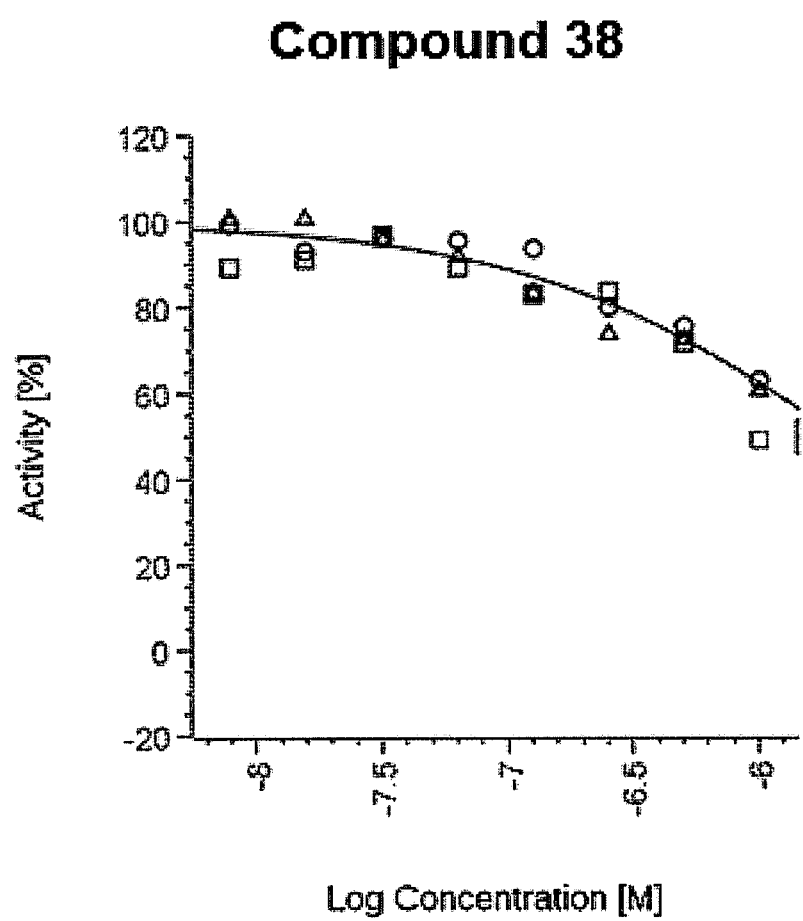
FIG. 9 shows a dose response curve for compound 38 in an LpxC inhibition assay.

As used herein, "treatment," "treating," "treat and the like refer generally to obtaining a desired pharmacological or physiological effect. The treatment may be therapeutic in terms of partial or complete stabilization or cure of a disease or adverse effects caused by the disease. "Treatment" as used herein covers any treatment of a disease in a subject, including: (a) inhibiting the symptoms of a disease, i.e., arresting its development; or (b) relieving the symptoms of a disease, i.e., causing regression of the disease or symptoms.

The phrase "therapeutically effective amount" as used herein means that amount of a compound, material, or composition comprising a compound of the present teachings that is effective for producing a desired therapeutic effect. Accordingly, a therapeutically effective amount treats a disease or a disorder, e.g., ameliorates at least one sign or symptom of the disorder. In various embodiments, the disease or disorder is a bacterial infection.

The term "alkyl" or "alkylene" as used herein refers to a fully saturated straight or branched hydrocarbon. Preferably the alkyl comprises 1-22 carbon atoms, more preferably 1-16 carbon atoms, 1-8 carbon atoms, 1-6 carbon atoms, or 1-4 carbon atoms. Exemplary alkyl groups include, but are not limited to, methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl. Alkyl groups may be substituted with one or more substituents, each of which is independently selected from, e.g., (a) oxo (=O), fluoro (—F), chloro (—Cl), bromo (—Br), iodo (—I), cyano (—CN), and nitro (—NO$_2$); (b) substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-10}$ cycloalkyl, substituted or unsubstituted $C_{6-14}$ aryl, substituted or unsubstituted $C_{7-15}$ aralkyl, substituted or unsubstituted heteroaryl, and substituted or unsubstituted heterocyclyl; and (c) —C(O)R$^a$, C(O)OR$^a$, —C(O)NR$^b$R$^c$, —C(NR$^a$)NR$^b$R$^c$, —OR$^a$, —OC(O)R$^a$, —OC(O)OR$^a$, OC(O)NR$^b$R$^c$, OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, R$^d$, and R$^e$ are each independently, at each occurrence, H or $C_{1-6}$ alkyl.

The term "alkenyl" or "alkenylene," alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups include, but are not limited to, ethenyl, 1-propenyl, 2-propenyl, isopropenyl, 1-butenyl, 2-butenyl, 3-butenyl, isobutenyl, 1-cyclopentenyl, 1-cyclohexenyl, and 2,4-hexadiene. Alkenyl groups may be substituted with one or more substituents, each of which is independently selected from, e.g., (a) oxo (=O), fluoro (—F), chloro (—Cl), bromo (—Br), iodo (—I), cyano (—CN), and nitro (—NO$_2$); (b) substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-10}$ cycloalkyl, substituted or unsubstituted $C_{6-14}$ aryl, substituted or unsubstituted $C_{7-15}$ aralkyl, substituted or unsubstituted heteroaryl, and substituted or unsubstituted heterocyclyl; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, R$^d$, and R$^e$ are each independently, at each occurrence, H or $C_{1-6}$ alkyl.

The term "alkynyl" or "alkynylene" alone or in combination refers to a straight-chain, cyclic or branched hydrocarbon residue comprising at least one carbon-carbon triple bond and the indicated number of carbon atoms. The alkynyl may contain one, two, or three carbon-carbon triple bonds. Preferred alkynyl groups have up to 8, preferably up to 6, particularly preferred up to 4 carbon atoms. Examples of alkynyl groups include, but are not limited to, ethyne (or acetylene), 1-propyne, 2-propyne, 1-butyne, 2-butyne, 3-butyne, isobutyne, 1-cyclopentynyl, 1-cyclohexynyl, and 2,4-hexadiyne. Alkynyl groups may be substituted with one or more substituents, each of which is independently selected from, e.g., (a) oxo (=O), fluoro (—F), chloro (—Cl), bromo (—Br), iodo (—I), cyano (—CN), and nitro (—NO$_2$); (b) substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-10}$ cycloalkyl, substituted or unsubstituted $C_{6-14}$ aryl, substituted or unsubstituted $C_{7-15}$ aralkyl, substituted or unsubstituted heteroaryl, and substituted or unsubstituted heterocyclyl; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, R$^d$, and R$^e$ are each independently, at each occurrence, H or $C_{1-6}$ alkyl.

The term "alkoxy" represents a chemical substituent of formula —OR, where R is a $C_{1-20}$ alkyl group (e.g., $C_{1-6}$ or $C_{1-10}$ alkyl), unless otherwise specified. An alkoxy group refers to those alkyl groups, having from 1 to 20 carbon atoms, attached to the remainder of the molecule via an oxygen atom. Exemplary alkoxy groups include methoxy, ethoxy, propoxy (e.g., n-propoxy and isopropoxy), t-butoxy, and the like. In some embodiments, the alkyl group can be further substituted with 1, 2, 3, or 4 substituent groups as defined herein (e.g., hydroxy or alkoxy).

The term "cycloalkyl" or "carbocyclic" as used herein refers to a saturated or unsaturated monocyclic, bicyclic, tricyclic, other multicyclic, or bridged cyclic hydrocarbon group. A cycloalkyl group can have 3-22 ring carbon atoms, 3-12 ring carbon atoms, or 3-7 ring carbon atoms, referred to herein as $C_3$-$C_{22}$ cycloalkyl, $C_3$-$C_{12}$ cycloalkyl, or $C_3$-$C_7$ cycloalkyl, respectively. A cycloalkyl group can also have one or more carbon-carbon double bond or carbon-carbon triple bond. Cycloalkyl groups may be substituted with one or more substituents, each of which is independently selected from, e.g., (a) oxo (=O), fluoro (—F), chloro (—Cl), bromo (—Br), iodo (—I), cyano (—CN), and nitro (—NO$_2$); (b) substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-10}$ cycloalkyl, substituted or unsubstituted $C_{6-14}$ aryl, substituted or unsubstituted $C_{7-15}$ aralkyl, substituted or unsubstituted heteroaryl, and substituted or unsubstituted heterocyclyl; and (c) —C(O)R$^a$, —C(O)OR$^a$, —C(O)$_{NR}$$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$—NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, R$^d$, and R$^e$ are each independently, at each occurrence, H or $C_{1-6}$ alkyl.

Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like. Cycloalkyl groups can be fused to other cycloalkyl saturated or unsaturated, aryl, or heterocyclyl groups.

The term "aryl" or "arylene" as used herein refers to a mono-, bi-, or other multi-carbocyclic aromatic ring system. The aryl can have 6-14 carbon atoms, or 6-10 carbon atoms, referred to herein as $C_6$-$C_{14}$ aryl, or $C_6$-$C_{10}$ aryl, respectively. The aryl group can optionally be fused to one or more rings selected from aryls and cycloalkyls. The ring systems may be partially saturated. The term "biaryl" as used herein refers to an aryl group fused or bridged to another aromatic or non-aromatic carbocyclic. The aryl may be $C_{6-20}$ biaryl. Exemplary aryl groups include, but are not limited to, phenyl, biphenyl, tolyl, anthracenyl, xylyl, anthryl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$C_6$ aryl" or phenyl. The phenyl group can also be fused to a cyclohexane or cyclopentane ring to form a biaryl. Aryl groups may be substituted with one or more substituents, each of which is independently selected from, e.g., (a) oxo (=O), fluoro (—F), chloro (—Cl), bromo (—Br), iodo (—I), cyano (—CN), and nitro (—NO$_2$); (b) substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-10}$ cycloalkyl, substituted or unsubstituted $C_{6-14}$ aryl, substituted or unsubstituted $C_{7-15}$ aralkyl, substituted or unsubstituted heteroaryl, and substituted or unsubstituted heterocyclyl; and (c) —C(O)R$^a$, —C(O)OR$^a$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, R$^d$, and R$^e$ are each independently, at each occurrence, H or $C_{1-6}$ alkyl.

The term "heterocycle" or "heterocyclyl" refers to a fully saturated or partially unsaturated nonaromatic monocyclic, bicyclic, tricyclic, other multicyclic, or bridged heterocyclic group containing at least one heteroatom such as nitrogen, oxygen, or sulfur. In some cases, the heterocycle can be 3- to 22-membered rings, 4- to 13-membered ring structures or 3- to 7-membered rings, whose ring structures include one to four heteroatoms. The heterocycle may also be referred to as $C_{3-10}$ heterocycloalkyl comprising 3 to 10 carbon atoms and 1 to 3 heteroatoms to form a 4- to 13-membered heterocycloalkyl. Nonlimiting examples include piperidinyl, morpholinyl, piperazinyl, pyrrolidinyl or pirazinyl. In some case, the heterocycle is a nitrogen heterocycle, wherein at least one ring comprises at least one nitrogen ring atom. The heterocycles may be fused to other rings to form a polycyclic heterocycloalkyl. Thus, heterocycloalkyls also include bicyclic, tricyclic, and tetracyclic groups in which any of the above heterocyclic rings is fused to one or two rings independently selected from cycloalkyls, and heterocycles. The heterocycle may also be fused to a spirocyclic group. Heterocycle groups may be substituted with one or more substituents, each of which is independently selected from, e.g., (a) oxo (=O), fluoro (—F), chloro (—Cl), bromo (—Br), iodo (—I), cyano (—CN), and nitro (—NO$_2$); (b) substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-10}$ cycloalkyl, substituted or unsubstituted $C_{6-14}$ aryl, substituted or unsubstituted $C_{7-15}$ aralkyl, substituted or unsubstituted heteroaryl, and substituted or unsubstituted heterocyclyl; and (c) —C(O)R$^a$, —C(O)OR$^a$, —C(O)$_{NR}$$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$—NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, R$^d$, and R$^e$ are each independently, at each occurrence, H or $C_{1-6}$ alkyl.

Heterocycle groups within the scope of this definition include but are not limited to imidazolyl, isothiazolyl, thiazolyl, triazinyl, triazolyl, pyrolidinyl, pyrrolinyl, piperidinyl, morpholinyl, piperazinyl, thiomorpholinyl, pyranyl and pyrazolyl.

The term "heteroaromatic," "heteroaryl," or "heteroarylene" as used herein refers to a mono-, bi-, or multicyclic aromatic ring system containing one or more heteroatoms, for example 1-4 heteroatoms, such as nitrogen, oxygen, and sulfur. For example, a bicyclic aromatic ring system containing one or more heteroatoms includes, but is not limited to, phenylpyridine, triazolylpyridine, oxazolylpyridine, thiazolylpyridine, and imidazolylpyridine. Heteroaryls can also be fused to non-aromatic rings. In various embodiments, the term "heteroaromatic" or "heteroaryl," as used herein except where noted, represents a stable 5- to 7-membered monocyclic, stable 9- to 10-membered fused bicyclic, or a stable 12- to 14-membered fused tricyclic heterocyclic ring system, or a stable 5- to 14-membered heteroarylene, which contains an aromatic ring that contains at least one heteroatom selected from the group consisting of nitrogen, oxygen, and sulfur. In some embodiments, at least one nitrogen atom is in the aromatic ring. Heteroaryl groups may be substituted with one or more substituents, each of which is independently selected from, e.g., (a) oxo (=O), fluoro (—F), chloro (—Cl), bromo (—Br), iodo (—I), cyano (—CN), and nitro (—NO$_2$); (b) substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-10}$ cycloalkyl, substituted or unsubstituted C$_{6-14}$ aryl, substituted or unsubstituted C$_{7-15}$ aralkyl, substituted or unsubstituted heteroaryl, and substituted or unsubstituted heterocyclyl; and (c) (c) —C(O)R$^a$, —C(O)OR$^a$, —C(O)$_{NR}{}^bR^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, R$^d$, and R$^e$ are each independently, at each occurrence, H or C$_{1-6}$ alkyl.

The terms "heterobiaryl" and "heterobicycloalkyl" as used herein refers to a heteroaryl group fused to another aromatic or non-aromatic carbocyclic or heterocyclic ring. Exemplary heterobiaryls and heterobicycloalkyls include, but are not limited to 5,6- or 6,6-fused systems, wherein one or both rings contain heteroatoms. The term heterobiaryl or heterobicycloalkyl also encompasses reduced or partly reduced forms of fused aromatic system wherein one or both rings contain ring heteroatoms. The ring system may contain up to four heteroatoms, independently selected from oxygen, nitrogen, and sulfur. These groups may also be referred to as "C$_{8-11}$ heterobiaryl," "fused 5- to 12-membered heterobicycloalkyl," and fused 8- to 11-membered heterobiaryl. Heterobiaryl groups may be substituted with one or more substituents, each of which is independently selected from, e.g., (a) oxo (=O), fluoro (—F), chloro (—Cl), bromo (—Br), iodo (—I), cyano (—CN), and nitro (—NO$_2$); (b) substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-10}$ cycloalkyl, substituted or unsubstituted C$_{6-14}$ aryl, substituted or unsubstituted C$_{7-15}$ aralkyl, substituted or unsubstituted heteroaryl, and substituted or unsubstituted heterocyclyl; and (c) (c) —C(O)R$^a$, —C(O)OR$^a$, —C(O)$_{NR}{}^bR^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$—NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, R$^d$, and R$^e$ are each independently, at each occurrence, H or C$_{1-6}$ alkyl.

Heteroaryl groups within the scope of this definition include but are not limited to: acridinyl, carbazolyl, cinnolinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline.

The terms "halo" or "halogen," by themselves or as part of another substituent, mean, unless otherwise stated, a fluorine, chlorine, bromine, or iodine atom.

The terms "hydroxy" and "hydroxyl" as used herein refers to —OH.

The term "nitro" as used herein refers to NO$_2$.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

The term "optionally substituted" is intended to mean that a group or substituent, such as an alkyl, alkylene, heteroalkylene, alkenyl, alkenylene, heteroalkenylene, alkynyl, cycloalkyl, cycloalkenyl, aryl, aralkyl, heteroaryl, heteroaryl-C$_{1-6}$ alkyl, and heterocyclyl group, may be substituted with one or more substituents, each of which is independently selected from, e.g., (a) oxo (=O), fluoro (—F), chloro (—Cl), bromo (—Br), iodo (—I), cyano (—CN), and nitro (—NO$_2$); (b) substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-10}$ cycloalkyl, substituted or unsubstituted C$_{6-14}$ aryl, substituted or unsubstituted C$_{7-15}$ aralkyl, substituted or unsubstituted heteroaryl, and substituted or unsubstituted heterocyclyl; and (c) —C(O)R$^a$, —C(O)OR$^a$, —C(O)$_{NR}{}^bR^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$—NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, R$^d$, and R$^e$ are each independently, at each occurrence, H or C$_{1-6}$ alkyl.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Compounds of the Disclosure

The present disclosure provides pyrone derivatives, pharmaceutical compositions thereof, and methods of using such compounds to treat or alleviate a disease or condition. Provided herein are compounds and compositions thereof useful to treat bacterial infections.

In one aspect, the disclosure provides a metal-binding compound comprising a pyrone derivatives. In other embodiments, the metal-binding compound has the following structural formula with the positional numbering below:

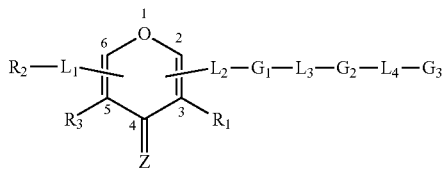

In some embodiments, a compound of the disclosure has the following structural formula:

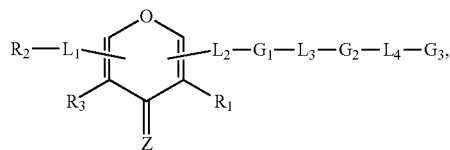

VII or a pharmaceutically acceptable salt thereof,
wherein:
$R_1$ is H, —OH, —NH$_2$, or SH;
$R_2$ is H, —OR$^a$, —N(R$^a$)$_2$, $C_{1-6}$ alkyl, or $C_{1-6}$ alkoxy;
$R_3$ is H, —OH, $C_{1-6}$ alkyl, or $C_{1-6}$ alkoxy;
Z is O or S;
$L_1$ is a bivalent radical selected from a bond, —C(=O)—, —C(=O)O—, —OC(=O)—, —C(=O)NR$^b$—, —N(R$^b$)C(=O)—, —N(R$^b$)—, —S(=O)$_2$—, —(C$_{1-4}$ alkylene)-, —(C$_{1-4}$ alkylene)-O—, —(C$_{1-4}$ alkylene)-N(R$^b$)—, alkylene)-S—, or —(C$_{1-4}$ alkylene)-S(=O)$_2$—;

$L_2$ is a bivalent radical selected from —(C(R$_4$)(R$_5$))$_n$—(C$_{0-3}$ alkylene)-, —(C(R$_4$)(R$_5$))$_n$—C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-C(=O)NR$_5$)—, —(C(R$_4$)(R$_5$))$_n$—(C$_{0-3}$ alkylene)-N(R$_5$)C(=O)—, —(C(R$_4$)(R$_5$))$_n$(C$_{0-3}$ alkylene)-O—, —(C(R$_4$)(R$_5$))$_n$—(C$_{0-3}$ alkylene)-N(R$_5$)—, —(C(R$_4$)(R$_5$))$_n$—(C$_{0-3}$ alkylene)-S(=O)$_2$—, —(C(R$_4$)(R$_5$))$_n$—(C$_{0-3}$ alkylene)-S(=O)$_2$N(R$_5$)—, or —(C(R$_4$)(R$_5$))$_n$—(C$_{0-3}$ alkylene)-N(R$_5$)S(=O)$_2$—;

wherein each $R_4$ is H or optionally substituted $C_{1-6}$ alkyl; and
each $R_5$ is independently H, an optionally substituted $C_{1-6}$ alkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —(C$_{0-4}$ alkylene)-OR$^f$, —(C$_{0-4}$ alkylene)-(C$_{1-4}$ alkene), —(C$_{0-4}$ alkylene)-(C$_{1-4}$ alkyne), C$_2$-C$_7$ heterocycle, —(C$_{0-4}$ alkylene)-C(=O)—(C$_1$-C$_6$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene)-N(R$^f$)$_2$, —(C$_{0-4}$ alkylene)-S(=O)$_2$—(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)-C(=O)NR$^b$R$^f$ or —(C$_{0-4}$ alkylene)-NR$^b$C(=O)R$^f$;

wherein each R$^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$L_3$ is a bivalent radical selected from a bond, —(C$_{1-6}$ alkylene)-, —(C$_{2-6}$ alkenylene)-, or —(C$_{2-6}$ alkynylene)-, —(C$_{3-10}$ heterocycloalkylene)-, —(C$_{6-14}$ arylene)-, -(5- to 14-membered heteroarylene)-;

$L_4$ is a bivalent radical selected from a bond, —C(=O)—, —(C(=O)O)—, —OC(=O)—, —C(=O)NR$^e$—, —N(R$^e$)C(=O)—, —N(R$^e$)—, —S(=O)$_2$—, or —(C$_{1-4}$ alkylene)-;

$G_1$ and $G_2$ are each independently, at each occurrence, a bivalent radical selected from —(C$_{6-14}$ arylene)- or -(5- to 14-membered heteroarylene)-;

$G_3$ is H, CN, $C_{1-6}$ alkyl, $C_{3-7}$ cycloalkyl, $C_{3-10}$ heterocycloalkyl, $C_{6-14}$ aryl, 5- to 14-membered heteroarylene, fused 5- to 12-membered heterobicycloalkyl, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), (5- to 14-membered heteroarylene)-(C$_{1-4}$ heteroalkyl), (fused 5- to 12-membered heterobicycloalkyl)-(C$_{1-4}$ heteroalkyl), or (fused 8- to 11-membered heterobiaryl)-(C$_{1-4}$ heteroalkyl); and $R^a$, $R^b$, $R^c$, $R^d$, and $R^e$ are each independently, at each occurrence, H or $C_{1-6}$ alkyl; and
n is 1 or 2,
provided that $R_1$ or $R_3$ is —OH, —NH$_2$, or SH.

In one embodiment of Formula VII, $R_4$ is H or $C_{1-6}$ alkyl; and $R_5$ is H, $C_{1-6}$ alkyl, —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), or —(C$_{1-4}$ alkylene)-(5- to 14-membered heteroaryl);

In one embodiment, each $R_5$ is H, $C_{1-6}$ alkyl, —(C$_{0-4}$ alkylene)-OR$^f$, —(C$_{0-4}$ alkylene)-N(R$^f$)$_2$, —(C$_{0-4}$ alkylene)-

S(=O)$_2$—(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)-C(=O)NR$^b$R$^f$ or —(C$_{0-4}$ alkylene)-NR$^b$C(=O)R$^f$.

In some embodiments of Formula VII, Z is O. In another embodiment of Formula VII, Z is S. In yet another embodiment, L$_1$ bivalent radical selected from a bond, —(C$_{1-4}$ alkylene)-O—, —(C$_{1-4}$ alkylene)-N(R$^b$)—, —(C$_{1-4}$ alkylene)-S—, —(C$_{1-4}$ alkylene)-S(=O)$_2$—; R$_2$ is H, —OR$^a$, —N(R$^a$)$_2$, C$_{1-6}$ alkyl, or C$_{1-6}$ alkoxy; and R$^b$ is H or C$_{1-6}$ alkyl. In one embodiment, R$_5$ is not hydrogen. In another embodiment, R$_5$ is —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), or —(C$_{1-4}$ alkylene)-(5- to 14-membered heteroaryl). In certain embodiments, R$_5$ is —(C$_{1-4}$ alkylene)-OR$^d$, —(C$_{1-4}$ alkylene)-N(R$^d$)$_2$, or —(C$_{1-4}$ alkylene)-S(=O)$_2$—(R$^d$). In yet another embodiment, L$_3$ is a bivalent radical selected from —(C$_{2-6}$ alkenylene)-, —(C$_{2-6}$ alkynylene)-, —(C$_{3-10}$ heterocycloalkylene)-, —(C$_{6-14}$ arylene)-, or -(5- to 14-membered heteroarylene)-. In still another embodiment, L$_3$ is a bond.

In other embodiments of Formula VII, the compound has the following structural formula:

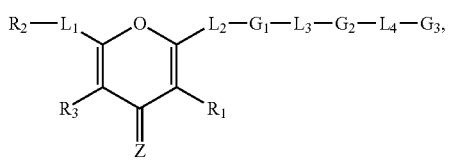

VIII or a pharmaceutically acceptable salt thereof,
wherein:
R$_1$ is —OH, —NH$_2$, or SH;
R$_2$ is H, —OR$^a$, C$_{1-6}$ alkyl, or C$_{1-6}$ alkoxy;
R$_3$ is H or C$_{1-6}$ alkyl;
Z is O or S;
L$_1$ is a bivalent radical selected from a bond, —C(=O)—, —(C(=O)O)—, —OC(=O)—, —(C(=O)NR$^b$)—, —N(R$^b$)C(=O)—, —N(R$^b$)—, —S(=O)—, —(C$_{1-4}$ alkylene)-, —(C$_{1-4}$ alkylene)-O—, —(C$_{1-4}$ alkylene)-N(R$^b$)—, —(C$_{1-4}$ alkylene)-S—, or —(C$_{1-4}$ alkylene)-S(=O)$_2$—;
L$_2$ is a bivalent radical selected from —(C(R$_4$)(R$_5$))$_n$—(C$_{0-3}$ alkylene)-, —(C(R$_4$)(R$_5$))$_n$—C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-C(=O)NR$_5$)—, —(C(R$_4$)(R$_5$))$_n$—(C$_{0-3}$ alkylene)-N(R$_5$)C(=O)—, —(C(R$_4$)(R$_5$))$_n$(C$_{0-3}$ alkylene)-O—, —(C(R$_4$)(R$_5$))$_n$—(C$_{0-3}$ alkylene)-N(R$_5$)—, —(C(R$_4$)(R$_5$))$_n$—(C$_{0-3}$ alkylene)-S(=O)$_2$—, —(C(R$_4$)(R$_5$))$_n$—(C$_{0-3}$ alkylene)-S(=O)$_2$N(R$_5$)—, or —(C(R$_4$)(R$_5$))$_n$—(C$_{0-3}$ alkylene)-N(R$_5$)S(=O)$_2$—;
wherein each R$_4$ is H or optionally substituted C$_{1-6}$ alkyl; and
each R$_5$ is independently H, an optionally substituted C$_{1-6}$ alkyl, an optionally substituted C$_{1-6}$ alkenyl, an optionally substituted C$_{1-6}$ alkynyl, an optionally substituted C$_{6-14}$ aryl, an optionally substituted 5- to 14-membered heteroaryl, an optionally substituted C$_3$-C$_8$ cycloalkyl, on optionally substituted —(C$_{0-4}$ alkylene)-OR$^f$, —(C$_{0-4}$ alkylene)-(C$_{1-4}$ alkene), —(C$_{0-4}$ alkylene)-(C$_{1-4}$ alkyne), C$_2$-C$_7$ heterocycle, —(C$_{0-4}$ alkylene)-C(=O)—(C$_1$-C$_6$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene)-N(R$^f$)$_2$, —(C$_{0-4}$ alkylene)-S(=O)$_2$—(R$^f$), —(C$_{0-4}$ alkylene)-(C$_{0-14}$ aryl), —(C$_{1-4}$ alkylene)-(5- to 14-membered heteroaryl), —(C$_{0-4}$ alkylene)-C(=O)NR$^b$R$^f$ or —(C$_{0-4}$ alkylene)-NR$^b$C(=O)R$^f$;
wherein each R$^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;
L$_3$ is a bivalent radical selected from —(C$_{2-6}$ alkenylene)-, or —(C$_{2-6}$ alkynylene)-;
L$_4$ is a bivalent radical selected from a bond, —C(=O)—, —(C(=O)O)—, —(C(=O)NR$^e$)—, —N(R$^e$)C(=O)—, or —(C$_{1-4}$ alkylene)-;
G$_1$ and G$_2$ are each independently, at each occurrence, a bivalent radical selected from —(C$_{6-14}$ arylene)- or -(5- to 14-membered heteroarylene)-;
G$_3$ is H, C$_{1-6}$ alkyl, C$_{3-7}$ cycloalkyl, C$_{3-10}$ heterocloalkyl, C$_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl);
R$^a$, R$^b$, R$^c$, R$^d$, and R$^e$ are each independently, at each occurrence, H or C$_{1-6}$ alkyl; and
n is 1 or 2.

Some embodiments provided herein describe a compound of Formula VIII wherein wherein:
R$_1$ is —OH;
R$_2$ is H, —OR$^a$, C$_{1-6}$ alkyl, or C$_{1-6}$ alkoxy;
R$_3$ is H;
Z is O;
L$_1$ is a bivalent radical selected from a bond, —C(=O)—, —(C(=O)O)—, —OC(=O)—, —(C(=O)NR$^b$)—, —N(R$^b$)C(=O)—, —N(R$^b$)—, —S(=O)—, —(C$_{1-4}$ alkylene)-, —(C$_{1-4}$ alkylene)-O—, —(C$_{1-4}$ alkylene)-N(R$^b$)—, —(C$_{1-4}$ alkylene)-S—, or —(C$_{1-4}$ alkylene)-S(=O)$_2$—;
L$_2$ is —(C(R$_4$)(R$_5$))$_n$—(C$_{0-3}$ alkylene)-, —(C(R$_4$)(R$_5$))$_n$—C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-(C(=O)NR$_5$)—, —(C(R$_4$)(R$_5$))$_n$—(C$_{0-3}$ alkylene)-N(R$_5$)C(=O)—, —(C(R$_4$)(R$_5$))$_n$(C$_{0-3}$ alkylene)-O—, —(C(R$_4$)(R$_5$))$_n$—(C$_{0-3}$ alkylene)-N(R$_5$)—, —(C(R$_4$)(R$_5$))$_n$—(C$_{0-3}$ alkylene)-S(=O)$_2$—, —(C(R$_4$)(R$_5$))$_n$—(C$_{0-3}$ alkylene)-S(=O)$_2$N(R$_5$)—, or —(C(R$_4$)(R$_5$))$_n$—(C$_{0-3}$ alkylene)-N(R$_5$)S(=O)$_2$—;
wherein each R$_4$ is H or optionally substituted C$_{1-6}$ alkyl; and
each R$_5$ is independently H, an optionally substituted C$_{1-6}$ alkyl, an optionally substituted C$_{1-6}$ alkenyl, an optionally substituted C$_{1-6}$ alkynyl, an optionally substituted C$_{6-14}$ aryl, an optionally substituted 5- to 14-membered heteroaryl, an optionally substituted C$_3$-C$_8$ cycloalkyl, on optionally substituted —(C$_{0-4}$ alkylene)-OR$^f$, —(C$_{0-4}$ alkylene)-(C$_{1-4}$ alkene), —(C$_{0-4}$ alkylene)-(C$_{1-4}$ alkyne), C$_2$-C$_7$ heterocycle, —(C$_{0-4}$ alkylene)-C(=O)—(C$_1$-C$_6$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene)-N(R$^f$)$_2$, —(C$_{0-4}$ alkylene)-S(=O)$_2$—(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)-C(=O)NR$^b$R$^f$ or —(C$_{0-4}$ alkylene)-NR$^b$C(=O)R$^f$;
wherein each R$^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$L_3$ is —($C_{2-6}$ alkynylene)-;

$L_4$ is a bond, —C(=O)—, —(C(=O)O)—, —(C(=O)NR$^e$)—, —N(R$^e$)C(=O)—, or —($C_{1-4}$ alkylene)-;

$G_1$ and $G_2$ are each independently, at each occurrence, —($C_{6-14}$ arylene)-;

$G_3$ is H, $C_{1-6}$ alkyl, $C_{3-7}$ cycloalkyl, $C_{3-10}$ heterocycloalkyl, $C_{6-14}$ aryl, 5- to 14-membered heteroarylene, ($C_{1-4}$ alkylene)-($C_{1-4}$ heteroalkyl), ($C_{3-10}$ heterocycloalkylene)-($C_{1-4}$ alkyl), ($C_{3-10}$ heterocycloalkylene)-($C_{1-4}$ heteroalkyl);

$R^a$, $R^b$, $R^c$, $R^d$, and $R^e$ are each independently, at each occurrence, H or $C_{1-6}$ alkyl; and n is 1 or 2.

In one embodiment of Formula VIII, $R_4$ is H or $C_{1-6}$ alkyl; and $R_5$ is H, $C_{1-6}$ alkyl, —($C_{1-4}$ alkylene)-OR$^d$, —($C_{1-4}$ alkylene)-N(R$^d$)$_2$, or —($C_{1-4}$ alkylene)-S(=O)$_2$—(R$^d$).

In one embodiment, each $R_5$ is H, $C_{1-6}$ alkyl, —($C_{0-4}$ alkylene)-OR$^f$, —($C_{0-4}$ alkylene)-N(R$^f$)$_2$, —($C_{0-4}$ alkylene)-S(=O)$_2$—(R$^f$), —($C_{0-4}$ alkylene)-($C_{6-14}$ aryl), —($C_{1-4}$ alkylene)-(5- to 14-membered heteroaryl), —($C_{0-4}$ alkylene)-C(=O)NR$^b$R$^f$ or —($C_{0-4}$ alkylene)-NR$^b$C(=O)R$^f$.

In another embodiment of Formula VIII, $R_4$ is OH, and Z is O. In still another embodiment of Formula VIII, $R_1$ is —OH;
$R_2$ is H or $C_{1-6}$ alkyl;
$R_3$ is H or $C_{1-6}$ alkyl;
Z is O;
$L_1$ is a bond;
$L_2$ is a bivalent radical is selected from —(C(R$_4$)(R$_5$))$_n$ ($C_{0-3}$ alkylene), or —C(R$_4$)(R$_5$)$_n$—($C_{0-3}$ alkylene)-N(R$_5$)—;

wherein $R_4$ is H or $C_{1-6}$ alkyl;
$R_5$ is H or $C_{1-6}$ alkyl;
$L_3$ is a bivalent radical selected from —($C_{2-6}$ alkenylene)-, or —($C_{2-6}$ alkynylene)-;
$L_4$ is a bivalent radical selected from a bond, —C(=O)—, —(C(=O)O)—, —(C(=O)NR$^e$)—, —N(R$^e$)C(=O)—, or —($C_{1-4}$ alkylene)-;

$G_1$ and $G_2$ are each independently, at each occurrence, a bivalent radical selected from —($C_{6-14}$ arylene)- or -(5- to 14-membered heteroarylene)-;

$G_3$ is H, $C_{1-6}$ alkyl, $C_{3-7}$ cycloalkyl, $C_{3-10}$ heterocycloalkyl, $C_{6-14}$ aryl, 5- to 14-membered heteroarylene, ($C_{1-4}$ alkylene)-($C_{1-4}$ heteroalkyl), ($C_{3-10}$ heterocycloalkylene)-($C_{1-4}$ alkyl), ($C_{3-10}$ heterocycloalkylene)-($C_{1-4}$ heteroalkyl);

R$^c$ and R$^e$ are each independently, at each occurrence, H or $C_{1-6}$ alkyl; and n is 1 or 2.

In yet another embodiment of Formula VIII, $L_2$ is a bivalent radical selected from —(C(R$_4$)(R$_5$)$_n$)—($C_{0-3}$ alkylene)-(C(=O)NR$_5$)—, —(C(R$_4$)(R$_5$))$_n$—($C_{0-3}$ alkylene)-N(R$_5$)C(=O)—, or —C(R$_4$)(R$_5$)$_n$—($C_{0-3}$ alkylene)-N(R$_5$)—;

$L_3$ is a bivalent radical —($C_{2-6}$ alkynylene)-;
$L_4$ is a bivalent radical selected from a bond, —C(=O)—, —(C(=O)O)—, —(C(=O)NR$^e$)—, —N(R$^e$)C(=O)—, or —($C_{1-4}$ alkylene)-;

$G_1$ and $G_2$ are each independently, at each occurrence, a bivalent radical selected from —($C_6$ arylene)- or -(5- to 6-membered heteroarylene)-; and $G_3$ is H, $C_{1-6}$ alkyl, $C_{3-7}$ cycloalkyl, $C_{3-10}$ heterocycloalkyl, 5- to 6-membered heteroarylene, ($C_{1-4}$ alkylene)-($C_{1-4}$ heteroalkyl), ($C_{3-10}$ heterocycloalkylene)-($C_{1-4}$ alkyl), ($C_{3-10}$ heterocycloalkylene)-($C_{1-4}$ heteroalkyl).

In one embodiment, $L_2$ is —(C(R$_4$)(R$_5$))$_n$—($C_{0-3}$ alkylene)-, —(C(R$_4$)(R$_5$))$_n$—$C_{0-3}$ alkylene)-(C—OR$^c$)—, or —(C(R$_4$)(R$_5$))$_n$—($C_{0-3}$ alkylene)-N(R$_5$)—. In another embodiment, $L_2$ is —(C(R$_4$)(R$_5$))$_n$—($C_{0-3}$ alkylene)- or —(C(R$_4$)(R$_5$))$_n$—$C_{0-3}$ alkylene)-(C—OR$^c$)—.

In one embodiment, $L_3$ is —($C_{2-4}$ alkynylene)-. In another embodiment, $L_3$ is —($C_2$ alkynylene)-. In another embodiment, $L_3$ is —($C_4$ alkynylene)-.

In one embodiment, $L_4$ is a bond, —C(=O)—, —(C(=O)O)—, —(C(=O)NR$^e$)—, or —($C_{1-4}$ alkylene)-. In one embodiment, $L_4$ is a bond, —(C(=O)NR$^e$)—, or —($C_{1-4}$ alkylene)-. In one embodiment, $L_4$ is a bond. In one embodiment, $L_4$ is —(C(=O)NR$^e$)—. In one embodiment, $L_4$ is —($C_{1-4}$ alkylene)-.

In one embodiment, $G_1$ and $G_2$ are each —($C_6$ arylene)-. In another embodiment, $G_1$ and $G_2$ are each phenyl.

In one embodiment, $G_3$ is $C_{1-6}$ alkyl, $C_{3-7}$ cycloalkyl, $C_{3-10}$ heterocycloalkyl, 5- to 6-membered heteroarylene, ($C_{1-4}$ alkylene)-($C_{1-4}$ heteroalkyl), ($C_{3-10}$ heterocycloalkylene)-($C_{1-4}$ alkyl), or ($C_{3-10}$ heterocycloalkylene)-($C_{1-4}$ heteroalkyl). In one embodiment, $G_3$ is $C_{2-6}$ alkyl, $C_{3-7}$ cycloalkyl, $C_{3-10}$ heterocycloalkyl, 5- to 6-membered heteroarylene, ($C_{1-4}$ alkylene)-($C_{1-4}$ heteroalkyl), ($C_{3-10}$ heterocycloalkylene)-($C_{1-4}$ alkyl), or ($C_{3-10}$ heterocycloalkylene)-($C_{1-4}$ heteroalkyl). In one embodiment, $G_3$ is $C_{3-7}$ cycloalkyl, $C_{3-10}$ heterocycloalkyl, ($C_{1-4}$ alkylene)-($C_{1-4}$ heteroalkyl), ($C_{3-10}$ heterocycloalkylene)-($C_{1-4}$ alkyl), or ($C_{3-10}$ heterocycloalkylene)-($C_{1-4}$ heteroalkyl). In one embodiment, $G_3$ is $C_{3-10}$ heterocycloalkyl, ($C_{1-4}$ alkylene)-($C_{1-4}$ heteroalkyl), ($C_{3-10}$ heterocycloalkylene)-($C_{1-4}$ alkyl), or ($C_{3-10}$ heterocycloalkylene)-($C_{1-4}$ heteroalkyl).

Some embodiments provided herein describe a compound of Formula VIII having the structure of Formula VIIIA:

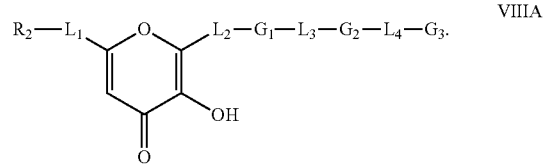

VIIIA

Some embodiments provided herein describe a compound of Formula VIII having the structure of Formula VIIIB:

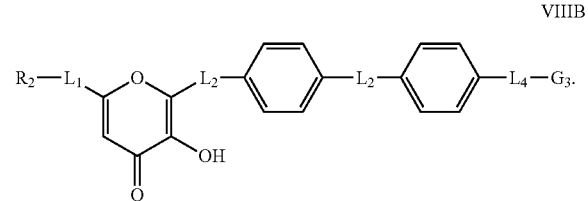

VIIIB

Some embodiments provided herein describe a compound of Formula VIII having the structure of Formula VIIIC:

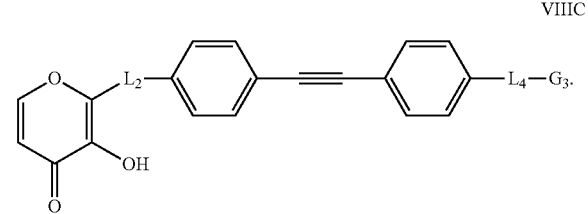

VIIIC

Some embodiments provided herein describe a compound of Formula VIII having the structure of Formula VIIID:

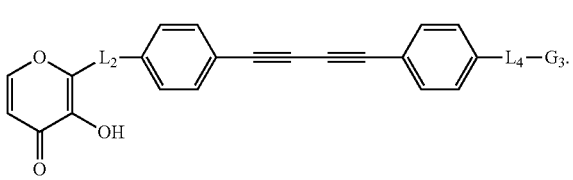

VIIID

In a further aspect, the disclosure provides a compound having the following structural formula

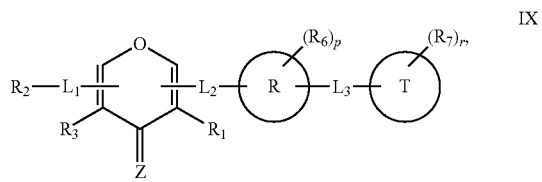

IX or a pharmaceutically acceptable salt thereof,
wherein:
$R_1$ is H, $C_{1-6}$ alkyl, —OH, —NH$_2$, or SH;
$R_2$ is H, —OR$^a$, $C_{1-6}$ alkyl, or $C_{1-6}$ alkoxy;
$R_3$ is H, $C_{1-6}$ alkyl, —OH, —NH$_2$, or SH;
$R_6$ and $R_7$ are each independently, at each occurrence, —OH, —NH$_2$, —CN, —NO$_2$, —C(=O)OR$^b$, —C(=O)N(R$^b$)$_2$, —N(R$^b$)C(=O)OR$^b$, halo, $C_{1-6}$ alkyl, $C_{1-6}$ alkoxy, or =O;
ring R is $C_{3-7}$ cycloalkyl, $C_{3-10}$ heterocycloalkyl, $C_{6-14}$ aryl, or a 5- to 14-membered heteroaryl;
ring T is $C_{3-7}$ cycloalkyl, $C_{3-10}$ heterocycloalkyl, $C_{6-14}$ aryl, or a 5- to 14-membered heteroaryl;
Z is O or S;
$L_1$ is a bivalent radical selected from a bond, —C(=O)—, —(C(=O)O)—, —OC(=O)—, —C(=O)NR$^c$—, —N(R$^c$)C(=O)—, —N(R$^c$)—, —S(=O)$_2$—, —(C$_{1-4}$ alkylene)-, —(C$_{1-4}$ alkylene)-O—, —(C$_{1-4}$ alkylene)-N(R$^e$)—, —(C$_{1-4}$ alkylene)-S—, or —(C$_{1-4}$ alkylene)-S(=O)$_2$—;
$L_2$ is a bivalent radical selected from —(C(R$_4$)(R$_5$))$_n$—(C$_{0-3}$ alkylene)-, —(C(R$_4$)(R$_5$))$_n$—C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-C(=O)NR$_5$)—, —(C(R$_4$)(R$_5$))$_n$—(C$_{0-3}$ alkylene)-N(R$_5$)C(=O)—, —(C(R$_4$)(R$_5$))$_n$—(C$_{0-3}$ alkylene)-O—, or —(C(R$_4$)(R$_5$))$_n$(C$_{0-3}$ alkylene)-N(R$_5$)—;
wherein each $R_4$ is H or optionally substituted $C_{1-6}$ alkyl; and
each $R_5$ is independently H, an optionally substituted $C_{1-6}$ alkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —(C$_{0-4}$ alkylene)-OR$^f$, —(C$_{0-4}$ alkylene)-(C$_{1-4}$ alkene), —(C$_{0-4}$ alkylene)-(C$_{1-4}$ alkyne), $C_2$-$C_7$ heterocycle, —(C$_{0-4}$ alkylene)-C(=O)—(C$_1$-$C_6$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene)-N(R$^f$)$_2$, —(C$_{0-4}$ alkylene)-S(=O)$_2$—(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)-C(=O)NR$^b$R$^f$ or —(C$_{0-4}$ alkylene)-NR$^b$C(=O)R$^f$;

wherein each R$^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;
$L_3$ is a bivalent radical selected from a bond, —(C$_{1-6}$ alkylene)-, —(C$_{2-6}$ alkenylene)-, or —(C$_{2-6}$ alkynylene)-, —(C$_{3-10}$ heterocycloalkylene)-, —(C$_{6-14}$ arylene)-, -(5- to 14-membered heteroarylene)-;
R$^a$, R$^b$, R$^c$, R$^d$, and R$^e$ are each independently, at each occurrence, H or C$_{1-6}$ alkyl;
n is 1 or 2;
p is 0, 1, 2, or 3; and
r is 0, 1, 2, or 3,
provided that $R_1$ or $R_3$ is —OH, —NH$_2$, or SH.
In one embodiment of Formula IX, $R_4$ is H or C$_{1-6}$ alkyl; and $R_5$ is H, C$_{1-6}$ alkyl, —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), or —(C$_{1-4}$ alkylene)-(5- to 14-membered heteroaryl).
In one embodiment, each $R_5$ is H, C$_{1-6}$ alkyl, —(C$_{0-4}$ alkylene)-OR$^f$, —(C$_{0-4}$ alkylene)-N(R$^f$)$_2$, —(C$_{0-4}$ alkylene)-S(=O)$_2$—(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)-C(=O)NR$^b$R$^f$ or —(C$_{0-4}$ alkylene)-NR$^b$C(=O)R$^f$.
In some embodiments of Formula IX, Z is O. In another embodiment of Formula IX, Z is S. In yet another embodiment, $L_1$ bivalent radical selected from a bond, —(C$_{1-4}$ alkylene)-O—, —(C$_{1-4}$ alkylene)-N(R$^b$)—, —(C$_{1-4}$ alkylene)-S—, or —(C$_{1-4}$ alkylene)-S(=O)$_2$—; $R_2$ is H, —OR$^a$, —N(R$^a$)$_2$, C$_{1-6}$ alkyl, or C$_{1-6}$ alkoxy; and R$^b$ is H or C$_{1-6}$ alkyl. In one embodiment, $R_5$ is not hydrogen. In another embodiment, $R_5$ is —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), or —(C$_{1-4}$ alkylene)-(5- to 14-membered heteroaryl). In certain embodiments, $R_5$ is —(C$_{1-4}$ alkylene)-OR$^d$, —(C$_{1-4}$ alkylene)-N(R$^d$)$_2$, or —(C$_{1-4}$ alkylene)-S(=O)$_2$—(R$^d$). In one embodiment, $L_1$ is a bond and $R_5$ is hydrogen. In yet another embodiment, $L_3$ is a bivalent radical selected from —(C$_{2-6}$ alkenylene)-, —(C$_{2-6}$ alkynylene)-, —(C$_{3-10}$ heterocycloalkylene)-, —(C$_{6-14}$ arylene)-, or -(5- to 14-membered heteroarylene)-. In still another embodiment, $L_3$ is a bond. In another embodiment, $L_3$ is —(C$_{2-6}$ alkynylene)-. In yet another embodiment, p is 1, and $R_6$ is =O. In a further embodiment, ring R with one $R_6$ substituent forms a pyridinone ring (p is 1, and $R_6$ is =O). In some embodiments, ring R with one $R_6$ substituent forms a 2-pyridinone ring.
In one embodiment, $L_2$ is —(C(R$_4$)(R$_5$))$_n$—(C$_{0-3}$ alkylene)-, —(C(R$_4$)(R$_5$))$_n$—C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-C(=O)NR$_5$)—, —(C(R$_4$)(R$_5$))$_n$—(C$_{0-3}$ alkylene)-N(R$_5$)C(=O)—, —(C(R$_4$)(R$_5$))—(C$_{0-3}$ alkylene)-O—, or —(C(R$_4$)(R$_5$))$_n$—(C$_{0-3}$ alkylene)-N(R$_5$)—. In one embodiment, $L_2$ is —(C(R$_4$)(R$_5$))$_n$—(C$_{0-3}$ alkylene)-, —(C(R$_4$)(R$_5$))$_n$—C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=O)NR$_5$)—, —(C(R$_4$)(R$_5$))$_n$—(C$_{0-3}$ alkylene)-N(R$_5$)C(=O)—, —(C(R$_4$)(R$_5$))$_n$—(C$_{0-3}$ alkylene)-O—, or —(C(R$_4$)(R$_5$))$_n$—(C$_{0-3}$ alkylene)-N(R$_5$)—. In one embodiment, $L_2$ is —(C(R$_4$)(R$_5$))$_n$(C$_{0-3}$ alkylene)-, —(C(R$_4$)(R$_5$))$_n$—(C$_{0-3}$ alkylene)-(C(=O)NR$_5$)—, (C(R$_4$)(R$_5$))$_n$—(C$_{0-3}$ alkylene)-N(R$_5$)C(=O)—, —(C(R$_4$)(R$_5$))$_n$—(C$_{0-3}$ alkylene)-O—, or —(C(R$_4$)(R$_5$))$_n$—(C$_{0-3}$ alkylene)-N ($R_5$)—. In one embodiment, $L_2$ is —(C($R_4$)($R_5$))$_n$—($C_{0-3}$ alkylene)-, —(C($R_4$)($R_5$))$_n$—($C_{0-3}$ alkylene)-O—, or —(C($R_4$)($R_5$))—($C_{0-3}$ alkylene)-N($R_5$)—. In one embodiment, $L_2$ is —(C($R_4$)($R_5$))$_n$—($C_{0-3}$ alkylene)- or —(C($R_4$)($R_5$))$_n$—($C_{0-3}$ alkylene)-O—. In one embodiment, $L_2$ is —(C($R_4$)($R_5$))$_n$($C_{0-3}$ alkylene)-. In another embodiment, $L_2$ is —(C($R_4$)($R_5$))$_n$—($C_{0-3}$ alkylene)-O—.

Some embodiments provided herein describe a compound of formula IX wherein:

$R_1$ is —OH;
$R_2$ is H;
$R_3$ is H;
ring R is $C_{6-14}$ aryl;
ring T is $C_{6-14}$ aryl;
Z is O;
$L_1$ is a bond;
$L_2$ is —(C($R_4$)($R_5$))$_n$—($C_{0-3}$ alkylene)-, —(C($R_4$)($R_5$))$_n$—$C_{0-3}$ alkylene)-(C—O$R^c$)—, —(C($R_4$)($R_5$))$_n$($C_{0-3}$ alkylene)-C(=O)—, —(C($R_4$)($R_5$))$_n$—($C_{0-3}$ alkylene)-C(=N—OH)—, —(C($R_4$)($R_5$))$_n$—($C_{0-3}$ alkylene)-(C(=O)NR$_5$)—, —(C($R_4$)($R_5$))$_n$—($C_{0-3}$ alkylene)-N($R_5$)C(=O)—, —(C($R_4$)($R_5$))$_n$—($C_{0-3}$ alkylene)-O—, or —(C($R_4$)($R_5$))$_n$—($C_{0-3}$ alkylene)-N($R_5$)—;

wherein each $R_4$ is H or optionally substituted $C_{1-6}$ alkyl; and each $R_5$ is independently H, an optionally substituted $C_{1-6}$ alkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —($C_{0-4}$ alkylene)-O$R^f$, —($C_{0-4}$ alkylene)-($C_{1-4}$ alkene), —($C_{0-4}$ alkylene)-($C_{1-4}$ alkyne), $C_2$-$C_7$ heterocycle, —($C_{0-4}$ alkylene)-C(=O)—($C_1$-$C_6$ alkyl), —($C_{0-4}$ alkylene)-C(=O)H, —($C_{0-4}$ alkylene)-C(=O)O$R^f$, —($C_{0-4}$ alkylene)-CN, —($C_{0-4}$ alkylene)-halo, —($C_{0-4}$ alkylene)-NO$_2$, —($C_{0-4}$ alkylene)-N($R^f$)$_2$, —($C_{0-4}$ alkylene)-S(=O)$_2$—($R^f$), —($C_{0-4}$ alkylene)-($C_{6-14}$ aryl), —($C_{1-4}$ alkylene)-(5- to 14-membered heteroaryl), —($C_{0-4}$ alkylene)-C(=O)NR$^b$R$^f$ or —($C_{0-4}$ alkylene)-NR$^b$C(=O)R$^f$;

wherein each $R^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$L_3$ is a bivalent radical selected from a bond, or —($C_{2-6}$ alkynylene)-;

$R^b$ and $R^c$ are each independently, at each occurrence, H or $C_{1-6}$ alkyl; and n is 1 or 2.

In yet another aspect, the disclosure provides compounds having the structural formulas provided in Table 1.

TABLE 1

Select compounds of the disclosure.

| Compound ID | Structure |
|---|---|
| 1 | 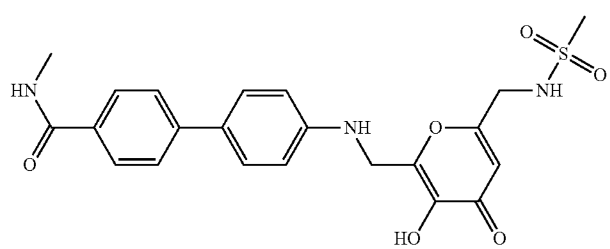 |
| 2 | 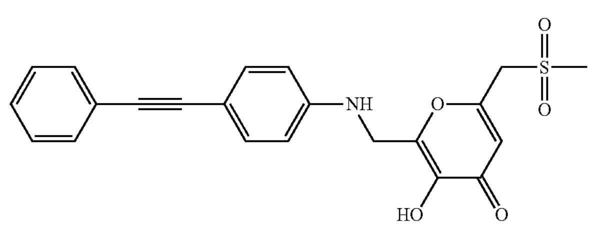 [SMILES: CS(=O)(=O)Cc1cc(=O)c(O)c(CNc2ccc(C#Cc3ccccc3)cc2)o1] |
| 3 | 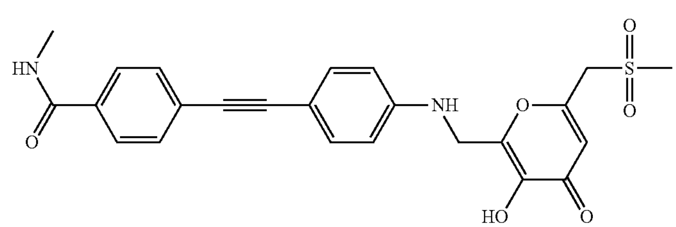 [SMILES: CNC(=O)c1ccc(C#Cc2ccc(NCc3oc(CS(C)(=O)=O)cc(=O)c3O)cc2)cc1] |

TABLE 1-continued

Select compounds of the disclosure.

| Compound ID | Structure |
|---|---|
| 4 | 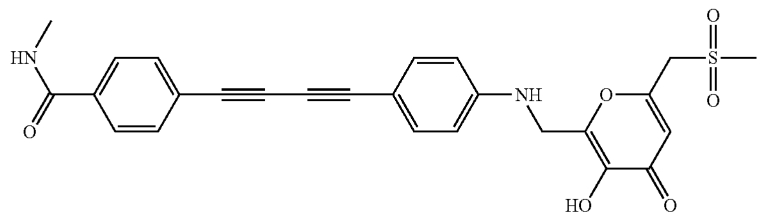 [SMILES: CNC(=O)c1ccc(C#CC#Cc2ccc(NCc3oc(CS(C)(=O)=O)cc(=O)c3O)cc2)cc1] |
| 5 | 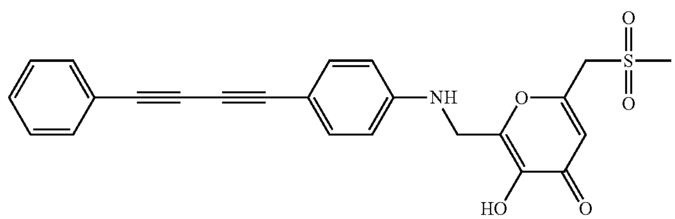 [SMILES: CS(=O)(=O)Cc1cc(=O)c(O)c(CNc2ccc(C#CC#Cc3ccccc3)cc2)o1] |
| 6 | 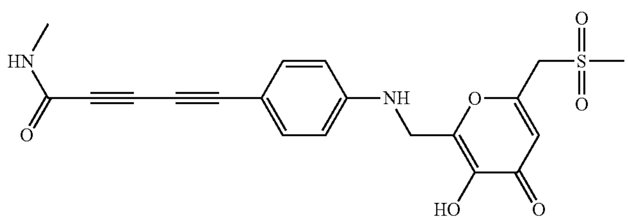 [SMILES: CNC(=O)C#CC#Cc1ccc(NCc2oc(CS(C)(=O)=O)cc(=O)c2O)cc1] |
| 7 | 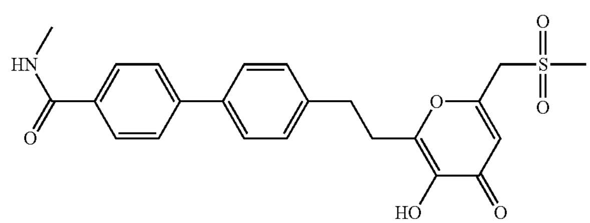 [SMILES: CNC(=O)c1ccc(-c2ccc(OCc3oc(CS(C)(=O)=O)cc(=O)c3O)cc2)cc1] |
| 8 | 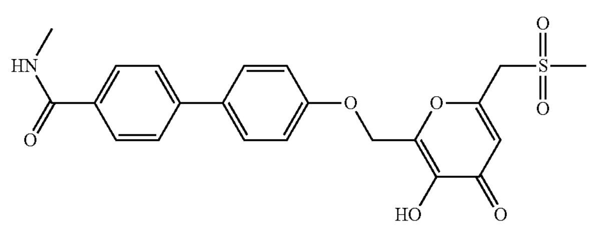 |
| 9 | 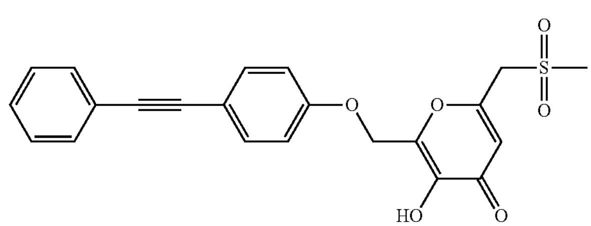 [SMILES: CS(=O)(=O)Cc1cc(=O)c(O)c(COc2ccc(C#Cc3ccccc3)cc2)o1] |
| 10 | 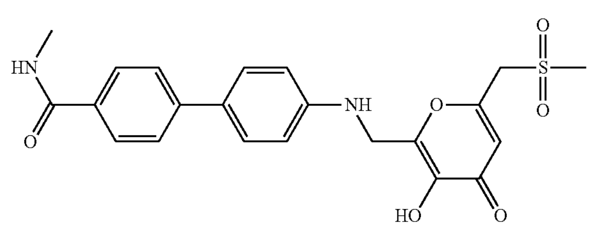 |

TABLE 1-continued

Select compounds of the disclosure.

| Compound ID | Structure |
|---|---|
| 11 | 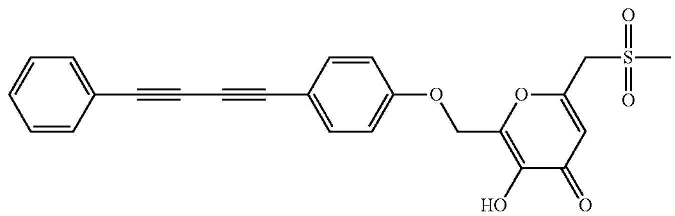 [SMILES: CS(=O)(=O)Cc1cc(=O)c(O)c(COc2ccc(C#CC#Cc3ccccc3)cc2)o1] |
| 12 | 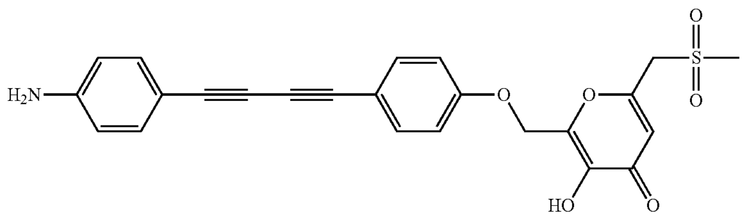 [SMILES: CS(=O)(=O)Cc1cc(=O)c(O)c(COc2ccc(C#CC#Cc3ccc(N)cc3)cc2)o1] |
| 13 | 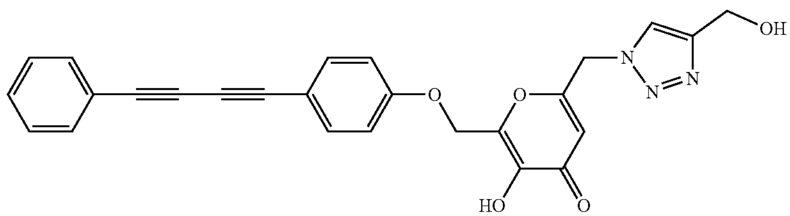 [SMILES: O=c1cc(Cn2cc(CO)nn2)oc(COc2ccc(C#CC#Cc3ccccc3)cc2)c1O] |
| 14 | 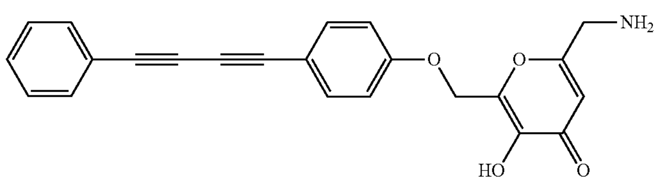 [SMILES: NCc1cc(=O)c(O)c(COc2ccc(C#CC#Cc3ccccc3)cc2)o1] |
| 15 | 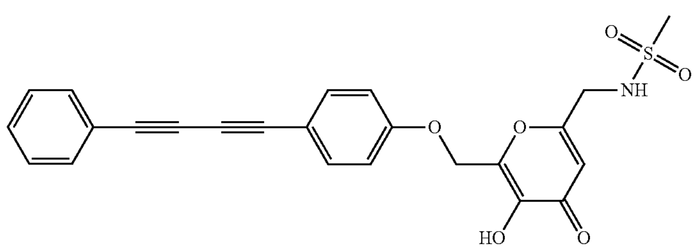 [SMILES: CS(=O)(=O)NCc1cc(=O)c(O)c(COc2ccc(C#CC#Cc3ccccc3)cc2)o1] |
| 16 | 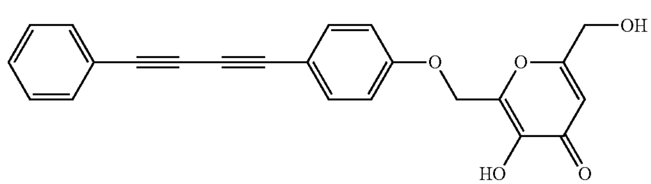 [SMILES: O=c1cc(CO)oc(COc2ccc(C#CC#Cc3ccccc3)cc2)c1O] |
| 17 | 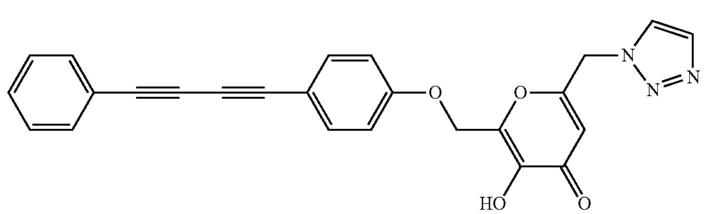 [SMILES: O=c1cc(Cn2ccnn2)oc(COc2ccc(C#CC#Cc3ccccc3)cc2)c1O] |

TABLE 1-continued

Select compounds of the disclosure.

| Compound ID | Structure |
| --- | --- |
| 18 | 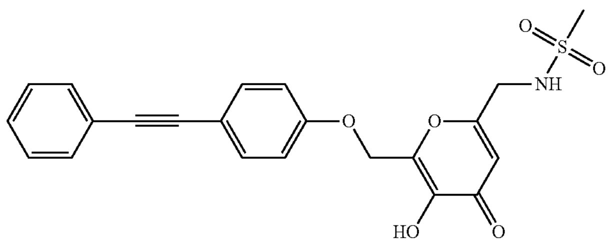 [SMILES: CS(=O)(=O)NCc1cc(=O)c(O)c(COc2ccc(C#Cc3ccccc3)cc2)o1] |
| 19 | 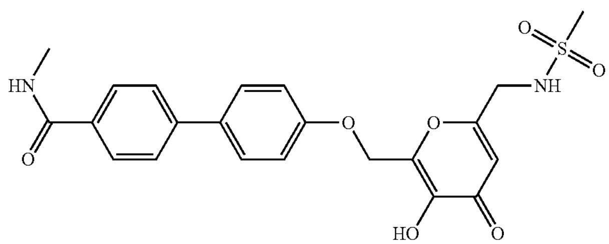 [SMILES: CNC(=O)c1ccc(-c2ccc(OCc3oc(CNS(C)(=O)=O)cc(=O)c3O)cc2)cc1] |
| 20 | 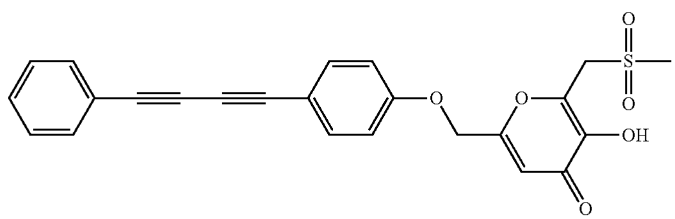 [SMILES: CS(=O)(=O)Cc1oc(COc2ccc(C#CC#Cc3ccccc3)cc2)cc(=O)c1O] |
| 21 | 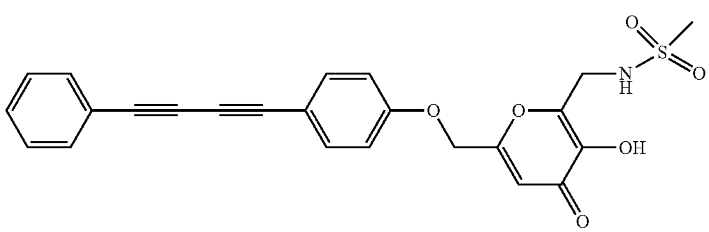 [SMILES: CS(=O)(=O)NCc1oc(COc2ccc(C#CC#Cc3ccccc3)cc2)cc(=O)c1O] |
| 22 | 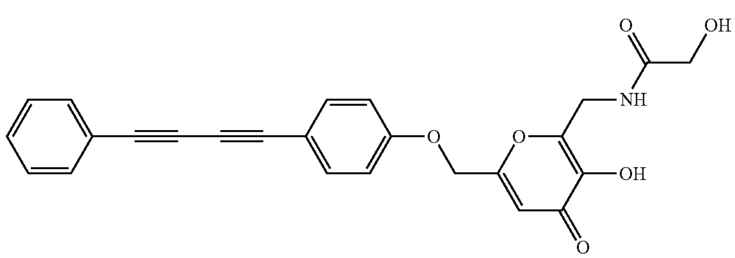 [SMILES: O=C(CO)NCc1oc(COc2ccc(C#CC#Cc3ccccc3)cc2)cc(=O)c1O] |
| 23 | 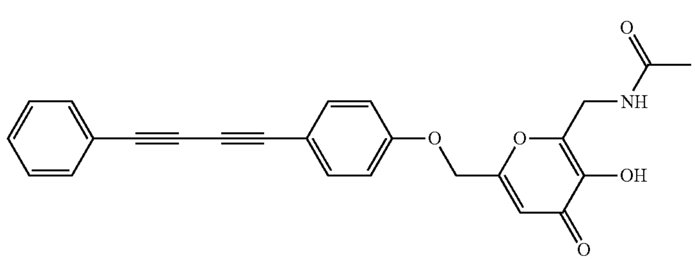 [SMILES: CC(=O)NCc1oc(COc2ccc(C#CC#Cc3ccccc3)cc2)cc(=O)c1O] |

TABLE 1-continued
Select compounds of the disclosure.
| Compound ID | Structure |
|---|---|
| 24 | 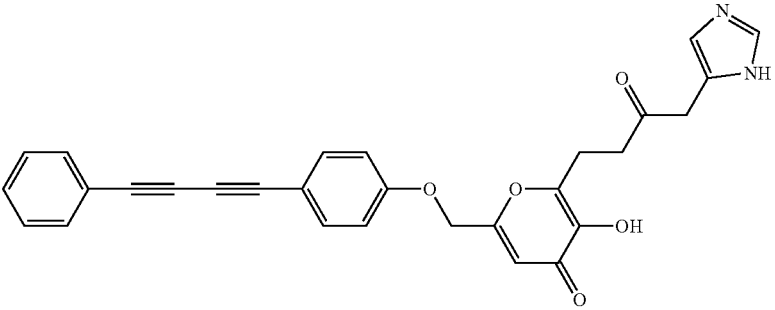 [SMILES: O=C(CCc1oc(COc2ccc(C#CC#Cc3ccccc3)cc2)cc(=O)c1O)Cc1cnc[nH]1] |
| 25 | 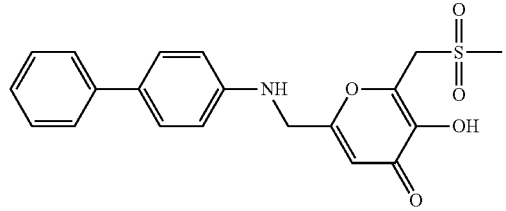 [SMILES: CS(=O)(=O)Cc1oc(CNc2ccc(-c3ccccc3)cc2)cc(=O)c1O] |
| 26 | 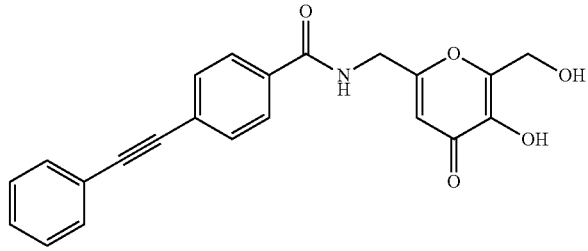 [SMILES: O=C(NCc1cc(=O)c(O)c(CO)o1)c1ccc(C#Cc2ccccc2)cc1] |
| 27 | 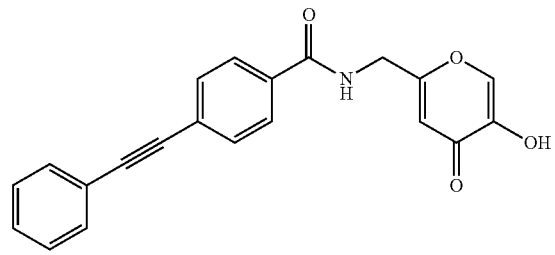 [SMILES: O=C(NCc1cc(=O)c(O)co1)c1ccc(C#Cc2ccccc2)cc1] |
| 28 | 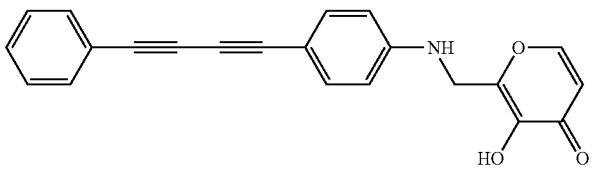 |
| 29 | 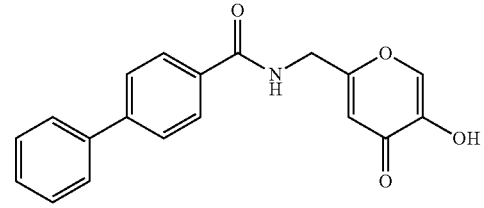 [SMILES: O=C(NCc1cc(=O)c(O)co1)c1ccc(-c2ccccc2)cc1] |

TABLE 1-continued

Select compounds of the disclosure.

| Compound ID | Structure |
|---|---|
| 30 | 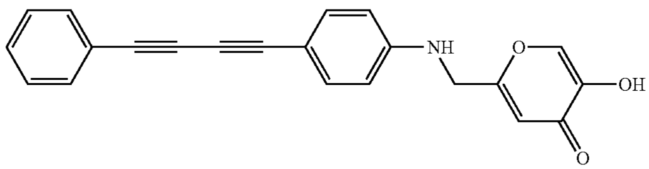 [SMILES: O=c1cc(CNc2ccc(C#CC#Cc3ccccc3)cc2)occ1O] |
| 31 | 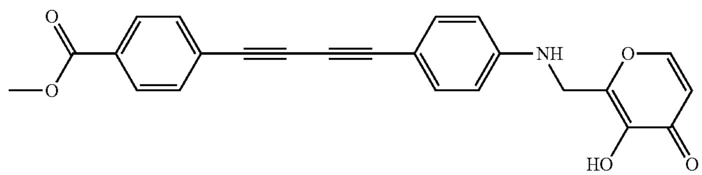 |
| 32 | 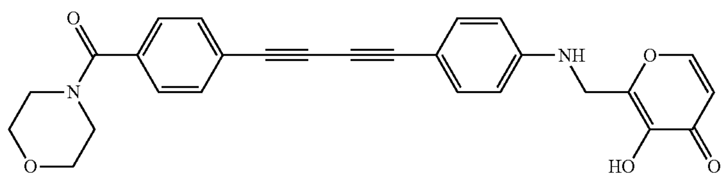 |
| 33 | 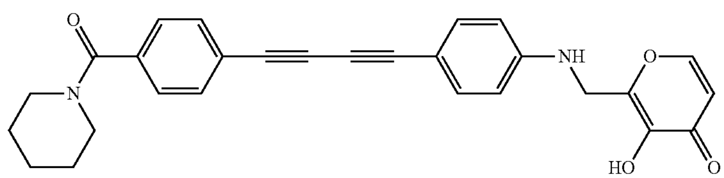 [SMILES: O=C(c1ccc(C#CC#Cc2ccc(NCc3occc(=O)c3O)cc2)cc1)N1CCCCC1] |
| 34 | 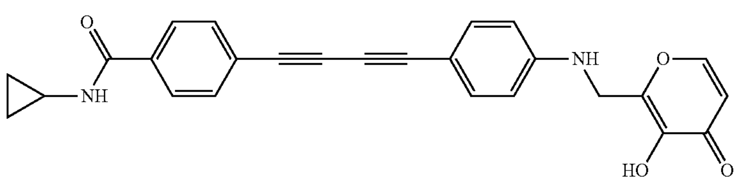 [SMILES: O=C(NC1CC1)c1ccc(C#CC#Cc2ccc(NCc3occc(=O)c3O)cc2)cc1] |
| 35 | 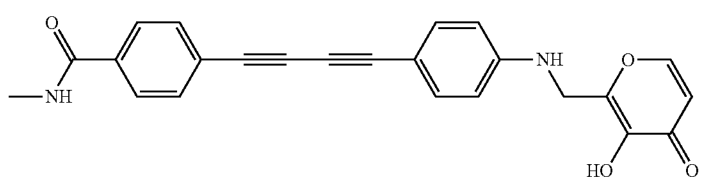 [SMILES: CNC(=O)c1ccc(C#CC#Cc2ccc(NCc3occc(=O)c3O)cc2)cc1] |
| 36 | 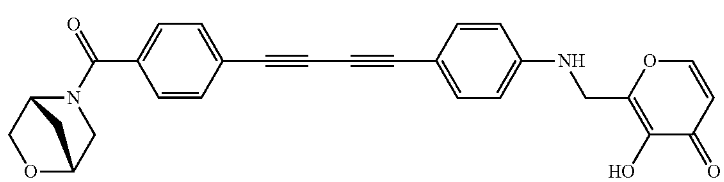 [SMILES: O=C(c1ccc(C#CC#Cc2ccc(NCc3occc(=O)c3O)cc2)cc1)N1C[C@H]2C[C@@H]1CO2] |
| 37 | 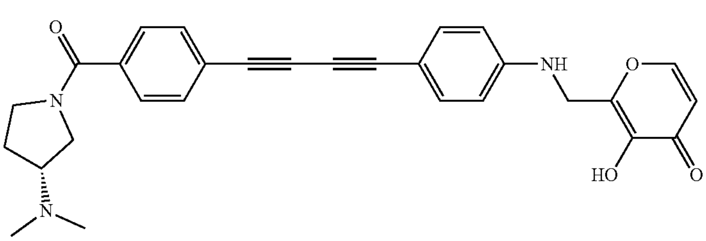 [SMILES: CN(C)[C@@H]1CCN(C(=O)c2ccc(C#CC#Cc3ccc(NCc4occc(=O)c4O)cc3)cc2)C1] |

TABLE 1-continued
Select compounds of the disclosure.
| Compound ID | Structure |
|---|---|
| 38 | 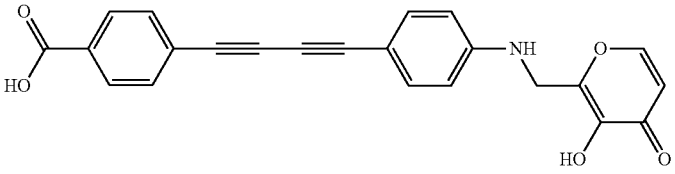 |
| 39 | 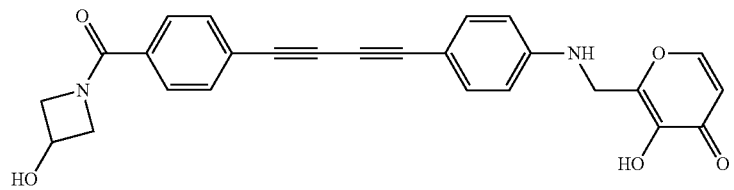 |
| 40 | 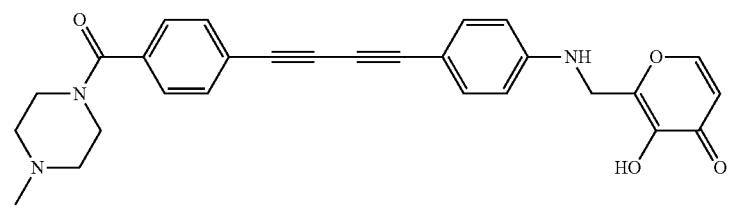 [SMILES: CN1CCN(C(=O)c2ccc(C#CC#Cc3ccc(NCc4occc(=O)c4O)cc3)cc2)CC1] |
| 41 | 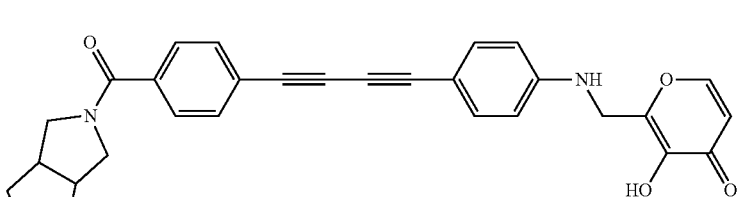 |
| 42 | 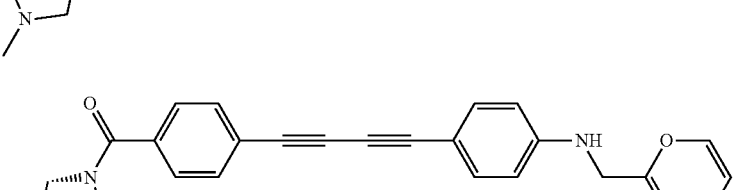 |
| 43 | 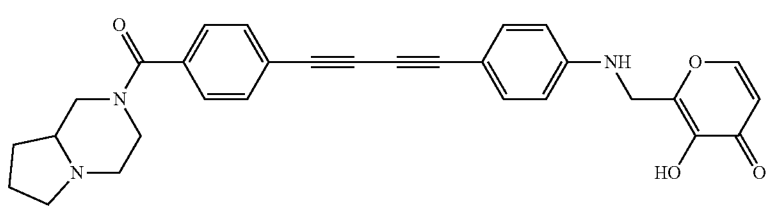 [SMILES: O=C(c1ccc(C#CC#Cc2ccc(NCc3occc(=O)c3O)cc2)cc1)N1CCN2CCCC2C1] |
| 44 | 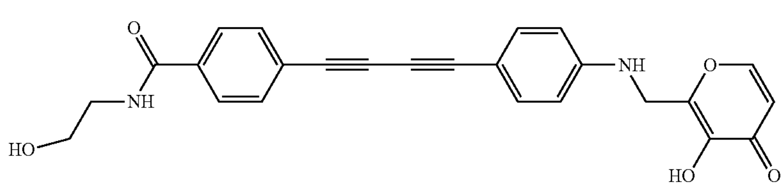 [SMILES: O=C(NCCO)c1ccc(C#CC#Cc2ccc(NCc3occc(=O)c3O)cc2)cc1] |

TABLE 1-continued

Select compounds of the disclosure.

| Compound ID | Structure |
|---|---|
| 45 | *(structure)* |
| 46 | *(structure)* |
| 47 | *(structure)* |
| 48 | *(structure)* |
| 49 | *(structure)* |
| 50 | *(structure)* |
| 51 | *(structure)* |

TABLE 1-continued

Select compounds of the disclosure.

| Compound ID | Structure |
|---|---|
| 52 | 4-cyanophenyl-ethynyl-phenyl-NH-CH2-(3-hydroxy-4-oxo-4H-pyran-2-yl) |
| 53 | 4-carboxyphenyl-ethynyl-phenyl-NH-CH2-(3-hydroxy-4-oxo-4H-pyran-2-yl) |
| 54 | 4-(3-hydroxyazetidine-1-carbonyl)phenyl-ethynyl-phenyl-NH-CH2-(3-hydroxy-4-oxo-4H-pyran-2-yl) |
| 55 | 4-(morpholinomethyl)phenyl-ethynyl-phenyl-NH-CH2-(3-hydroxy-4-oxo-4H-pyran-2-yl) |
| 56 | 2-(1-([1,1'-biphenyl]-4-ylamino)but-3-en-1-yl)-3-hydroxy-4H-pyran-4-one |
| 57 | 2-(1-([1,1'-biphenyl]-4-ylamino)-3-hydroxypropyl)-3-hydroxy-4H-pyran-4-one |

TABLE 1-continued

Select compounds of the disclosure.

| Compound ID | Structure |
|---|---|
| 58 | 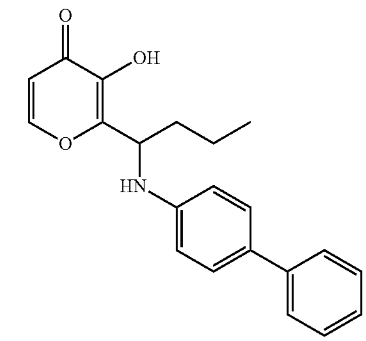 [SMILES: CCCC(Nc1ccc(-c2ccccc2)cc1)c1occc(=O)c1O] |
| 59 | 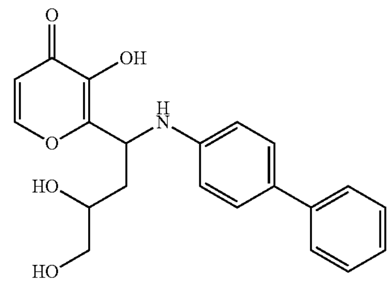 [SMILES: O=c1ccoc(C(CC(O)CO)Nc2ccc(-c3ccccc3)cc2)c1O] |
| 60 | 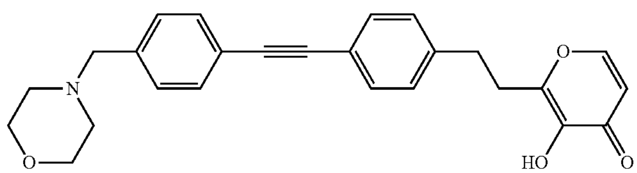 [SMILES: O=c1ccoc(CCc2ccc(C#Cc3ccc(CN4CCOCC4)cc3)cc2)c1O] |
| 61 | 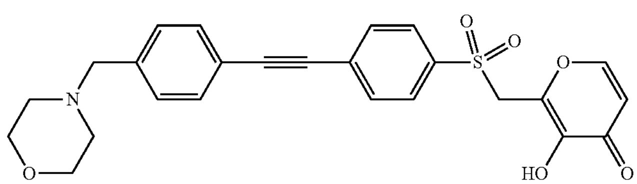 [SMILES: O=c1ccoc(CS(=O)(=O)c2ccc(C#Cc3ccc(CN4CCOCC4)cc3)cc2)c1O] |
| 62 | 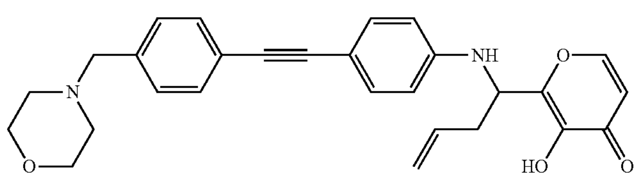 [SMILES: C=CCC(Nc1ccc(C#Cc2ccc(CN3CCOCC3)cc2)cc1)c1occc(=O)c1O] |

Pharmaceutical Compositions

As used herein the term "pharmaceutical composition" refers to a preparation of one or more of the components described herein, or pharmaceutically acceptable salts thereof, with other chemical components such as physiologically suitable carriers and excipients. The purpose of a pharmaceutical composition is to facilitate administration of a compound to a patient or subject.

The term "excipient" refers to an inert or inactive substance added to a pharmaceutical composition to further facilitate administration of a compound. Non-limiting examples of excipients include calcium carbonate, calcium phosphate, various sugars and types of starch, cellulose derivatives, gelatin, vegetable oils and polyethylene glycols.

The present teachings further comprise pharmaceutical compositions comprising one or more of the compounds of the present disclosure, and at least one pharmaceutically acceptable excipient.

In some embodiments, compositions are administered to humans, human patients or subjects. For the purposes of the present disclosure, the phrase "active ingredient" generally refers to a compound to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Subjects to which administration of the pharmaceutical compositions is contemplated include, but are not limited to, non-human mammals, including cattle, pigs, cats, dogs, mice, and rats.

Dosing

The present disclosure provides methods comprising administering compounds of the disclosure to a subject in need thereof. Metalloprotein modulator compounds as described herein may be administered to a subject using any amount and any route of administration effective for treating a disease, a disorder, or a condition (e.g., a disease, a disorder, or a condition relating to gram-negative bacterial infections).

Compositions in accordance with the disclosure are typically formulated in dosage unit form for ease of administration and uniformity of dosage. It will be understood, however, that the total daily usage of the compositions of the present disclosure may be decided by the attending physician within the scope of sound medical judgment. The specific therapeutically effective or prophylactically effective dose level for any particular subject will depend upon a variety of factors including the species, age, body weight, general health, sex and diet of the subject; the disorder or disease being treated and the severity of the disorder or disease; the activity of the specific compound employed; the specific composition employed; the time of administration, route of administration, and rate of excretion of the specific compound employed; the duration of the treatment; drugs used in combination or coincidental with the specific compound employed; and like factors well known in the medical arts.

Use of Metalloprotein Modulators

Metalloproteins influence a vast diversity of biological systems, biological processes, and diseases. For example, LpxC, a zinc-dependent deacetylase, catalyzes the first committed step in Lipid A biosynthesis. Lipid A is an essential component of the outer membrane of gram-negative bacteria. LpxC is highly conserved across strains of gram-negative bacteria. Therefore, inhibitors of LpxC may provide effective alternative antibacterial agents.

In another aspect, the disclosure provides a method of modulating the activity of a metalloprotein such as LpxC in a subject in need thereof comprising administering to the subject a metalloprotein modulator comprising a pyrone derivative. The pyrone will bind to the catalytic zinc(II) ion and inhibit LpxC. LpxC has been implicated in diseases including bacterial infection. In some embodiments, the gram-negative bacterial infection is a urinary tract infection, a hospital acquired/ventilator-associated pneumonia, or an intra-abdominal infection.

In another aspect, the disclosure provides a method for treating or ameliorating one or more diseases associated with a metalloprotein function or activity comprising administering a therapeutically effect amount of a metalloprotein modulator. In some embodiments, the metalloprotein modulator inhibits the activity of a metalloprotein, LpxC.

In another embodiment, the LpxC inhibitor is a compound of Formula VII, a compound of Formula VIII, or a compound of Formula IX.

In still another aspect, the disclosure provides a method of modulating the activity of LpxC in a subject in need thereof comprising administering a therapeutically effective amount of a compound of Formula VII, a compound of Formula VIII, a compound of Formula IX, or a pharmaceutically acceptable salt thereof.

In another embodiment, methods of treatment to treat or to ameliorate a gram-negative bacterial infection are provided. The compounds of the disclosure can be used for treating conditions caused by the bacterial production of endotoxin and, in particular, by gram-negative bacteria and bacteria that use LpxC in the biosynthesis of lipopolysaccharide (LPS) or endotoxin. In some embodiments, the method of treating a gram-negative bacterial infection in a subject comprises administering to the subject a pharmaceutical composition comprising a compound of Formula VII, a compound of Formula VIII, a compound of Formula IX, or a pharmaceutically acceptable salt thereof.

One embodiment provided herein describes the use of a compound of Formula VII, a compound of Formula VIII, a compound of Formula IX, or a pharmaceutically acceptable salt thereof in the manufacture of a medicament. Another embodiment provided herein describes a compound of Formula VII, a compound of Formula VIII, a compound of Formula IX, or a pharmaceutically acceptable salt thereof for use as a medicament. In some embodiments, the medicament is used for the treatment of a bacterial infection. In some embodiments, the medicament is used for the treatment of a gram-negative bacterial infection.

In yet another embodiment, the compounds of the disclosure also are useful in the treatment of patients suffering from or susceptible to pneumonia, sepsis, cystic fibrosis, intra-abdominal infection, skin infections or urinary tract infections.

In yet another embodiment, the compounds of the disclosure also are useful in the treatment of patients suffering from chronic urinary tract infections, complicated urinary tract infections, cystitis, pyelonephritis, urethritis, recurrent urinary tract infections, bladder infections, urethral infections or kidney infections. In some embodiments, the compounds described herein are used for the treatment of complicated urinary tract infections.

In another embodiment, the compounds of the disclosure also are useful in the treatment of patients suffering from chronic intra-abdominal infection, peritonitis, intra-abdominal abscesses, diverticulitis, appendicitis, antibiotic associated diarrhea or intra-abdominal sepsis. In certain embodiments, the compounds described herein are used for treating complicated intra-abdominal infection.

In some embodiments, the compounds of the disclosure also are useful in the treatment of patients suffering from hospital acquired pneumonia, ventilator associated pneumonia, healthcare-associated pneumonia, community-acquired pneumonia or nosocomial pneumonia. In certain embodiments, the compounds described herein are used for treating hospital acquired pneumonia and/or ventilator associated pneumonia.

In still another embodiment, the compounds of the disclosure also are useful in the conditions that are caused or exacerbated by the bacterial production of lipid A and LPS or endotoxin, such as sepsis, septic shock, systemic inflammation, localized inflammation, chronic obstructive pulmonary disease (COPD) and acute exacerbations of chronic bronchitis (AECB).

In other embodiments, the compounds of the disclosure can be used for the treatment of a serious or chronic respiratory tract infection or complicated urinary tract infections including serious lung and nosocomial infections such as those caused by *Enterobacter aerogenes, Enterobacter cloacae, Escherichia coli, Klebsiella pneumoniae, Klebsiella oxytoca, Proteus mirabilis, Serratia marcescens, Stenotrophomonas maltophilia, Pseudomonas aeruginosa, Burkholderia cepacia, Acinetobacter baumannii, Alcaligenes xylosoxidans, Flavobacterium meningosepticum, Providencia sluarlii* and *Citrobacter freundi, Haemophilus influenzae, Legionella* species, *Moraxella catarrhalis,*

*Enterobacter* species, *Acinetobacter* species, *Klebsiella* species, *Burkholderia* species and *Proteus* species, and infections caused by other bacterial species such as *Neisseria* species, *Shigella* species, *Salmonella* species, *Helicobacter pylori, Vibrionaceae* and *Bordetella* species as well as the infections caused by a *Brucella* species, *Francisella tularensis* and/or *Yersinia pestis*.

Kits and Devices

The disclosure provides a variety of kits for conveniently and effectively carrying out methods of the present disclosure. Typically kits will comprise sufficient amounts and components to allow a user to perform multiple treatments of a subject(s) or to perform multiple experiments. In another embodiment, the kit may contain a compound of Formula VII, a compound of Formula VIII, or a compound of Formula IX.

In additional embodiments, pharmaceutical kits are provided. The kit includes a sealed container approved for the storage of pharmaceutical compositions, the container containing one of the above-described pharmaceutical compositions. In some embodiments, the sealed container minimizes the contact of air with the ingredients, e.g. an airless bottle. In other embodiments, the sealed container is a sealed tube. An instruction for the use of the composition and the information about the composition are to be included in the kit.

The present disclosure provides for devices which may incorporate compounds of the present disclosure. These devices contain in a stable formulation available to be immediately delivered to a subject in need thereof, such as a human patient.

It will be appreciated that the following examples are intended to illustrate but not to limit the present disclosure. Various other examples and modifications of the foregoing description and examples will be apparent to a person skilled in the art after reading the disclosure without departing from the spirit and scope of the disclosure, and it is intended that all such examples or modifications be included within the scope of the appended claims. All publications and patents referenced herein are hereby incorporated by reference in their entirety.

EXAMPLES

Example 1: Synthesis of Compounds or Metalloprotein Modulators

The compounds or metalloprotein modulators of the present disclosure may be synthesized with standard synthetic methods. Those skilled in the art of organic synthesis will recognize various synthetic methodologies that may be used to prepare compounds or metalloprotein modulators of the present disclosure.

Unless otherwise noted, starting materials were purchased from commercial suppliers (e.g., Sigma-Aldrich, Chem-Bridge, and Acros Organics) and were used without further purification. All commercial materials were listed as 95% purity or greater. The purity of all synthesized compounds was determined to be ≥95% by HPLC. Flash silica gel chromatography was performed using silica gel 40-63 μm mesh. $^1$H and $^{13}$C NMR spectra were recorded on one of several Varian FT-NMR spectrometers, In the discussion above and in the examples below, the following abbreviations have the following meanings. If an abbreviation is not defined, it has its generally accepted meaning.

DIAD=diisopropyl azocarboxylate
DMF=dimethylformamide
DMA=dimethylacetamide
DMAP=dimethylaminopyridine
DMSO=dimethyl sulfoxide
MeTHF=2-methyltetrahydrofuran
HATU=1-[Bis(dimethylamino)methylene]-1H-1,2,3-triazolo[4,5-b]pyridinium 3-oxid hexafluorophosphate)
DIPEA=N,N-Diisopropylethylamine
CBZ=benzyloxycarbonyl
DCC=1,3-dicyclohexylcarbodiimide
EtOAc=ethyl acetate
EtO=ethoxy
MeOH=methanol
DCM=dichloromethane
HCl=hydrochloric acid
ACN=acetonitrile
LDA=lithium diisopropylamide
mCPBA=meta-chloroperbenzoic acid
MTBE=methyl tert butyl ether
CDMT=2-chloro-4,6-dimethoxy-1,3,5-triazine
TMS=trimethyl silyl
DME=dimethyl ether
IPA=isopropanol
Et$_2$O=diethyl ether
DEAD=diethyl azodicarboxylate
LiHMDS=lithium hexamethyldisilazide/lithium bis(trimethylsilyl)amide
Aq.=aqueous
bm=broad multiplet
BOC=tert-butoxycarbonyl
bd=broad doublet
bs=broad singlet
d=doublet
dd=doublet of doublets
dq=doublet of quartets
dt=doublet of triplets
eq.=equivalents
g=grams
h=hours
HPLC=high pressure liquid chromatography
UPLC=ultra performance liquid chromatography
m=multiplet
M=molar
M %=mole percent
max=maximum
meq=milliequivalent
mg=milligram
mL=milliliter
mm=millimeter
mmol=millimol
q=quartet
s=singlet
t or tr=triplet
TBS=tert-butyldimethylsilyl
TFA=trifluoroacetic acid
THF=tetrahydrofuran
TLC=thin layer chromatography
p-TLC=preparative thin layer chromatography
μL=microliter
N=normality
MS=mass spectrometry
rt=room temperature
Ac=acetate
NMP=1-methyl-2-pyrrolidinone
μL=microliter
J=coupling constant NMR=nuclear magnetic resonance
MHz=megahertz
Hz=hertz
m/z=mass to charge ratio
min=minutes
ppt=precipitate
sat.=saturated Synthesis of Compound 1

Figure 10:
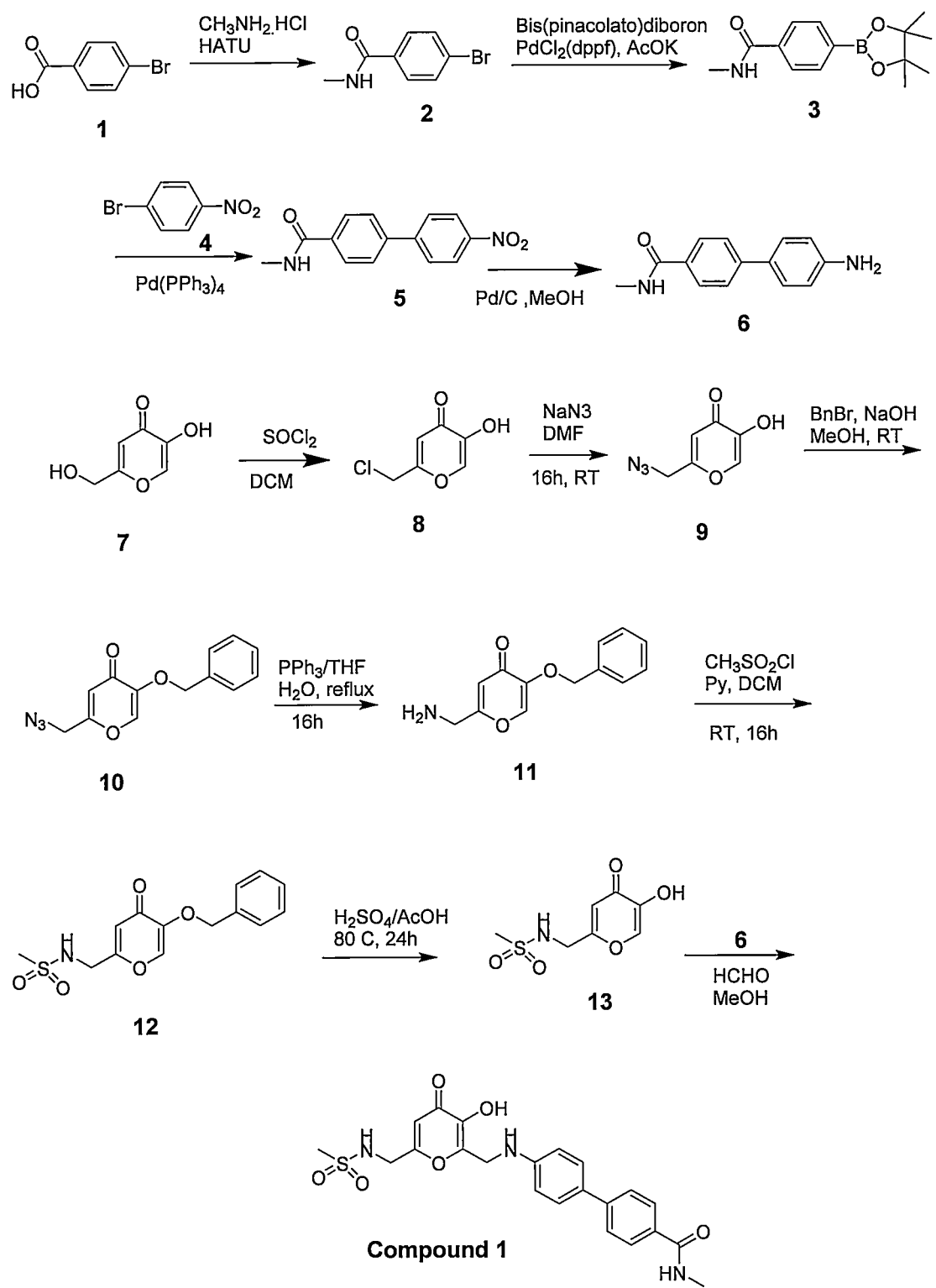
FIG. 10 shows a synthetic scheme to prepare compound 1.

The synthetic scheme to prepare compound 1 is shown in FIG. 10.

Synthesis of 4-bromo-N-methylbenzamide (2)

To a solution of 4-bromo benzoic acid (5 g, 0.0248 mol) in DMF (40 ml) was added HATU (11.3 g, 0.0297 mol) and DIPEA (12.9 mL, 0.0744 mol) at room temperature. The reaction mixture was stirred for 10 minutes and methyl amine hydrochloride (1.8 g, 0.0273 mol) was added. After stirring the mixture for overnight, the solvent was concentrated under reduced pressure and the residue was diluted with water (400 mL). The product was extracted with ethyl acetate (2×200 mL) and the combined organic layers were washed with brine solution (50 mL). The organic layer was dried over sodium sulphate and concentrated to get 4-bromo-N-methylbenzamide as a white solid. Yield: 5 g (94.3%).

Synthesis of N-methyl-4-(4,4,5,5-tetramethyl-1,3,2-dioxaborolan-2-yl)benzamide (3)

To a stirred solution of 4-bromo-N-methylbenzamide compound (4.00 g, 0.0186 mol) in 1,4-dioxane (10 mL) was added bis(pinacolato)diboron (11.3 g, 0.0448 mol), potassium acetate (5.30 g, 0.0541 mol) and [1,1'-Bis(diphenylphosphino)ferrocene]dichloropalladium(II) (0.305 g, 0.00037 mol). The mixture was heated at 90° C. overnight, filtered through celite and concentrated. The residue was purified by flash chromatography over silica using 40% ethyl acetate in pet ether as eluent to afford N-methyl-4-(4,4,5,5-tetramethyl-1,3,2-dioxaborolan-2-yl)benzamide as a white solid. Yield: 4.50 g (91%).

Synthesis of N-methyl-4'-nitro-[1, 1'-biphenyl]-4-carboxamide (5)

To a stirred solution of N-methyl-4-(4,4,5,5-tetramethyl-1,3,2-dioxaborolan-2-yl)benzamide (5.6 g, 0.217 mol) in 1,4-dioxane (60 mL) was added 4-bromo nitrobenzene (4 g, 0.0198 mol) and the solution was purged with nitrogen for 15 minutes. Potassium carbonate (8.19 g, 0.0594 mol) and tetrakis(triphenylphosphine)palladium(O) (0.457 g, 0.02 mol) was added and the reaction mixture was heated at 90° C. overnight. After completion of reaction, the mixture was cooled to room temperature and diluted with ethyl acetate, filtered through celite and concentrated. The crude product was purified by flash column chromatography using 40% ethyl acetate in pet ether as eluent to afford N-methyl-4'-nitro-[1,1'-biphenyl]-4-carboxamide as white solid. Yield: 4 g, (80%).

Synthesis of 4'-amino-N-methyl-[1,1'-biphenyl]-4-carboxamide (6)

To a solution of N-methyl-4'-nitro-[1,1'-biphenyl]-4-carboxamide (4.0 g, 0.0156 mol) in MeOH (80 mL) was added 10% w/w Pd on carbon (0.5 g) and hydrogenated under balloon pressure overnight. The catalyst was filtered through celite and the filtrate was evaporated to obtained 4'-amino-N-methyl-[1,1'-biphenyl]-4-carboxamide as off-white solid. Yield: 2.5 g (57%).

Synthesis of Chlorokojic Acid (8)

To a vigorously stirring suspension of kojic acid (25 g, 0.17 mol) in DCM (100 mL) was added thionyl chloride (20 g, 0.17 mol) at room temperature and the stirring was continued for 4 hours. The product precipitated as an off-white solid, which was filtered and washed with petroleum ether to afford chlorokojic acid. Yield: 21 g (73%).

Synthesis of 2-(azidomethyl)-5-hydroxy-4H-pyran-4-one (9)

To a solution of 8 (9.8 g, 0.06 mol) in DMF (40 mL) was added sodium azide (4 g, 0.06 mol) at room temperature and the solution was stirred for 16 hrs. The reaction mixture was poured into cold water (100 mL) and the precipitated product was filtered, washed with diethyl ether and dried to give 2-(azidomethyl)-5-hydroxy-4H-pyran-4-one as an off white solid. Yield: 7.8 g (76%).

Synthesis of 2-(azidomethyl)-5-(benzyloxy)-4H-pyran-4-one (10)

To a stirred solution of 2-azidomethyl-5-hydroxy-pyran-4-one (7.0 g, 0.041 mol) in methanol (50 mL) was added NaOH (2.0 g, 0.050 mol) and benzyl bromide (8.59 g, 0.050 mol). The reaction mixture was stirred at room temperature for 3 hrs. After completion of the reaction, the solvent was evaporated and the residue was diluted with water. The product was extracted with ethyl acetate (3×25 mL) and the combined organic layers were washed with water, brine and dried over sodium sulphate. The solvent was concentrated under reduced pressure and the crude product was purified by flash column chromatography using 20% ethyl acetate in pet ether to get 2-azidomethyl-5-benzyloxy-pyran-4-one. Yield: 6 g (55%).

Synthesis of 2-Aminomethyl-5-benzyloxy-pyran-4-one procedure (11)

To a stirred solution of 2-azidomethyl-5-benzyloxy-pyran-4-one (6.0 g, 0.0233 mol) in THF (100 mL) was added triphenylphosphine (12.2 g, 0.0466 mol) and water (1 mL). After refluxing for 16 h, the solvent was evaporated under reduced pressure and the crude material was purified by flash column chromatography to get (2-aminomethyl-5-benzyloxy-pyran-4-one as a brown solid. Yield: 2.6 g, (48%).

Synthesis of N-((5-(benzyloxy)-4-oxo-4H-pyran-2-yl)methyl)methanesulfonamide (12)

To a stirred solution of 2-aminomethyl-5-benzyloxy-pyran-4-one (2.6 g, 0.0112 mol) in DCM (80 mL) was added pyridine (3.5 g, 0.044 mol) under ice cold conditions, followed by the addition of methanesulfonyl chloride (3.2 g, 0.028 mol) and the reaction mixture was stirred at room temperature for 16 h. After completion of the reaction, it was quenched with water and extracted with ethyl acetate. The combined organic layers were washed with saturated sodium bicarbonate, water and brine. The organic layer was dried over sodium sulphate and concentrated under reduced pressure. The crude mixture was purified by flash column chromatography to give N-((5-(benzyloxy)-4-oxo-4H-pyran-2-yl)methyl)methanesulfonamide as an off-white solid. Yield: 1.5 g (43.3%).

Synthesis of N-((5-hydroxy-4-oxo-4H-pyran-2-yl)methyl)methanesulfonamide (13)

N-((5-(benzyloxy)-4-oxo-4H-pyran-2-yl) methyl)methanesulfonamide (1.5 g, 0.004 mol) was dissolved in acetic acid (20 mL) and sulfuric acid (0.2 mL) and the reaction mixture was heated to 80° C. overnight. After completion of the reaction, the mixture was cooled to room temperature and concentrated under vacuum. It was then diluted with water and extracted with ethyl acetate. The combined organic layers were washed with water and brine, dried over sodium sulphate and concentrated under reduced pressure. The crude product was washed with diethyl ether to get N-((5-hydroxy-4-oxo-4H-pyran-2-yl) methyl) methane sulfonamide as brown solid. Yield: 500 mg. (50%).

Synthesis of 4'-(((3-hydroxy-6-(methylsulfonamidomethyl)-1-oxo-4H-pyran-2-yl) methyl) amino)-N-methyl-[1,1'-biphenyl]-4-carboxamide (Compound 1)

To a solution of 4'-amino-N-methyl-[1,1'-biphenyl]-4-carboxamide (300 mg, 0.001 mol) in methanol (10 mL) was added a 37% (w/w) aqueous formaldehyde solution (161 mg, 0.0019 mol) and the mixture was stirred at 70° C. for 60 min under $N_2$ atmosphere. N-((5-hydroxy-4-oxo-4H-pyran-2-yl) methyl) methane sulfonamide (347 mg, 0.0015 mol) was added as a solid and the reaction was refluxed overnight under $N_2$. The solvent was concentrated in vacuo and the crude material was purified by prep. HPLC purification followed by flash column chromatography using 10% methanol in DCM to afford Compound 1 as a white solid. Yield: 25 mg (4%). $^1$H NMR (400 MHz, DMSO-d6, δ): 2.79 (d, J=4.40 Hz, 3H), 2.90 (s, 3H), 4.07 (d, J=6.40 Hz, 2H), 4.29 (d, J=6.00 Hz, 2H), 6.36 (s, 1H), 6.45 (m, 1H), 6.76 (d, J=8.40 Hz, 2H), 7.50 (d, J=8.40 Hz, 2H), 7.63 (d, J=8.40 Hz, 2H), 7.76 (m, 1H), 7.83 (d, J=8.40 Hz), 8.39 (brs, 1H), 9.36 (s, 1H). MS (ES) (M+H)$^+$: 458.3 for $C_{22}H_{23}N_3O_6S$.

Synthesis of Compound 2

Figure 11:
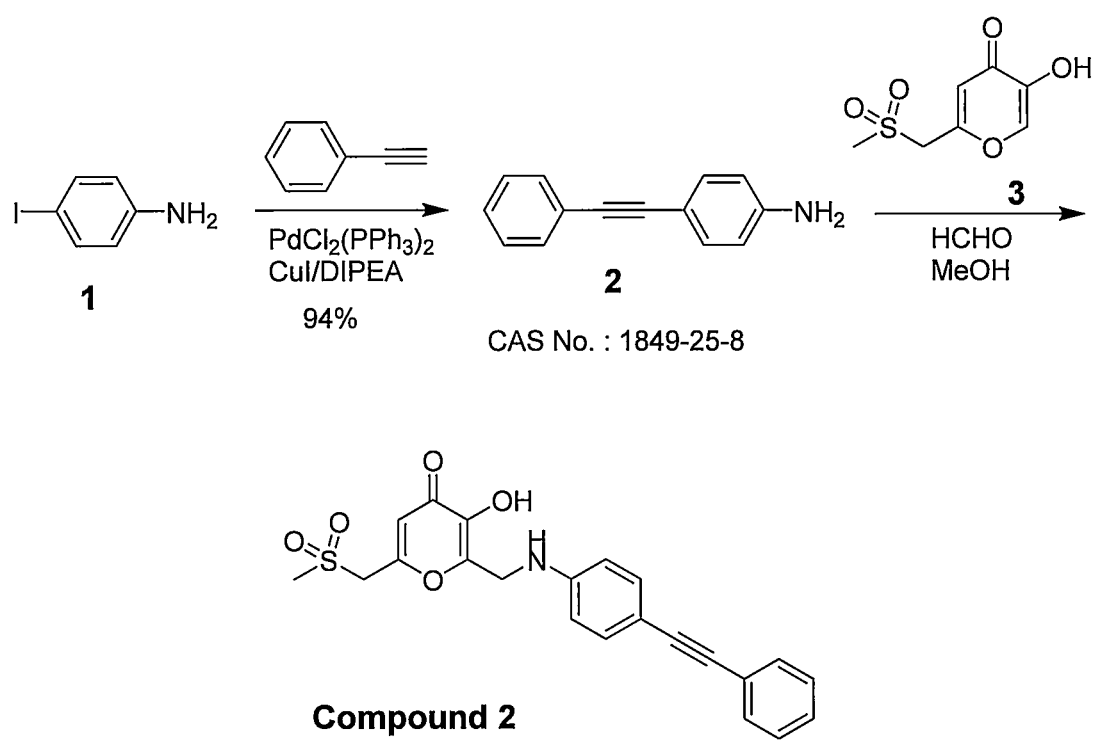
FIG. 11 shows a synthetic scheme to prepare compound 2.

The synthetic scheme to prepare compound 2 is shown in FIG. 11.

Synthesis of 4-(phenylethynyl)aniline (2)

A mixture of phenyl acetylene (5 g, 0.049 mol), 4-iodo aniline (10.7 g, 0.049 mol), CuI (932 mg, 0.049 mol), [1,1-bis(diphenylphosphino)ferrocene]-dichloropalladium (II) (3.9 g, 0.0049 mol) and triethylamine (14.8 g, 0.147 mol) in acetonitrile in a sealed tube was evacuated and backfilled with nitrogen (3 cycles). The mixture was stirred at reflux for 2 h. After completion of the reaction, the reaction mixture was cooled to room temperature and diluted with ethyl acetate. The mixture was filtered through celite and concentrated. The residue was diluted with water and extracted with ethyl acetate (3×200 mL). The combined organic layers were dried over $Na_2SO_4$ and concentrated. The crude product was further purified by silica gel column chromatography using 20-30% of ethyl acetate in petroleum ether as eluent to provide the 4-(phenylethynyl) aniline as an off-white solid. Yield: 5.6 g (59%).

Synthesis of 5-hydroxy-2-((methylsulfonyl)methyl)-4H-pyran-4-one (3)

A suspension of chloro kojic acid (2 g, 0.011 mol) and sodium methanesulfinate (1.5 g, 0.015 mol) in water (12 mL) was irradiated in microwave at 120° C. for 30 min. The reaction mixture upon cooling to room temperature, the desired product was crystallized out of solution as a white solid. Yield: 2 g, (90%).

Synthesis of 2-((4-(2-phenylethynyl)phenylamino) methyl)-3-hydroxy-6-((methylsulfonyl)methyl)-4H-pyran-4-one (Compound 2)

To a solution of 4-(phenylethynyl) aniline (350 mg, 0.001 mol) in methanol (10 mL) was added 41% (w/v) aqueous formaldehyde solution (180 mg, 0.002 mol). The resulting solution was stirred at 70° C. for 1 h under $N_2$ atmosphere. 5-hydroxy-2-((methylsulfonyl)methyl)-4H-pyran-4-one (369 mg, 0.01 mol) was added to the solution as a solid and the reaction mixture was stirred at reflux (80° C.) for overnight. The reaction mixture was concentrated under reduced pressure and the crude product was purified by prep. HPLC to afford compound 57 as an off-white solid. Yield: 30 mg (4%). $^1$H NMR (400 MHz, DMSO-d6, δ): 3.02 (s, 3H), 4.30 (d, J=6.04 Hz, 2H), 4.57 (s, 2H), 6.49 9s, 1H), 6.64-6.72 (m, 3H), 7.26 (m, 2H), 7.34-7.45 (m, 3H), 7.47 (m, 2H), 9.55 (s, 1H). MS (ES) (M–H)$^+$: 408.0 for $C_{22}H_{19}NO_5S$.

Synthesis of Compound 4

Figure 12:
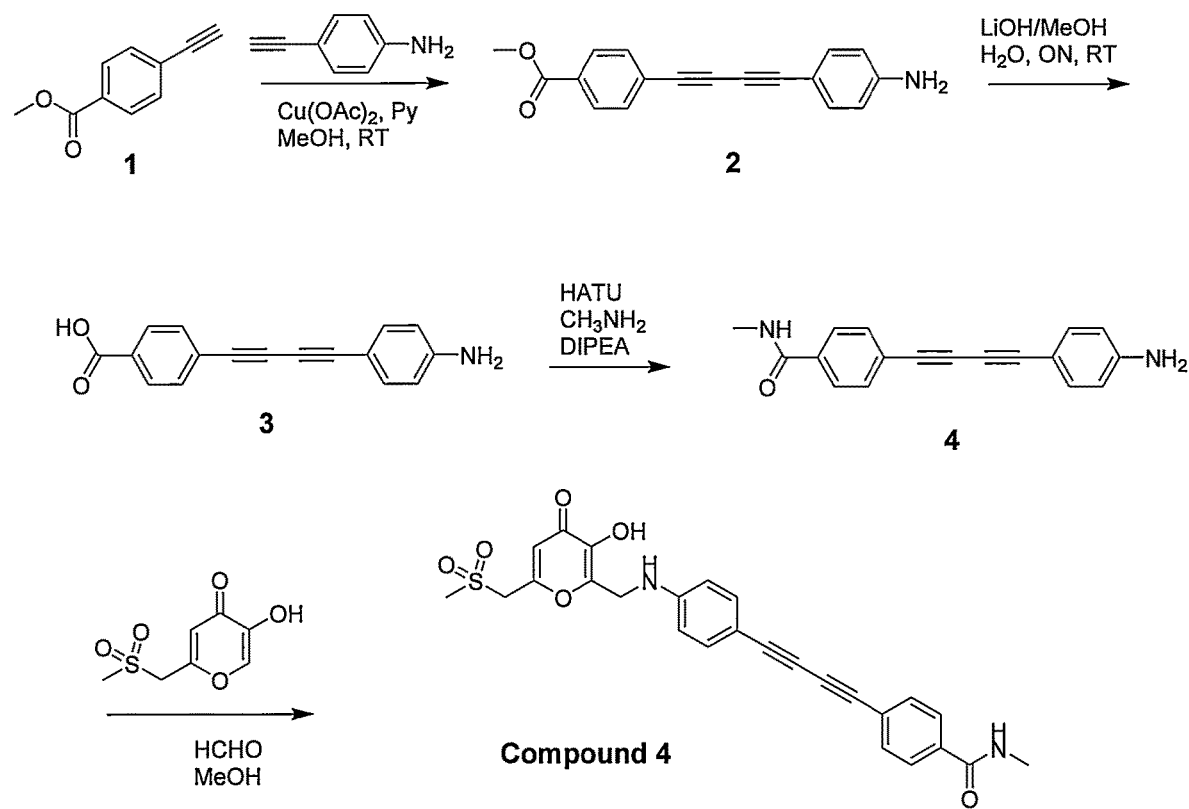
FIG. 12 shows a synthetic scheme to prepare compound 4.

The synthetic scheme to prepare compound 4 is shown in FIG. 12.

Synthesis of methyl 4-(4-(4-aminophenyl)buta-1,3-diynyl)benzoate (2)

Methyl 4-ethynyl benzoate (4 g, 0.0249 mol), 4-ethynyl aniline (14.6 g, 0.124 mol), copper(II) acetate (9 g, 0.0498 mol), pyridine (40 mL) in methanol (40 mL) were added to a sealed tube. The sealed tube was then evacuated and backfilled with nitrogen (3 cycles). The mixture was stirred at room temperature for 24 h. After completion of the reaction, the solvent was evaporated and the crude product was purified by silica gel column chromatography by using 10-20% ethyl acetate in petroleum ether as eluent to provide the methyl 4-(4-(4-aminophenyl)buta-1,3-diynyl)benzoate as an off-white solid. Yield: 2 g (29%).

Synthesis of 4-(4-(4-aminophenyl)buta-1,3-diynyl) benzoic acid (3)

A 3N solution of NaOH (20 mL) was added to the stirred solution of methyl 4-(4-(4-aminophenyl)buta-1,3-diynyl) benzoate (2 g, 0.0036 mol) in MeOH (40 mL) at room temperature and heated to reflux for 1 h. The reaction mixture was cooled to room temperature and MeOH was removed under reduced pressure. Water (20 mL) was added and the pH was adjusted to 2 using Conc HCl. The yellow precipitate was filtered and washed with water (2×20 mL), dried under high vacuum to give 4-(4-(4-aminophenyl)buta-1,3-diynyl)benzoic acid as an off-white solid. Yield: 1.5 g (79%).

Synthesis of 4-(4-(4-aminophenyl)buta-1,3-diynyl)-N-methylbenzamide (4)

To a solution of 4-(4-(4-aminophenyl)buta-1,3-diynyl) benzoic acid (500 mg, 0.001 mol) in DMF (5 mL) was added HATU (0.87 g, 0.002 mol) followed by DIPEA (0.74 g, 0.005 mol) and the reaction mixture was stirred for 10 minutes. Methylamine hydrochloride (0.14 g, 0.002 mol) was added and the stirring was continued for overnight. After completion of reaction, the solvent was concentrated and the residue was diluted with water (400 mL). The product was extracted with ethyl acetate (2×50 mL) and the combined organic layers were washed with brine solution (50 mL), dried over sodium sulphate and concentrated. The crude product was purified by column chromatography using 5% methanol in DCM to get 4-(4-(4-aminophenyl) buta-1,3-diynyl)-N-methylbenzamide as a white solid. Yield: 300 mg (57%).

Synthesis of 4-((4-(((3-hydroxy-6-((methylsulfonyl) methyl)-4-oxo-4H-pyran-2-yl)methyl)amino)phenyl) buta-1,3-diyn-1-yl)-N-methylbenzamide (Compound 57)

To a solution of 4-(4-(4-aminophenyl)buta-1,3-diynyl)-N-methylbenzamide (300 mg, 0.001 mol) in methanol (10 mL) was added of a 41% (w/v) aqueous formaldehyde solution (176 mg, 0.002 mol). The resulting solution was stirred at 70° C. for 1 h under $N_2$ atmosphere. 5-hydroxy-2-((methylsulfonyl)methyl)-4H-pyran-4-one (268 mg, 0.01 mol) was added to the solution as a solid and the reaction mixture was stirred at reflux for overnight. The reaction mixture was concentrated in vacuo and purified by prep. HPLC to afford Compound 4 as an off-white solid. Yield: 25 mg (4%). $^1$H NMR (400 MHz, DMSO-d6, δ): 2.78 (d, J=4.40 Hz, 3H), 3.01 (s, 3H), 4.30 (d, J=5.60 Hz, 2H), 4.56 (s, 2H), 6.48 (s, 1H), 6.64 (d, J=8.80 Hz, 2H), 6.96 (m, 1H), 7.32 (d, J=8.40 Hz, 2H), 7.62 (d, J=8.40 Hz, 2H), 7.83 (d, J=8.40 Hz, 2H), 8.53 (m, 1H), 9.57 (s, 1H). MS (ES) (M+H)$^+$: 491.0 for $C_{26}H_{22}N_2O_6S$.

Synthesis of Compound 5

Figure 13:
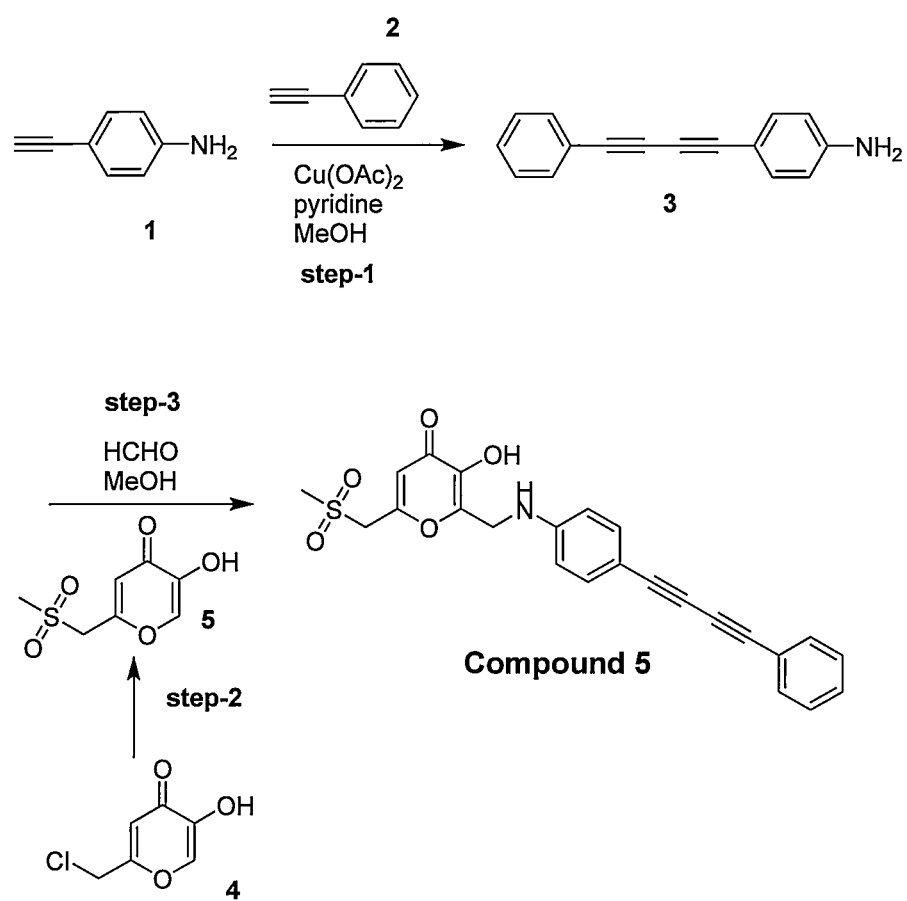
FIG. 13 shows a synthetic scheme to prepare compound 5.

The synthetic scheme to prepare compound 5 is shown in FIG. 13.

Synthesis of 4-(4-phenylbuta-1,3-diynyl)benzenamine (3)

4-ethylnyl aniline (1 g, 0.006 mol), phenyl acetylene (2.6 g, 0.025 mol), copper(II) acetate (2.3 g, 0.013 mol), pyridine (5 mL) in methanol (10 mL) were added to a sealed Tube. The sealed tube was evacuated and backfilled with nitrogen (3 cycles). The mixture was stirred at room temperature for 24 h. After completion of the reaction, the solvent was concentrated. The crude product was purified by silica gel chromatography using 10-20% petroleum ether and ethyl acetate as eluent to provide the 4-(4-phenylbuta-1,3-diynyl) benzenamine as an off-white solid. Yield: 1.1 g (78%).

Synthesis of 5-hydroxy-2-((methylsulfonyl)methyl)-4H-pyran-4-one (5)

A suspension of chlorokojic acid (2 g, 0.011 mol) and sodium methanesulfinate (1.5 g, 0.015 mol) in water (12 mL) was irradiated in microwave at 120° C. for 30 min. The mixture was cooled to room temperature and the product was crystallized out of solution as a white solid. Yield: 2 g (90%).

Synthesis of 2-((4(4-(4-phenylbuta-1,3-diynyl)phenylamino)methyl)-3-hydroxy-6-((methylsulfonyl) methyl)-4H-pyran-4-one (Compound 60)

To a solution of 4-(4-phenylbuta-1,3-diynyl)benzenamine (350 mg, 0.001 mol) in methanol (10 mL) was added of a 41% (w/v) aqueous formaldehyde solution (180 mg 0.002 mol). The resulting solution was stirred at 70° C. for 1 h under $N_2$ atmosphere. 5-hydroxy-2-((methylsulfonyl) methyl)-4H-pyran-4-one (394 mg, 0.01 mol) was added to the solution as a solid and the reaction was stirred at reflux for overnight. The reaction mixture was concentrated under reduced pressure and the crude product was purified by prep. HPLC to afford 2-((4-(4-phenylbuta-1, 3-diynyl)phenylamino)methyl)-3-hydroxy-6-((methylsulfonyl)methyl)-4H-pyran-4-one as an off-white solid. Yield: 32 mg (4%). $^1$H NMR (400 MHz, DMSO-d6δ): 3.02 (s, 3H), 4.31 (d, J=5.48 Hz, 2H), 4.57 (s, 2H), 6.49 (s, 1H), 6.64 (m, 2H), 6.94 (m, 1H), 7.31 (m, 2H), 7.43 (m, 3H), 7.56 (m, 2H), 9.58 (s, 1H). MS (ES) (M–H)$^+$: 432.0 for $C_{24}H_{19}NO_5S$.

Synthesis of Compound 6

Figure 14:
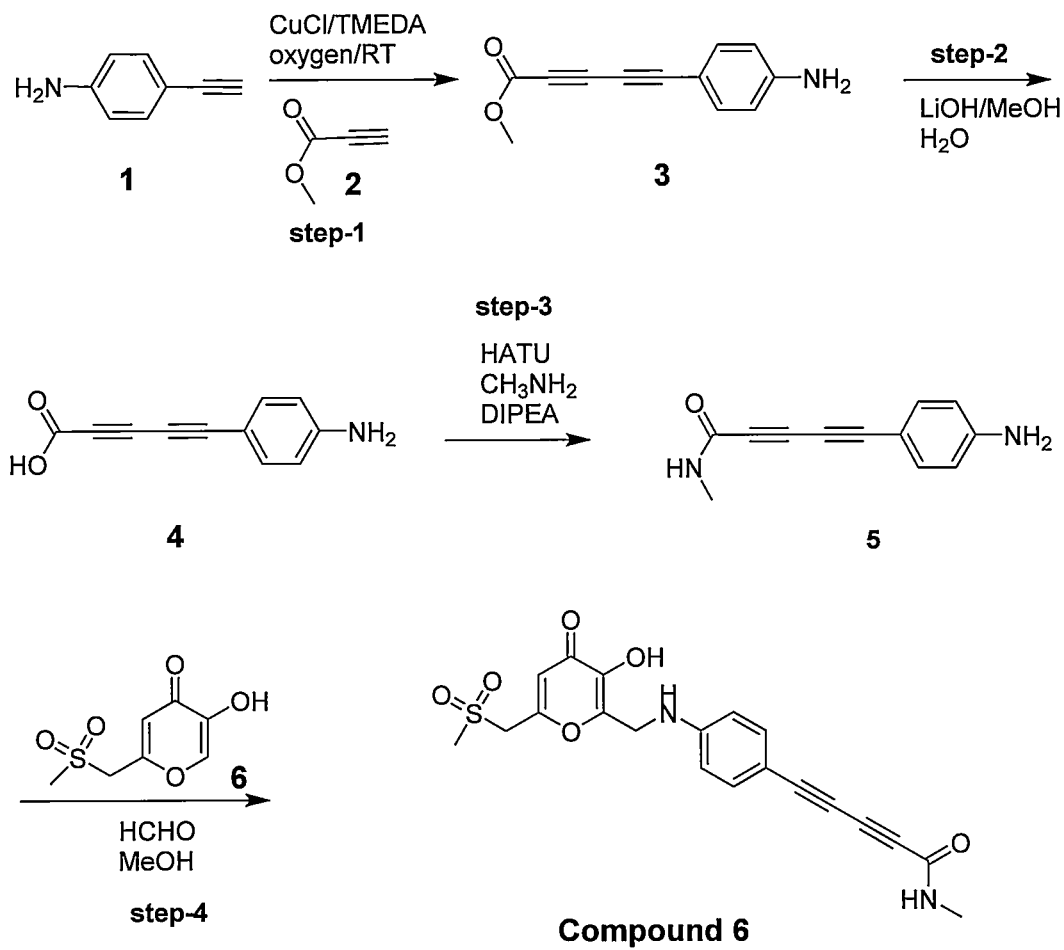
FIG. 14 shows a synthetic scheme to prepare compound 6.

The synthetic scheme to prepare compound 6 is shown in FIG. 14.

Synthesis of methyl 5-(4-aminophenyl)penta-2,4-diynoate (3)

Hay catalyst is prepared by stirring CuCl (500 mg, 0.00512 mol) and TMEDA (0.12 mL, 0.0007 mol) in acetone (20 mL) with simultaneous bubbling of stream of oxygen for 40 min. A solution of 4-ethynyl aniline (3 g, 0.0256 mol) and methyl propiolate (2.3 mL, 0.0256 mol) in anhydrous acetone was then introduced into the flask containing heterogeneous Hay catalysts in acetone and then stirred at room temperature for overnight. The solvent was evaporated and the residue was chromatographed through a silica gel column using 20-30% ethyl acetate in pet ether as eluent to get methyl 5-(4-aminophenyl) penta-2,4-diynoateas an off-white solid. Yield: 1.3 g (26%).

Synthesis of 5-(4-aminophenyl)penta-2,4-diynoic acid (4)

A 3N solution of NaOH (20 mL) was added to stirred solution of methyl 5-(4-aminophenyl) penta-2,4-diynoate (2 g, 0.01 mol) in MeOH (20 mL) at room temperature and heated to reflux for 1 h. The reaction mixture was cooled to room temperature and the solvent was removed by evaporation under reduced pressure. Water (20 mL) was added to the residue and acidified with Conc. HCl to pH 2. The yellow precipitate was filtered, washed with water (2×20 mL) and dried to give 5-(4-aminophenyl)penta-2,4-diynoic acid as an off-white solid. Yield: 690 mg (75%).

Synthesis of 5-(4-aminophenyl)-N-methylpenta-2,4-diynamide (5)

To a solution of 5-(4-aminophenyl)penta-2,4-diynoic acid (700 mg, 0.003 mol) in DMF (10 mL) was added HATU (1.1 g, 0.003 mol) followed by DIPEA (1.16 g, 0.009 mol) and reaction mixture was stirred for 10 minutes. Methylamine hydrochloride (270 mg, 0.004 mol) was added and for overnight. After completion of reaction, the reaction mixture was concentrated and the residue was diluted with water (100 mL), extracted with ethyl acetate (2×50 mL). The combined organic layers were washed with brine solution (50 mL), dried over sodium sulphate and concentrated. The crude product was purified by column chromatography using 3% of methanol in DCM to furnish 5-(4-aminophenyl)-N-methylpenta-2,4-diynamide as a white solid. Yield: 600 mg (44%).

Step 4: 5-(4-(((3-hydroxy-6-((methylsulfonyl)methyl)-4-oxo-4H-pyran-2-yl)methyl)amino)phenyl)-N-methylpenta-2,4-diynamide procedure (Compound 61)

To a solution of 4-(4-(4-aminophenyl)buta-1,3-diynyl)-N-methylbenzamide (500 mg, 0.002 mol) in methanol (10 mL) was added of a 41% (w/v) aqueous formaldehyde solution (227 mg, 0.006 mol) and stirred at 70° C. for 1 h under $N_2$ atmosphere. 5-hydroxy-2-((methylsulfonyl)methyl)-4H-pyran-4-one (618 mg, 0.003 mol) was added to the solution as a solid and the reaction mixture was stirred at reflux for overnight. The reaction mixture was concentrated under reduced pressure and the crude product was purified by prep. HPLC to afford 5-(4-(((3-hydroxy-6-((methylsulfonyl)methyl)-4-oxo-4H-pyran-2-yl)methyl)amino)phenyl)-N-methylpenta-2,4-diynamide as an off-white solid. Yield: 25 mg (3%). $^1$H NMR (400 MHz, MeOD, δ): 2.77 (s, 3H), 2.92 (s, 3H), 4.46 (m, 3H), 4.83 (s, 2H), 6.53 (s, 1H), 6.68 (m, 2H), 7.32 (m, 2H). MS (ES) (M–H)$^+$: 413.0 for $C_{20}H_{18}N_2O_6S$.

Synthesis of Compound 7

Figure 15:
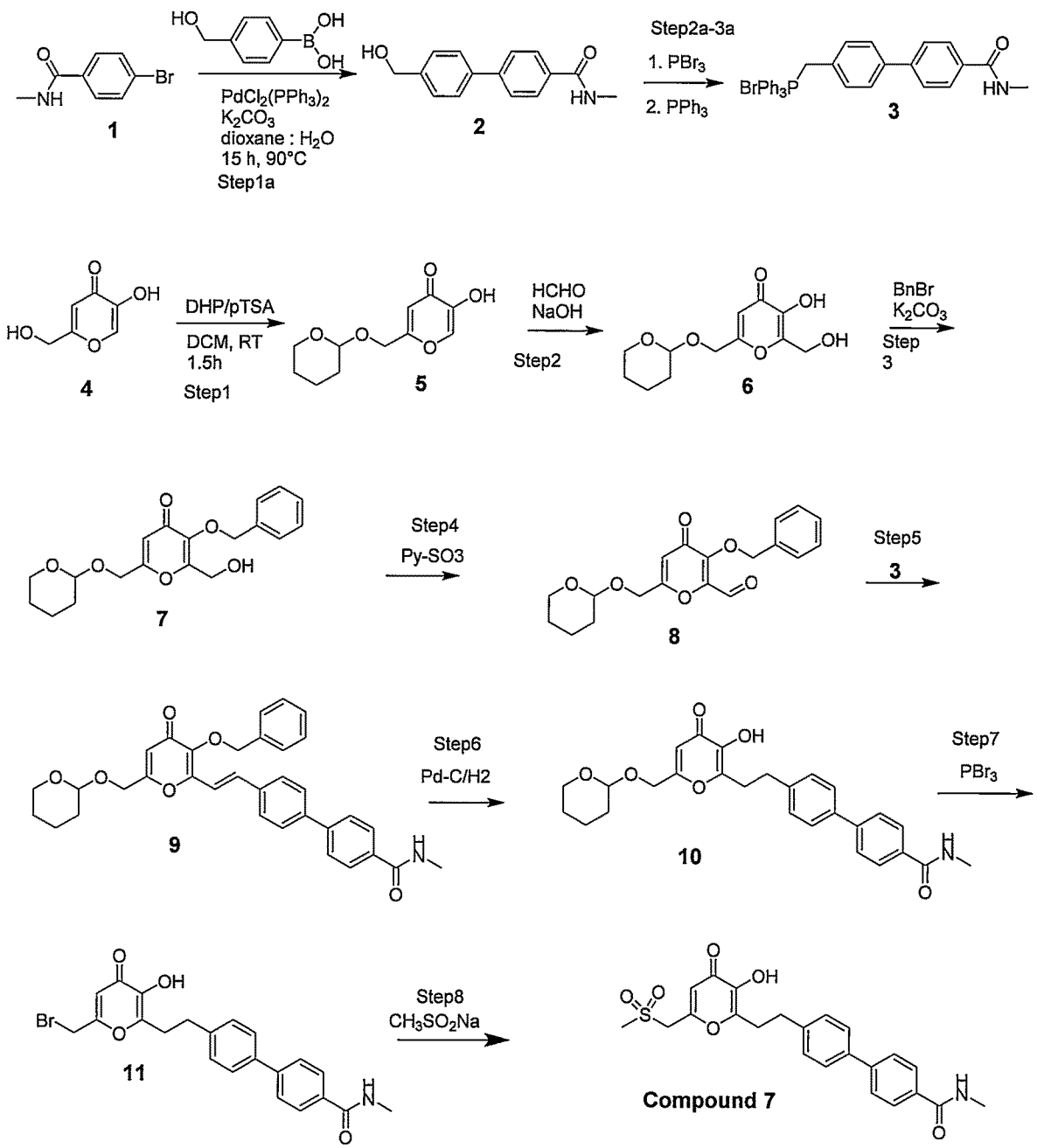
FIG. 15 shows a synthetic scheme to prepare compound 7.

The synthetic scheme to prepare compound 7 is shown in FIG. 15.

Synthesis of 4'-(hydroxymethyl)-N-methyl-[1,1'-biphenyl]-4-carboxamide (2)

To a stirred solution of 4-bromo-N-methylbenzamide (2 g, 9.34 mmol) in 1, 4-dioxane (40 mL) were added 4-(hydroxymethyl)phenyl boronic acid (1.70 g, 11.21 mmol), potassium carbonate (2.57 g, 18.68 mmol) followed by water (5 mL) respectively. The resulting solution was purged with nitrogen for 15 minutes. Then added bis(triphenylphosphine)palladium(II) chloride (0.655 g, 0.934 mmol). The reaction mixture was heated to 100° C. for 4 h. After completion of reaction by TLC, cooled to room temperature and diluted with ethyl acetate, then filtered through celite and concentrated in vacuo. The crude product was purified by flash column chromatography using 65% ethyl acetate in pet ether to obtained 4'-(hydroxymethyl)-N-methyl-[1,1'-biphenyl]-4-carboxamide (2) as white solid. Yield: 1.5 g (67%).

Synthesis of 4'-((bromotriphenyl-15-phosphanyl)methyl)-N-methyl-[1,1'-biphenyl]-4-carboxamide (3)

To a stirred solution Compound 2 (1.5 g, 6.224 mmol) in DCM (30 mL), cooled to 0° C., phosphorous tribromide (2.52 g, 9.33 mmol) was added and stirred at 25° C. for 2 h. After completion the reaction by TLC, the mixture was quenched with water and extracted with dichloromethane. The combined organic layers were washed with brine, dried over sodium sulfate and concentrated in vacuo at 40° C. The crude product (1.2 g) was taken in dry toluene (20 mL), triphenyl phosphine (1.03 g, 3.94 mmol) was added and refluxed at 110° C. for 2 h. The solvent was concentrated under reduced pressure to afford 4'-((bromotriphenyl-15-phosphanyl)methyl)-N-methyl-[1,1'-biphenyl]-4-carboxamide (3) as a white solid. Yield: 1.7 g, (76.23%).

Synthesis of 5-hydroxy-2-(((tetrahydro-2H-pyran-2-yl)oxy)methyl)-4H-pyran-4-one (5)

To a stirred mixture of kojic acid (5.7 g, 40 mmol) and 3,4-dihydro-2H-pyran (4.2 mL, 46 mmol) in dichloromethane (200 mL) at room temperature was added p-toluene sulfonic acid monohydrate (38 mg, 0.2 mmol). The reaction mixture was stirred for 1.5 h and extracted with 3% aqueous sodium hydroxide solution (2×70 mL). The combined aqueous phases were neutralized to pH 7~8 with 0.5 M sodium dihydrogen phosphate and extracted with dichloromethane (2×50 mL). The combined organic extracts were dried over sodium sulfate, evaporated in vacuo. Recrystallization of the crude product in ethyl acetatehexane gave the 5-hydroxy-2-(((tetrahydro-2H-pyran-2-yl)oxy)methyl)-4H-pyran-4-one (5) as a pale orange solid. Yield: 8.6 g (95%).

Synthesis of 3-hydroxy-2-(hydroxymethyl)-6-(((tetrahydro-2H-pyran-2-yl)oxy)methyl)-4H-pyran-4-one (6)

To a stirred solution of 5-hydroxy-2-(((tetrahydro-2H-pyran-2-yl)oxy)methyl)-4H-pyran-4-one (8.5 g, 0.037 mol) in 1,4-dioxane (100 mL), formaldehyde (8 mL), aqueous sodium hydroxide (1.5 g, 0.037 mol) were added and stirred at 25° C. for 6 h. The mixture was concentrated in vacuo, neutralized with 1.5N HCl and extracted with ethyl acetate (3×400 mL). The combined organic layers were washed with brine, dried over sodium sulfate and concentrated in vacuo to provide the crude product of 3-hydroxy-2-(hydroxymethyl)-6-(((tetrahydro-2H-pyran-2-yl)oxy)methyl)-4H-pyran-4-one. Yield: 6 g (63.35%).

Synthesis of 3-hydroxy-2-(hydroxymethyl)-6-(((tetrahydro-2H-pyran-2-yl)oxy)methyl)-4H-pyran-4-one (7)

To a stirred solution of 3-hydroxy-2-(hydroxymethyl)-6-(((tetrahydro-2H-pyran-2-yl)oxy)methyl)-4H-pyran-4-one (6 g, 0.0234 mol) in DMF (50 mL), potassium carbonate (6.46 g, 0.0468 mol), benzyl bromide (4.22 g, 0.0246 mol) were added and stirred at 25° C. for 16 h. After completion of the reaction by TLC, the mixture was quenched with water and extracted with ethyl acetate (2×150 mL). The combined organic layers were washed with water, brine, dried over sodium sulfate and concentrated. The crude product was purified by column chromatography on silica gel with gradient elution of 40-50% ethyl acetate in pet ether to afford 3-(benzyloxy)-2-(hydroxymethyl)-6-(((tetrahydro-2H-pyran-2-yl)oxy)methyl)-4H-pyran-4-one (7) as a pale yellow oil. Yield: 4 g (49.38%).

Synthesis of 3-(benzyloxy)-4-oxo-6-(((tetrahydro-2H-pyran-2-yl)oxy)methyl)-4H-pyran-2-carbaldehyde (8)

To a stirred solution of 3-(benzyloxy)-2-(hydroxymethyl)-6-(((tetrahydro-2H-pyran-2-yl)oxy)methyl)-4H- pyran-4-one (2 g, 0.0057 mol) in DCM (40 mL), DMSO (2.70 g, 0.0346 mol), DIPEA (4.47 g, 0.0346 mol), Py-SO3 complex (4.45 g, 0.0285 mol) were added and stirred at 25° C. for 16 h. After completion of the reaction by TLC, the mixture was quenched with water and extracted with ethyl acetate (2×100 mL). The combined organic layers were washed with water, brine, dried over sodium sulfate and concentrated in vacuo at 40° C. to furnish the crude product of 3-(benzyloxy)-4-oxo-6-(((tetrahydro-2H-pyran-2-yl)oxy) methyl)-4H-pyran-2-carbaldehyde (8) as a pale yellow oil. Yield: 1 g (51.02%).

Synthesis of (E)-4'-(2-(3-(benzyloxy)-4-oxo-6-(((tetrahydro-2H-pyran-2-yl)oxy)methyl)-4H-pyran-2-yl) vinyl)-N-methyl-[1,1'-biphenyl]-4-carboxamide (9)

To a stirred solution of 3-(benzyloxy)-4-oxo-6-(((tetrahydro-2H-pyran-2-yl)oxy)methyl)-4H-pyran-2-carbaldehyde (1 g, 0.0029 mol) in 1,2-dichloroethane (20 mL), Compound 3 (1.64 g, 0.0029 mol), potassium carbonate (0.432 g, 0.0031 mol), 18-crown-6 (0.137 g, 0.0005 mol) were added and stirred at 25° C. for 16 h. After completion the reaction by TLC, the mixture was concentrated in vacuo and the crude material was purified by column chromatography on silica gel with gradient elution of 70-80% ethyl acetate in pet ether to obtain (E)-4'-(2-(3-(benzyloxy)-4-oxo-6-(((tetrahydro-2H-pyran-2-yl)oxy)methyl)-4H-pyran-2-yl)vinyl)-N-methyl[1,1'-biphenyl]-4-carboxamide (9) as a colorless gummy solid. Yield: 0.45 g (28.30%).

Synthesis of (E)-4'-(2-(3-(benzyloxy)-4-oxo-6-(((tetrahydro-2H-pyran-2-yl)oxy)methyl)-4H-pyran-2-yl) vinyl)-N-methyl-[1,1'-biphenyl]-4-carboxamide (10)

A mixture of compound 9 (0.45 g, 0.0008 mol) in ethyl acetate (20 mL) was hydrogenated in the presence of 10% Pd/C (0.05 g) under balloon pressure of hydrogen, overnight. The progress of the reaction was monitored by UPLC. After filtering off the catalyst, the filtrate was evaporated and dissolved in 8 mL of MeOH. The reaction mixture was once again hydrogenated in the presence of fresh Pd/C (10 mg) catalyst, under balloon pressure of hydrogen for 2 h. After completion the reaction by UPLC, the catalyst was filtered through celite bed using methanol and the filtrate was concentrated in vacuo to afford 4'-(2-(3-hydroxy-4-oxo-6-(((tetrahydro-2H-pyran-2-yl)oxy)methyl)-4H-pyran-2-yl) ethyl)-N-methyl-[1,1'-biphenyl]-4-carboxamide (10) as off-white solid. Yield: 0.2 g (52.91%).

Synthesis of 4'-(2-(6-(bromomethyl)-3-hydroxy-4-oxo-4H-pyran-2-yl)ethyl)-N-methyl-[1,1'-biphenyl]-4-carboxamide (11)

To a stirred solution of 4'-(2-(3-hydroxy-4-oxo-6-(((tetrahydro-2H-pyran-2-yl)oxy)methyl)-4H-pyran-2-yl)ethyl)-N-methyl-[1,1'-biphenyl]-4-carboxamide (0.2 g, 0.00043 mol) in DCM (6 mL), cooled to 0° C., phosphorous tribromide (0.175 g, 0.0006 mol) was added and stirred at 25° C. for 2 h. After completion the reaction by TLC, the reaction mixture was quenched with water and extracted with DCM. The combined organic layer were washed with water, brine, dried over sodium sulfate and concentrated in vacuo to give the crude product of 4'-(2-(6-(bromomethyl)-3-hydroxy-4-oxo-4H-pyran-2-yl)ethyl)-N-methyl-[1,1'-biphenyl]-4-carboxamide as a pale yellow solid. Yield: 0.08 g (42.10%).

Synthesis of 4'-(2-(3-hydroxy-6-((methylsulfonyl) methyl)-4-oxo-4H-pyran-2-yl)ethyl)-N-methyl-[1,1'-biphenyl]-4-carboxamide (Compound 3)

To a stirred solution of 4'-(2-(6-(bromomethyl)-3-hydroxy-4-oxo-4H-pyran-2-yl)ethyl)-N-methyl[1,1'-biphenyl]-4-carboxamide (0.08 g, 0.0001 mol) in DMF (2 mL), sodium methanesulfinate (0.018 g, 0.0001 mol) was added and stirred at 25° C. for 2 h. After completion of the reaction by TLC, the mixture was quenched with ice water. The precipitate was filtered, washed with water and acetonitrile to get a pure compound of 4'-(2-(3-hydroxy-6-((methylsulfonyl)methyl)-4-oxo-4H-pyran-2-yl)ethyl)-N-methyl-[1,1'-biphenyl]-4-carboxamide as off white solid. Yield: 21 mg (47.72%). $^1$H NMR (400 MHz, DMSO-d6, δ): 2.80 (s, 3H), 2.98 (s, 4H), 3.06 (s, 3H), 4.61 (s, 2H), 6.45 (s, 1H), 7.33 (d, J=8.20 Hz, 2H), 7.63 (d, J=8.16 Hz, 2H), 7.73 (d, J=8.36 Hz, 2H), 7.90 (d, J=8.36 Hz, 2H), 8.47 (s, 1H), 9.02 (s, 1H). MS (ES) (M+H)$^+$: 442.0 for $C_{23}H_{23}NO_6S$.

Synthesis of Compound 8

Figure 16:
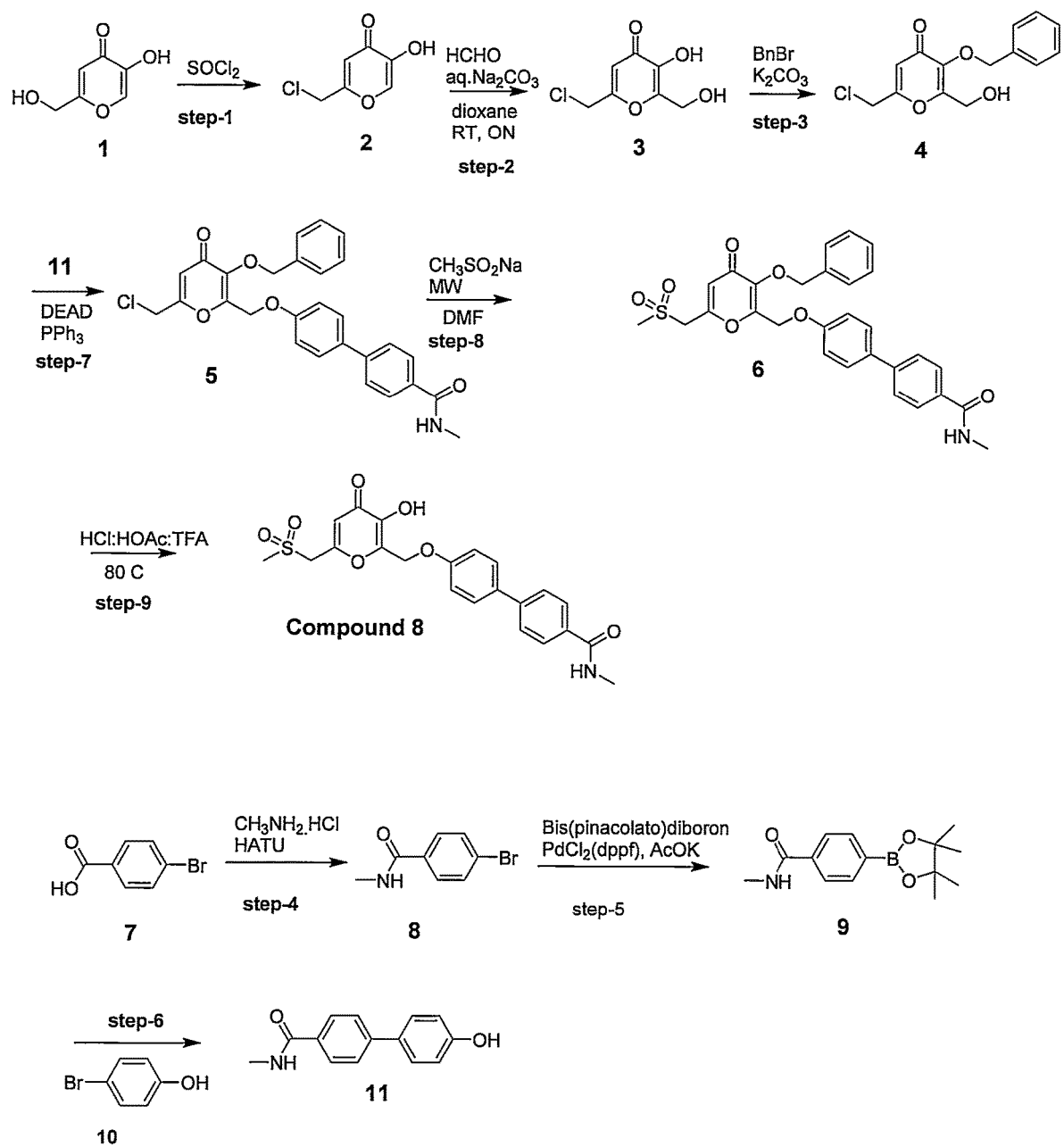
FIG. 16 shows a synthetic scheme to prepare compound 8.

The synthetic scheme to prepare compound 8 is shown in FIG. 16.

Synthesis of 2-(chloromethyl)-5-hydroxy-4H-pyran-4-one (2)

To a vigorously stirring suspension of Kojic acid (25 g, 0.17 mol) in DCM (100 mL) was added thionyl chloride at room temperature (20 g, 12.8 mL, 0.17 mol) and continued to stir at RT for 4 hours. The product precipitates as an off white solid which is filtered and washed with petroleum ether. Yield 21 g (73%).

Synthesis of 6-(chloromethyl)-3-hydroxy-2-(hydroxymethyl)-4H-pyran-4-one (3)

To a stirred solution of compound-2 (11.0 g, 0.068 mol) in dioxane (60 mL) was added Na$_2$CO$_3$ (8.0 g, 0.075 mol) in water (5 mL) and 41% w/v formaldehyde solution (6.2 g, 0.076 mol) and the reaction mixture was stirred at room temperature overnight. After completion of the reaction, the solvent was evaporated under reduce pressure, then it was diluted with water (100 mL) and P$^H$ of the solution was adjusted to 7-8 by using 10% NaOH solution (5 mL). The aqueous layer was extracted with ethyl acetate (2×250 mL) and combined organic layers were washed with water (50 mL) and brine (50 mL), dried over sodium sulphate, concentrated under reduced pressure to provide 6-(chloromethyl)-3-hydroxy-2-(hydroxymethyl)-4H-pyran-4-one as a brown liquid. The residue was taken for next step without purification. (Crude yield—6 g, 46%).

Synthesis of 3-(benzyloxy)-6-(chloromethyl)-2-(hydroxymethyl)-4H-pyran-4-one (4)

To a stirred solution of 6-(chloromethyl)-3-hydroxy-2-(hydroxymethyl)-4H-pyran-4-one (6.0 g, 0.063 mol) in DMF (50 mL) was added K$_2$CO$_3$ (8.7 g, 0.063 mol) followed by benzyl bromide (7.7 mL, 0.063 mol) and the reaction mixture was stirred at room temperature for 6 h. After completion of the reaction, the solvent was evaporated under reduce pressure, diluted with water and extracted with ethyl acetate (2×200 mL). The combined organic layers were washed with water (200 mL) and brine (50 mL), dried over sodium sulphate, concentrated under reduced pressure and purified by flash column chromatography using 20% ethyl acetate in pet ether to get 3(benzyloxy)-6-(chloromethyl)-2-(hydroxymethyl)-4H-pyran-4-one, Yield: 3.8 g (43%).

Synthesis of 4-bromo-N-methylbenzamide (8)

To a solution of 4-bromo benzoic acid (5 g, 0.0248 mol) in DMF (40 mL) was added HATU (11.3 g, 0.0297) followed by DIPEA (12.9 mL, 0.0744 mol) and reaction mixture was stirred for 10 minutes. Methylamine hydrochloride (1.8 g, 0.0273 mol) was added and the reaction mixture was stirred for 12 h. After completion of reaction, the solvent was concentrated and the residue was diluted with water (400 mL). The product was extracted with ethyl acetate (2×200 mL) and the combined organic layers were washed with brine solution (50 mL), dried over sodium sulphate and concentrated to provide 4-bromo-N-methylbenzamide as a white solid. Yield: 5 g (94.3%).

Synthesis of N-methyl-4-(4, 4, 5, 5-tetramethyl-1, 3, 2-dioxaborolan-2-yl) benzamide (9)

To a stirred solution of 4-bromo-N-methylbenzamide compound (4.00 g, 0.0186 mol) in 1,4-dioxane (10 mL) was added bis(pinacolato)diboron (11.3 g, 0.0448 mol), potassium acetate (5.30 g, 0.0541 mol) and [1,1-bis(diphenylphosphino)ferrocene]-dichloropalladium(II) (0.305 g, 0.00037 mol). After stirring at 90° C. for overnight the mixture was filtered through celite and concentrated. The residue was purified by flash chromatography over silica using a 40% ethyl acetate in pet ether as eluent to afford N-methyl-4-(4,4,5,5-tetramethyl-1,3,2-dioxaborolan-2-yl) benzamide as a white solid. Yield: 4.50 g (91%).

Synthesis of 4'-hydroxy-N-methyl[1,1'-biphenyl]-4-carboxamide (11)

To a stirred solution of N-methyl-4-(4,4,5,5-tetramethyl-1,3,2-dioxaborolan-2-yl)benzamide (5.12 g, 0.0196 mol) in 1,4-dioxane (60 mL) and water (4 mL), was added 4-bromo phenol (3.4 g, 0.0196 mol). The resulting solution was purged with nitrogen for 15 minutes. Then added sodium carbonate (6.23 g, 0.058 mol) and Bis(triphenylphosphine) palladium(II) dichloride (0.79 g, 0.0009 mol). After stirring at 100° C. for overnight, the mixture was cooled to room temperature and diluted with ethyl acetate. The reaction mixture was filtered through celite and concentrated. The crude product was purified by flash column chromatography using 40% ethyl acetate in pet ether to afford 4'-hydroxy-N-methyl-[1,1'-biphenyl]-4-carboxamide as an off-white solid. Yield: 4 g (90.9%).

Synthesis of 4'4(3-(benzyloxy)-6-(chloromethyl)-4-oxo-4H-pyran-2-yl)methoxy)-N-methyl-[1,1'-biphenyl]-4-carboxamide (5)

To a solution of 4'-hydroxy-N-methyl-[1,1'-biphenyl]-4-carboxamide (600 mg, 0.002 mol) in dry THF (10 mL) was added 3-(benzyloxy)-6-(chloromethyl)-2-(hydroxymethyl)-4H-pyran-4-one (0.88 g, 0.00317 mol) and triphenylphosphine (1 g, 0.00312 mol). The reaction mixture was cooled to 0° C. and DEAD (0.7 mL, 0.00468 mol) was added dropwise. The resulting solution was stirred at room temperature for overnight. After completion of the reaction, diluted with water (100 mL) and extracted with ethyl acetate (2×100 mL). The combined organic layers were dried over sodium sulphate and concentrated under reduced pressure. The crude product was purified by flash chromatography by using 30% ethyl acetate in pet ether to give 4'-((3-(benzyloxy)-6-(chloromethyl)-4-oxo-4H-pyran-2-yl) methoxy)-N-methyl-[1,1'-biphenyl]-4-carboxamide as an off-white solid. Yield: 440 mg (36%).

Synthesis of 4'-((3-(benzyloxy)-6-((methylsulfonyl) methyl)-4-oxo-4H-pyran-2-yl)methoxy)-N-methyl-[1,1'-biphenyl]-4-carboxamide (6)

A suspension of 4'-((3-(benzyloxy)-6-(chloromethyl)-4-oxo-4H-pyran-2-yl)methoxy)-N-methyl[1,1'-biphenyl]-4-carboxamide (440 mg, 0.00089 mol) and sodium methanesulfinate (91 mg, 0.00089 mol) in DMF (8 mL) was irradiated in a microwave reactor at 120° C. for 30 minutes. Then reaction mixture was cooled to room temperature and water was added to get 4'-((3-(benzyloxy)-6-((methylsulfonyl)methyl)-4-oxo-4H-pyran-2-yl)methoxy)-N-methyl-[1, 1'-biphenyl]-4-carboxamide as an off-white solid. Yield: 230 mg (48%).

Synthesis of 4'-((3-hydroxy-6-((methylsulfonyl) methyl)-4-oxo-4H-pyran-2-yl) methoxy)-N-methyl-[1,1'-biphenyl]-4-carboxamide procedure (Compound 8)

A solution of 4'-((3-(benzyloxy)-6-((methylsulfonyl) methyl)-4-oxo-4H-pyran-2-yl)methoxy)-N-methyl-[1,1'-biphenyl]-4-carboxamide (230 mg, 0.00043 mol) in a mixture of AcOH:HCl:TFA (3 mL: 3 mL: 0.3 mL) was heated to 80° C. for overnight. After completion of the reaction, the reaction mixture was cooled to room temperature and concentrated under vacuum. The residue was diluted with ice water to get Compound 8 as an off-white solid. The crude product was purified by Prep. HPLC purification. Yield: 30 mg (15%). $^1$H NMR (400 MHz, DMSO-d6, δ): 2.80 (d, J=4.40 Hz, 3H), 3.11 (s, 3H), 4.67 (s, 2H), 5.14 (s, 2H), 6.66 (s, 1H), 7.14 (d, J=8.80 Hz, 2H), 7.68-7.73 (m, 4H), 7.89 (d, J=8.40 Hz, 2H), 8.46 (s, 1H), 9.90 (s, 1H). MS (ES) (M+H)$^+$: 444.1 for $C_{22}H_{21}NO_7S$.

Synthesis of Compound 9

Figure 17:
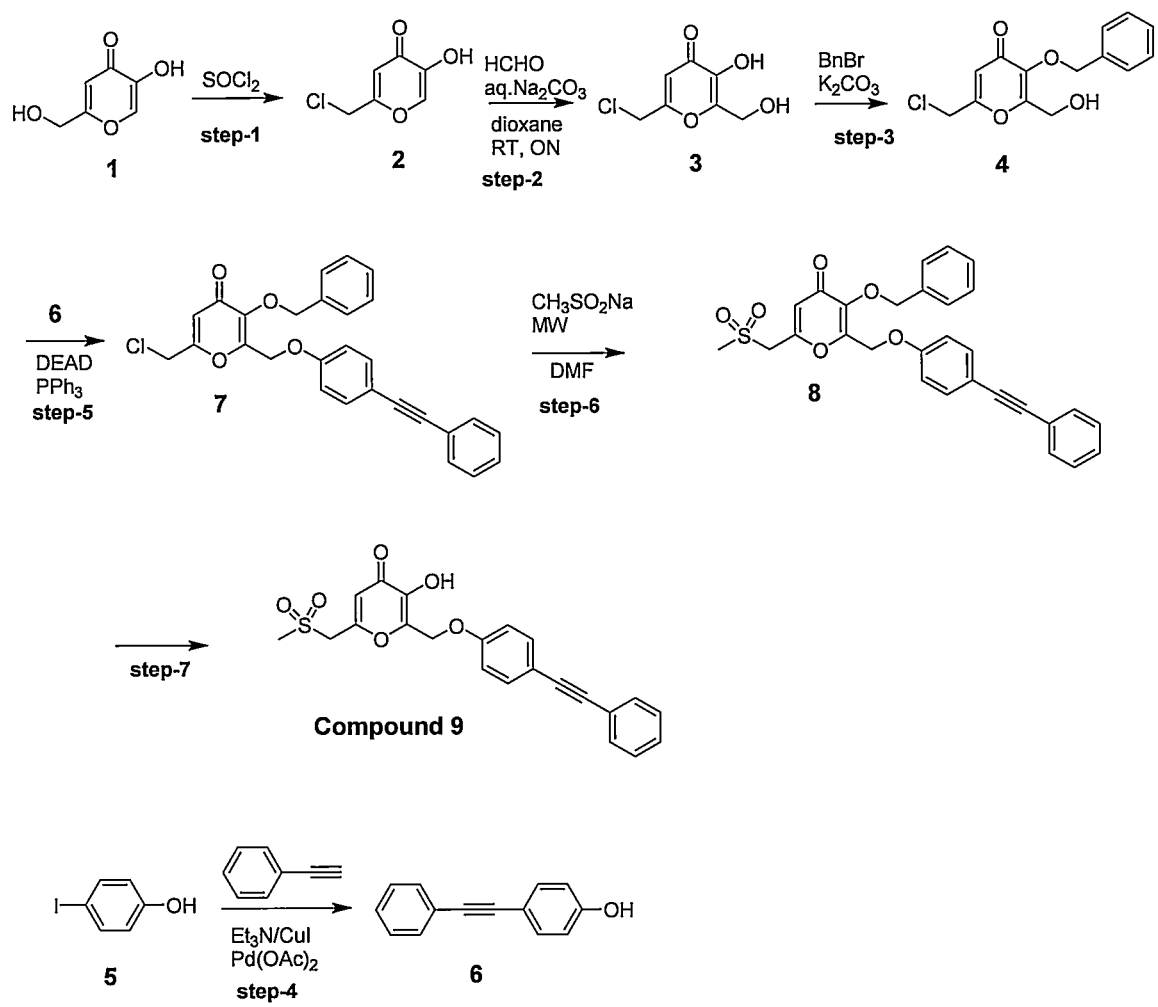
FIG. 17 shows a synthetic scheme to prepare compound 9.

The synthetic scheme to prepare compound 9 is shown in FIG. 17.

Synthesis of 2-(chloromethyl)-5-hydroxy-4H-pyran-4-one (2)

To a vigorously stirring suspension of kojic acid (25 g, 0.17 mol) in DCM (100 mL) was added thionyl chloride (20 g, 12.8 mL, 0.17 mol) at room temperature and the stirring was continued for 4 hours. The product precipitates as an off white solid which was filtered and washed with petroleum ether. Yield: 21 g (73%).

Synthesis of 6-(chloromethyl)-3-hydroxy-2-(hydroxymethyl)-4H-pyran-4-one (3)

To a stirred solution of chlorokojic acid (11.0 g, 0.068 mol) in dioxane (60 mL) was added $Na_2CO_3$ (8.0 g, 0.075 mol) in water (5 mL) and 41% w/v formaldehyde solution (6.2 g, 0.076 mol) and the reaction mixture was stirred at room temperature for overnight. After completion of the reaction, the solvent was evaporated under reduce pressure, diluted with water (100 mL) and $P^H$ was adjusted to 7-8 using 10% NaOH solution (5 mL). The aqueous layer was extracted with ethyl acetate (2×250 mL) and the combined organic layers were washed with water (50 mL) and brine (50 mL), dried over sodium sulphate, concentrated under reduced pressure to give 6-(chloromethyl)-3-hydroxy-2-(hydroxymethyl)-4H-pyran-4-one as a brown liquid. The residue was taken for next step without purification. (Crude yield 6 g, 46%).

Synthesis of 3-(benzyloxy)-6-(chloromethyl)-2-(hydroxymethyl)-4H-pyran-4-one (4)

To a stirred solution of 6-(chloromethyl)-3-hydroxy-2-(hydroxymethyl)-4H-pyran-4-one (6.0 g, 0.063 mol) in DMF (50 mL) was added $K_2CO_3$ (8.7 g, 0.063 mol) and benzyl bromide (7.7 mL, 0.063 mol) and the reaction mixture was stirred at room temperature for 6 h. After completion of the reaction, the solvent was evaporated under reduce pressure, diluted with water and extracted with ethyl acetate (2×200 mL). The combined organic layer was washed with water (200 mL) and brine (50 mL), dried over sodium sulphate, concentrated under reduced pressure. The crude material was purified by flash column chromatography using 20% ethyl acetate in pet ether to provide 3-(benzyloxy)-6-(chloromethyl)-2-(hydroxymethyl)-4H-pyran-4-one. Yield: 3.8 g (43%).

Synthesis of 4-(2-phenylethynyl)phenol (6)

A mixture of 4-iodo phenol (3 g, 0.0136 mol) and phenyl acetylene (1.49 g, 0.0136 mol) in acetonitrile (40 mL) was taken in a sealed tube. The resulting solution was purged with nitrogen for 15 minutes. Copper(I) iodide (258 mg, 0.00136 mol) was added followed by triethylamine (0.58 mL, 0.0004 mol) and [Bis(diphenyl phosphine)ferrocene] palladium(II) dichloride (1.1 g, 0.0013 mol). The reaction mixture was stirred at room temperature for 16 h and diluted with ethyl acetate. The mixture was filtered through celite and concentrated. The residue was diluted with water and extracted with ethyl acetate (2×200 mL). The combined organic layers were dried over sodium sulphate and concentrated. The crude product was purified by flash column chromatography by using 30% ethyl acetate in pet ether to afford 4-(2-phenylethynyl) phenol as an off-white solid. Yield: 2.5 g (96%).

Synthesis of 2-((4-(2-phenylethynyl)phenoxy) methyl)-3-(benzyloxy)-6-(chloromethyl)-4H-pyran-4-one (7)

To a solution of 4-(2-phenylethynyl)phenol (800 mg, 0.0041 mol) in dry THF (10 mL) was added 3-(benzyloxy)-6-(chloromethyl)-2-(hydroxymethyl)-4H-pyran-4-one (1.2 g, 0.0045 mol) and triphenylphosphine (1.2 g, 0.0049 mol). The reaction mixture was cooled to 0° C. and DEAD (1.17 mL, 0.0074 mol) was added dropwise. The resulting solution was stirred at room temperature for overnight. After completion of the reaction, the mixture was diluted with water (100 mL) and extracted with ethyl acetate (2×100 mL). The combined organic layers were concentrated in vacuum and the residue was purified by flash chromatography using 30% ethyl acetate in pet ether to give 244-(2-phenylethynyl) phenoxy)methyl)-3-(benzyloxy)-6-(chloromethyl)-4H-pyran-4-one as an off-white solid. Yield: 600 mg (33%).

Synthesis of 2-((4-(2-phenylethynyl)phenoxy) methyl)-3-(benzyloxy)-6-((methylsulfonyl)methyl)-4H-pyran-4-one (8)

A suspension of 2((4-(2-phenylethynyl)phenoxy)methyl)-3-(benzyloxy)-6-(chloromethyl)-4H-pyran-4-one (600 mg, 0.0013 mol) and sodium methanesulfinate (147 mg, 0.00144 mol) in DMF (12 mL) was irradiated in a microwave reactor at 120° C. for 30 minutes. Then reaction mixture was cooled to room temperature and water was added to get 2-((4-(2-phenylethynyl) phenoxy) methyl)-3-(benzyloxy)-6-((methylsulfonyl)methyl)-4H-pyran-4-one as an off-white solid. Yield: 300 mg (46%).

Step-7: 2-((4-(2-phenylethynyl)phenoxy)methyl)-3-hydroxy-6-((methylsulfonyl)methyl)-4H-pyran-4-one procedure (Compound 9)

To a solution of 2-((4-(2-phenylethynyl) phenoxy) methyl)-3-(benzyloxy)-6-((methylsulfonyl)methyl)-4H-pyran-4-one (230 mg, 0.00043 mol) in DCM was added $BCl_3$ (2 mL, 0.00215 mol) at 0° C. and the reaction mixture was stirred at room temperature for 2 h. After completion of the reaction, the solvent was concentrated under vacuum. The residue was diluted with ice water and the precipitated solid was filtered. The crude product was further purified by Prep. HPLC to get Compound 9 as an off-white solid. Yield: 30 mg (15%). $^1$H NMR (400 MHz, DMSO-d6, δ): 3.10 (s, 3H), 4.66 (s, 2H), 5.12 (s, 2H), 6.55 (s, 1H), 7.08 (d, J=8.64 Hz, 2H), 7.40 (m, 3H), 7.51 (m, 3H), 9.91 (s, 1H). MS (ES) (M+H)$^+$: 411.0 for $C_{22}H_{18}O_6S$.

Synthesis of Compounds 56, 57, 58 and 59

Figure 18:
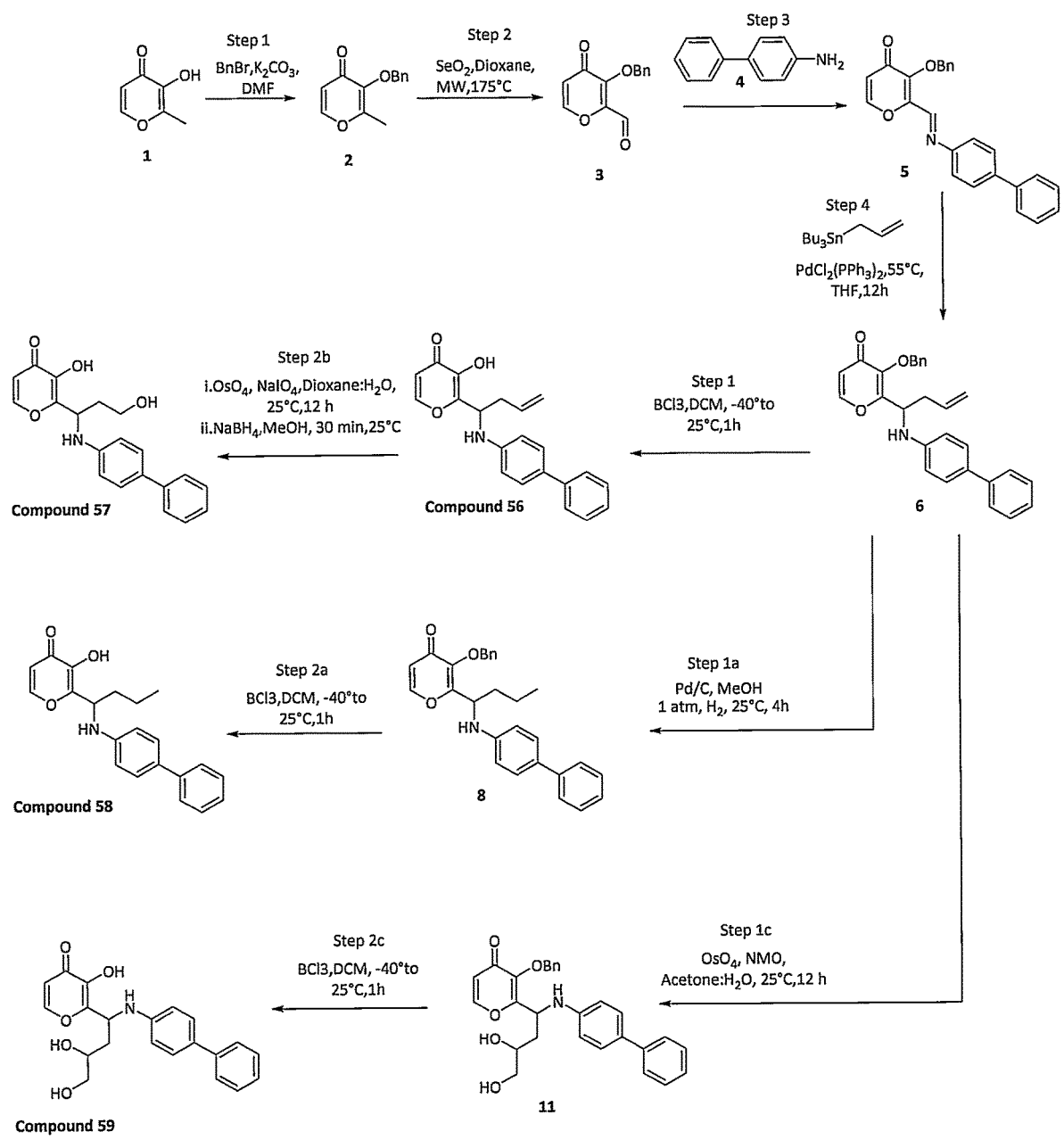
FIG. 18 shows a synthetic scheme to prepare compounds 56, 57, 58 and 59.

The synthetic scheme to prepare compounds 56, 57, 58 and 59 is shown in FIG. 18.

Synthesis of 3-(benzyloxy)-2-methyl-4H-pyran-4-one, 2

To a solution of 3-hydroxy-2-methyl-4H-pyran-4-one, 1 (30 g, 0.237 mol) dissolved in DMF (300 mL) were added $K_2CO_3$ (36.2 g, 0.261 mol) and benzyl bromide (40.7 g, 0.237 mol) and stirred at 80° C., for 2 h. After completion of the reaction, DMF was removed under reduced pressure and the crude product was diluted with water and EtOAc. The layers were separated and the aqueous layer was extracted with EtOAc. The combined organic layers were washed with brine solution and dried over anhydrous $Na_2SO_4$, filtered and concentrated to get 35 g (68%) of pure 3-(benzyloxy)-2-methyl-4H-pyran-4-one, 2. UPLC=Calculated for C13H12O3 216.24, Observed=217.1

Synthesis of 3-(benzyloxy)-4-oxo-4H-pyran-2-carbaldehyde, 3

To a solution of 3-(benzyloxy)-2-methyl-4H-pyran-4-one, 2 (2.0 g, 0.00924 mol) in 1,4-dioxane (12 mL), $SeO_2$ (0.23 g, 0.0018 mol) was added and microwaved for 1 h at 175° C. After completion of the reaction, the reaction mixture was filtered hot on celite bed and the filtrate was concentrated under reduced pressure. The crude product was purified by column chromatography to get 0.98 g (46%) of pure 3-(benzyloxy)-4-oxo-4H-pyran-2-carbaldehyde, 3. UPLC=Calculated for C13H10O4 230.22, Observed=231.1

Synthesis of (E)-2-(([1,1'-biphenyl]-4-ylimino) methyl)-3-(benzyloxy)-4H-pyran-4-one, 5

To a solution of 3-(benzyloxy)-4-oxo-4H-pyran-2-carbaldehyde, 3 (1.0 g, 0.0043 mol) and [1,1'-biphenyl]-4-amine (0.73 g, 0.0043 mol) in ethanol (20 mL) and catalytic amount of AcOH (0.5 mL) was added and stirred for 3 h at 25° C. After completion of the reaction, the solid precipitated was filtered and washed with diethyl ether and dried to get 1.3 g (81%) of pure (E)-2-(([1,1'-biphenyl]-4-ylimino)methyl)-3-(benzyloxy)-4H-pyran-4-one, 5. UPLC=Calculated for C25H19NO3 381.43, Observed=211.2

Synthesis of 2-(1-([1,1'-biphenyl]-4-ylamino)but-3-en-1-yl)-3-(benzyloxy)-4H-pyran-4-one 6

To a stirred solution of (E)-2-(([1,1'-biphenyl]-4-ylimino)methyl)-3-(benzyloxy)-4H-pyran-4-one, 5 (0.5 g, 0.0013 mol) in THF (10 mL), allyl tributyltin (0.52 g, 0.00157 mol) and PdCl$_2$(PPh$_3$)$_2$ (0.046 g, 0.0000656 mol) were added and stirred at 55° C. for 12 h. After completion of the reaction, the reaction mixture was diluted with water and ethyl acetate, layers were separated and aqueous layer was extracted with EtOAc. The combined organic layers were washed with brine solution and dried over anhydrous Na$_2$SO$_4$, filtered and concentrated. The crude product was triturated with pet. ether and dried to get 0.45 g (82%) of pure 2-(1-([1,1'-biphenyl]-4-ylamino)but-3-en-1-yl)-3-(benzyloxy)-4H-pyran-4-one, 6. LCMS=Calculated for C28H25NO3 423.51, Observed=424.3

Synthesis of 2-(1-([1,1'-biphenyl]-4-ylamino)but-3-en-1-yl)-3-hydroxy-4H-pyran-4-one, (Compound 111)

To a cooled solution of 2-(1-([1,1'-biphenyl]-4-ylamino)but-3-en-1-yl)-3-(benzyloxy)-4H-pyran-4-one, 6 (0.1 g, 0.00023 mol) dissolved in DCM (3 mL), BCl$_3$ (1M in DCM, 0.7 mL, 0.00069 mol) was added slowly at −40° C. and gradually allowed to stir at 25° C. for 1 h. After completion of the reaction, the reaction mixture was carefully quenched with MeOH (2 mL) and stirred for 10 min. After 10 min, solvents were removed under reduced pressure and the crude product was triturated with diethyl ether to get 0.074 g (95%) of pure 2-(1-([1,1'-biphenyl]-4-ylamino)but-3-en-1-yl)-3-hydroxy-4H-pyran-4-one, 7(FRG 084a). UPLC=Calculated for C21H19NO3 333.39, Observed=334.3

Synthesis of 2-(1-([1,1'-biphenyl]-4-ylamino)butyl)-3-(benzyloxy)-4H-pyran-4-one, 8

To a solution of 2-(1-([1,1'-biphenyl]-4-ylamino)but-3-en-1-yl)-3-(benzyloxy)-4H-pyran-4-one, 6 (0.1 g, 0.00023 mol) in methanol and THF (5 mL), 10% palladium on carbon (20 mg) was added and stirred at 1 atm H$_2$ bladder pressure at 25° C. for 6 h. After completion of the reaction, the reaction mixture was filtered on celite bed and filtrate was concentrated under reduced pressure. The crude product was purified by column chromatography to get 0.076 g (72%) of pure 2-(1-([1,1'-biphenyl]-4-ylamino)butyl)-3-(benzyloxy)-4H-pyran-4-one, 8. UPLC=Calculated for C28H27NO3 425.53, Observed=426.4

Synthesis of 2-(1-([1,1'-biphenyl]-4-ylamino)butyl)-3-hydroxy-4H-pyran-4-one, (Compound 113)

To a cooled solution of 2-(1-([1,1'-biphenyl]-4-ylamino)butyl)-3-(benzyloxy)-4H-pyran-4-one, 8 (0.07 g, 0.00016 mol) dissolved in DCM (3 mL), BCl$_3$ (1M in DCM, 0.49 mL, 0.00049 mol) was added slowly at −40° C. and gradually allowed to stir at 25° C. for 1 h. After completion of the reaction, the reaction mixture was carefully quenched with MeOH and stirred for 10 min. After 10 min, solvents were removed under reduced pressure and the crude product was triturated with diethyl ether to get 0.052 g (96%) of pure 2-(1-([1,1'-biphenyl]-4-ylamino)butyl)-3-hydroxy-4H-pyran-4-one, 9 (FRG_084 Propyl). UPLC=Calculated for C21H21NO3 335.40, Observed=336.3

2-(1-([1,1'-biphenyl]-4-ylamino)-3-hydroxypropyl)-3-hydroxy-4H-pyran-4-one, (Compound 112)

To a stirred solution of 2-(1-([1,1'-biphenyl]-4-ylamino)but-3-en-1-yl)-3-hydroxy-4H-pyran-4-one, 7 (0.05 g, 0.00014 mol) in 1, 4-dioxane (5 mL), OsO$_4$ (2.5% in t-butanol, 0.15 mL, 0.000014 mol) was added followed by solution of NaIO$_4$ (0.074 g, 0.00035 mol) in water (1 mL) and stirred at 25° C. for 4 h. After completion of the reaction, the reaction mixture was diluted with water and EtOAc, layers were separated and the aqueous layer was extracted with EtOAc. The combined organic layers were washed with brine solution and dried over anhydrous Na$_2$SO$_4$, filtered and concentrated. The crude product was dissolved in MeOH (3 mL) and cooled to 0° C. To this cooled reaction mixture NaBH$_4$ (50 mg) was added and stirred for 10 min. The reaction mixture was quenched with sat NH$_4$Cl and methanol was removed and extracted with EtOAc. The organic layer was dried over anhydrous Na$_2$SO$_4$, filtered and concentrated under reduced pressure and the crude product was purified by prep TLC to get 0.01 g (21.2%) of pure 2-(1-([1,1'-biphenyl]-4-ylamino)-3-hydroxypropyl)-3-hydroxy-4H-pyran-4-one, 10 (FRG_085). LCMS=Calculated for C20H19NO4 337.38, Observed=338.2

Synthesis of 2-(1-([1,1'-biphenyl]-4-ylamino)-3,4-dihydroxybutyl)-3-(benzyloxy)-4H-pyran-4-one, 11

To a stirred solution of 2-(1-([1,1'-biphenyl]-4-ylamino)but-3-en-1-yl)-3-(benzyloxy)-4H-pyran-4-one, 6 (0.1 g, 0.00023 mol) in acetone (4 mL) and water (0.5 mL). OsO$_4$ (2.5% in t-butanol, 0.24 mL, 0.000023 mol) was added followed N-methylmorpholine-N-Oxide (0.03 g, 0.00283 mol) and stirred at 25° C. for 12 h. After completion of the reaction, the reaction mixture was diluted with water and EtOAc, layers were separated and the aqueous layer was extracted with EtOAc. The combined organic layers were washed with brine solution and dried over anhydrous Na$_2$SO$_4$, filtered and concentrated. The crude product was triturated with diethylether to get 0.097 g (90%) of pure 2-(1-([1,1'-biphenyl]-4-ylamino)-3,4-dihydroxybutyl)-3-(benzyloxy)-4H-pyran-4-one, 11. LCMS=Calculated for C28H27NO5 457.53, Observed=458.3

Synthesis of 2-(1-([1,1'-biphenyl]-4-ylamino)-3,4-dihydroxybutyl)-3-hydroxy-4H-pyran-4-one, (Compound 114)

To a cooled solution of 2-(1-([1,1'-biphenyl]-4-ylamino)-3,4-dihydroxybutyl)-3-(benzyloxy)-4H-pyran-4-one, 11

(0.08 g, 0.00017 mol) in DCM (3 mL), BCl₃ (1M in DCM, 0.52 mL, 0.00052 mol) was added slowly at −40° C. and gradually allowed to stir at 25° C. for 1 h. After completion of the reaction, the reaction mixture was carefully quenched with MeOH and stirred for 10 min. After 10 min solvents were removed under reduced pressure and the crude product was triturated with diethyl ether to get 0.06 g (95%) of pure 2-(1-([1,1'-biphenyl]-4-ylamino)-3,4-dihydroxybutyl)-3-hydroxy-4H-pyran-4-one, FRG 088. LCMS=Calculated for C21H21NO5 367.40, Observed=368.2 Synthesis of Compound 61

Figure 19:
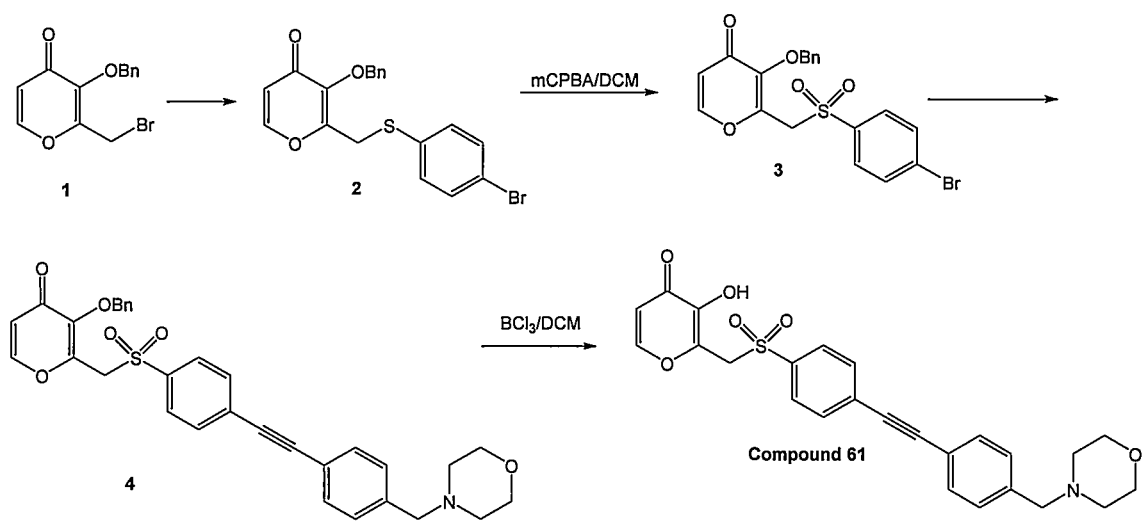
FIG. 19 shows a synthetic scheme to prepare compound 61.

The synthetic scheme to prepare compound 61 is shown in FIG. 19.

Synthesis of 3-(benzyloxy)-2-(((4-bromophenyl)thio)methyl)-4H-pyran-4-one (2)

3-(benzyloxy)-2-(bromomethyl)-4H-pyran-4-one1 (255 mgs, 0.87 mmol) and 4-bromobenzenethiol (164 mg, 0.87 mmol) in 3 mL of THF was refluxed for 5 hr and was left at room temperature overnight. After removal of solvent, the product was purified via column chromatography (e/h 1/3) to give 335 mgs of oil as product 2.

Synthesis of 3-(benzyloxy)-2-(((4-bromophenyl)sulfonyl)methyl)-4H-pyran-4-one (3)

335 mgs of product 2 was dissolved in 5 mL of DCM. mCPBA (205 mgs) was added. The oxidation reaction proceeded for 2 hrs at room temperature. Compound 3 was purified via column chromatography (e/h 1/1) to give 229 mgs of white solids as 3.

Synthesis of 3-(benzyloxy)-2-(((4-((4-(morpholinomethyl)phenyl)ethynyl) phenyl)sulfonyl)methyl)-4H-pyran-4-one (4)

Product 3 (50 mgs, 0.115 mmol) was dissolved in 1 mL of 1,4-dioxane. To this was added cat. Amount of CuI, PdCl2(PPh3)2, and diisopropylethylamine. 4-(4-ethynylbenzyl)morpholine (25 mgs, 1.1 eq) was added. The system was flushed with N2 and was subject to microwave irradiation at 100° C. for 30 mins. Solvent was removed and the residue was purified via column chromatography (e/h 1/1) to give 57 mgs of white solids as product 4. LC/MS M++1 556.

Synthesis of 3-hydroxy-2-(((4-((4-(morpholinomethyl)phenyl)ethynyl)phenyl)sulfonyl)methyl)-4H-pyran-4-one (Compound 61)

Product 4 (27 mgs) was dissolved in 1 mL of DCM. BCl3 (3 eq, 1M in DCM) was added at 0° C. After 1 hr, MeOH was added to quench the excess of BCl3. Solvent was removed and the product was purified via reverse phase column to give 12 mgs of final product as TFA salt, white solids. LC/MS M++1 466

Example 2: In Vitro Assays to Screen Compounds and Metalloprotein Modulators

Bacterial Susceptibility Testing

Minimal inhibitory concentrations (MIC) were determined by the broth microdilution method in accordance with the Clinical and Laboratory Standards Institute (CLSI) guidelines. In brief, organism suspensions were adjusted to a 0.5 McFarland standard to yield a final inoculum between $3\times10^5$ and $7\times10^5$ colony-forming units (CFU)/mL. Drug dilutions and inocula were made in sterile, cation adjusted Mueller-Hinton Broth (Beckton Dickinson). An inoculum volume of 100 μL was added to wells containing 100 μL of broth with 2-fold serial dilutions of drug. All inoculated microdilution trays were incubated in ambient air at 35° C. for 18-24 h. Following incubation, the lowest concentration of the drug that prevented visible growth (OD600 nm<0.05) was recorded as the MIC. Performance of the assay was monitored by the use of laboratory quality-control strains and levofloxacin, a compound with a defined MIC spectrum, in accordance with CLSI guidelines.

TABLE 2

Exemplary in vitro assay data against select bacteria for compounds in embodiments of the disclosure.

| | E. coli ATCC 25922- no FBS | E.coli BW25113- no FBS | E. coli imp mutant | E. coli delta tolC | S. aureus ATCC 29213 | P. aeruginosa 209 | P. aeruginosa 210 delta mexAB-OprM |
|---|---|---|---|---|---|---|---|
| 27 | D | D | D | D | D | D | D |
| 46 | C | B | B | A | D | D | D |
| 4 | B | N.D. | C | A | D | N.D. | N.D. |
| 50 | B | B | N.D. | N.D. | N.D. | N.D. | N.D. |
| 32 | B | B | B | A | D | D | D |
| 5 | C | B | B | B | D | D | D |
| 44 | B | B | A | A | D | D | C |
| 7 | D | D | D | D | D | D | D |
| 48 | B | B | B | A | D | D | C |
| 29 | D | D | D | D | D | D | D |
| 9 | D | D | C | C | C | D | D |
| 11 | D | N.D. | N.D. | N.D. | B | D | N.D. |
| 2 | D | D | D | C | D | D | D |
| 28 | B | B | B | B | D | D | D |
| 38 | B | A | A | A | D | D | C |
| 30 | D | D | B | D | C | D | D |
| 35 | B | B | B | A | D | D | D |
| 41 | B | B | B | A | D | D | C |
| 53 | D | D | D | B | D | D | D |
| 34 | B | B | B | A | D | D | D |
| 42 | B | B | B | A | D | D | C |

TABLE 2-continued

Exemplary in vitro assay data against select bacteria for compounds in embodiments of the disclosure.

| | E. coli ATCC 25922- no FBS | E.coli BW25113- no FBS | E. coli imp mutant | E. coli delta tolC | S. aureus ATCC 29213 | P. aeruginosa 209 | P. aeruginosa 210 delta mexAB-OprM |
|---|---|---|---|---|---|---|---|
| 36 | C | B | B | A | D | D | D |
| 37 | B | B | B | A | D | D | D |
| 31 | D | D | D | B | D | D | D |
| 40 | B | B | A | A | D | D | C |
| 54 | D | D | D | C | D | D | D |
| 51 | B | B | B | A | D | D | D |
| 43 | B | B | B | A | D | D | C |
| 8 | D | D | D | D | D | D | D |
| 45 | B | B | A | A | D | D | C |
| 1 | D | D | D | D | D | D | D |
| 47 | C | B | B | B | D | D | D |
| 49 | B | B | B | A | D | D | D |
| 39 | B | B | B | A | D | D | C |
| 3 | D | D | D | C | D | D | D |
| 52 | D | D | D | D | D | D | D |
| 6 | D | D | D | D | D | D | D |
| 33 | C | B | B | A | D | D | D |
| 55 | B | B | B | B | D | D | C |

The MIC values in the table are as follows: A=less than 1 µg/mL; B=1 to 8 µg/mL; C=greater than 8 to 32 µg/mL; D=greater than 32 µg/mL; and N.D. means no data. FBS=fetal bovine serum.

Inhibition Assay Against *Klebsiella pneumonae* LpxC

LpxC inhibition assays were performed using liquid chromatography with tandem mass spectrometry. Assays were performed, in duplicate, in opaque, 96-well microplates in a total assay volume of 50 µL. The incubation mixture contained: LpxC (0.2 nM Kpn), 0.8 µM UDP-3-O—[(R)-3-hydroxymyristoyl]-N-acetyl-glucosamine, 40 mM Bis-Tris/HCl buffer (pH 5.9), 5 mM sodium phosphate buffer ($NaH_2PO_4/Na_2HPO_4$, pH 7.0), 1 mM DTT, 0.1% (w/v) fatty-acid free BSA, 10% DMSO (v/v, with or without compound). The reactions were incubated at 22° C. for 60 minutes (with mild shaking), then terminated by the addition of 25 µL 0.25 N HCl. Samples were analyzed using a LC-MS system to measure native LpxC substrate and reaction product. $IC_{50}$ analysis was done using GeneData Screener and a four parameter variable slope normalized to controls. Test compounds were prepared as 8-point dose-response curves (factor dilution 2) in triplicate, starting at 1 µM final concentration. Each assay plate included 6 wells used for the Z' factor calculation, 3 as a positive control for the assay and 3 as a negative control. The robustness was calculated as the median Z' factor for 5 plates. CHIR-090, a well-known inhibitor of LpxC activity was used as inhibitor control standard.

The dose response curves for a known LpxC inhibitor CHIR-090 and exemplary compounds of the disclosure are shown in FIGS. 1-9.

The RZ' factor obtained for this experiment (0.8324) indicates excellent assay quality in terms of signal dynamic range and data variation. The $IC_{50}$ value of 0.47 nM calculated for the CHIR-090 inhibitor is consistent with previously reported values.

TABLE 3

Exemplary in vitro assay data against *Klebsiella pneumoniae* for compounds in embodiments of the disclosure.

| Compound ID No. | $IC_{50}$ (nM) |
|---|---|
| 40 | C |
| 39 | C |
| 32 | C |
| 47 | C |
| 4 | D |
| 35 | D |
| 28 | D |
| 38 | D |
| CHIR-090 | A |

For the enzyme potency, $IC_{50}$ values against *Klebsiella pneumoniae* in the table are as follows: A=less than 1 nM; B=1 to less than 10 nM; C=10 to 100 nM; D=greater than 100 nM; and N/D means no data.

Example 3: Treatment for Bacterial Infections

Human Clinical Trial of the Safety and/or Efficacy of Pyrone Based Compounds for Treating Patients with cUTI, cIAI, HAP, or VAP Objective: To compare the safety of administered composition comprising compound 36, 38, 42, 45, or 48.

Study Design: This will be an observational, cohort study from medical chart review of adult hospitalized patients for each of the three conditions of interest (complicated urinary tract infection (cUTI), complicated intra-abdominal infection (cIAI) and nosocomial pneumonia (NP) including hospital acquired pneumonia (HAP) and ventilator-associated pneumonia (VAP)). For this study, the proposed patient selection period extends for 12 months. Patients selected during this period will be followed from diagnosis (i.e., diagnosis of cUTI, cIAI or NP) until symptom resolution, discharge or 30-days post discharge [based on data availability to assess readmission and outpatient visits], death while hospitalized, loss to follow-up or the end of study period if not yet discharged from index hospitalization.

Study Population: Adult (18 years or older) patients with diagnosis of at least one of the following conditions: urinary tract infection, intra abdominal infection, hospital acquired pneumonia, or ventilator associated pneumonia.

Phase I: Patients receive pharmaceutical compositions of compound 36, 38, 42, 45, or 48, each day of a 28-day cycle. Doses of compound 36, 38, 42, 45, or 48 may be held or modified for toxicity based on medical assessment. Treatment repeats every 28 days in the absence of unacceptable toxicity. Cohorts of 3-6 patients receive escalating doses of the compound until the maximum tolerated dose (MTD) for the compound is determined. The MTD is defined as the dose preceding that at which 2 of 3 or 2 of 6 patients experience dose-limiting toxicity.

Phase II: Patients receive compound 36, 38, 42, 45, or 48 as in phase I at the MTD determined in phase I. Treatment repeats every 4 weeks for 2-6 courses in the absence of infection progression or unacceptable toxicity. After completion of 2 courses of study therapy, patients who achieve a complete or partial response may receive an additional 4 courses. Patients who maintain stable infections for more than 2 months after completion of 6 courses of study therapy may receive an additional 6 courses at the time of infection progression, provided they meet original eligibility criteria.

Testing: Tests that will be used to monitor the effectiveness of the treated medical device include: physical exam, X-ray, urinalysis, blood work and other clinical laboratory methodologies used to detect pathogens in the patients.

EQUIVALENTS AND SCOPE

It is, therefore, to be understood that the foregoing embodiments are presented by way of example only and that, within the scope of the appended claims and equivalents thereto, the present teachings may be practiced otherwise than as specifically described and claimed using no more than routine experimentation. The present teachings are directed to each individual feature and method described herein. In addition, any combination of two or more such features and methods, if such features and methods are not mutually inconsistent, is included within the scope of the present teachings. Such equivalents are intended to be encompassed by the scope of the following claims.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise. All cited sources, for example, references, publications, databases, database entries, and art cited herein, are incorporated into this application by reference, even if not expressly stated in the citation. In case of conflicting statements of a cited source and the instant application, the statement in the instant application shall control.

What is claimed is:
1. A compound of Formula VIII:

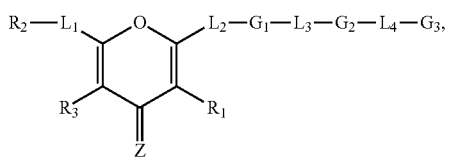

or a pharmaceutically acceptable salt thereof, wherein:
$R_1$ is —OH, —NH$_2$, or SH;
$R_2$ is H;
$R_3$ is H or $C_{1-6}$ alkyl;
Z is O or S;
$L_1$ is a bond;
$L_2$ is a bivalent radical selected from —$(C(R_4)(R_5))_n$—$(C_{0-3}$ alkylene)-, —$(C(R_4)(R_5))_n$—$C_{0-3}$ alkylene)-(CH—OR$^c$)—, —$(C(R_4)(R_5))_n$—$(C_{0-3}$ alkylene)-C(=O)—, —$(C(R_4)(R_5))_n$—$(C_{0-3}$ alkylene)-C(=N—OH)—, —$(C(R_4)(R_5))_n$—$(C_{0-3}$ alkylene)-(C(=O)NR$_5$)—, —$(C(R_4)(R_5))_n$—$(C_{0-3}$ alkylene)-N(R$_5$)C(=O)—, —$(C(R_4)(R_5))_n$—$(C_{0-3}$ alkylene)-O—, —$(C(R_4)(R_5))_n$—$(C_{0-3}$ alkylene)-N(R$_5$)—, —$(C(R_4)(R_5))_n$—$(C_{0-3}$ alkylene)-S(=O)$_2$—, —$(C(R_4)(R_5))_n$—$(C_{0-3}$ alkylene)-S(=O)$_2$N(R$_5$)—, or —$(C(R_4)(R_5))_n$—$(C_{0-3}$ alkylene)-N(R$_5$)S(=O)$_2$—;

wherein each $R_4$ is H or optionally substituted $C_{1-6}$ alkyl; and
each $R_5$ is independently H, an optionally substituted $C_{1-6}$ alkyl, an optionally substituted $C_{2-6}$ alkenyl, an optionally substituted $C_{2-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —$(C_{0-4}$ alkylene)-OR$^f$, —$(C_{0-4}$ alkylene)-$(C_{2-4}$ alkene), —$(C_{0-4}$ alkylene)-$(C_{2-4}$ alkyne), $C_2$-$C_7$ heterocycle, —$(C_{0-4}$ alkylene)-C(=O)—$(C_1$-$C_6$ alkyl), —$(C_{0-4}$ alkylene)-C(=O)H, —$(C_{0-4}$ alkylene)-C(=O)OR$^f$, —$(C_{0-4}$ alkylene)-CN, —$(C_{0-4}$ alkylene)-halo, —$(C_{0-4}$ alkylene)-NO$_2$, —$(C_{0-4}$ alkylene)-N(R$^f$)$_2$, —$(C_{0-4}$ alkylene)-S(=O)$_2$—(R$^f$), —$(C_{0-4}$ alkylene)-$(C_{6-14}$ aryl), —$(C_{1-4}$ alkylene)-(5- to 14-membered heteroaryl), —$(C_{0-4}$ alkylene)-C(=O)NR$^b$R$^f$ or —$(C_{0-4}$ alkylene)-NR$^b$C(=O)R$^f$;

wherein each R$^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$L_3$ is a bivalent radical —$(C_{2-6}$ alkynylene)-;
$L_4$ is a bivalent radical selected from a bond, —C(=O)—, —C(=O)O—, —C(=O)NR$^e$—, —N(R$^e$)C(=O)—, or —$(C_{1-4}$ alkylene)-;
$G_1$ and $G_2$ are each independently, at each occurrence, a bivalent radical selected from —$(C_{6-14}$ arylene)- or -(5- to 14-membered heteroarylene)-;
$G_3$ is H, $C_{1-6}$ alkyl, $C_{3-7}$ cycloalkyl, $C_{3-10}$ heterocycloalkyl, $C_{6-14}$ aryl, 5- to 14-membered heteroaryl, $(C_{1-4}$ alkylene)-$(C_{1-4}$ heteroalkyl), $(C_{3-10}$ heterocycloalkylene)-$(C_{1-4}$ alkyl), or $(C_{3-10}$ heterocycloalkylene)-$(C_{1-4}$ heteroalkyl);
R$^b$, R$^c$, and R$^e$ are each independently, at each occurrence, H or $C_{1-6}$ alkyl; and
n is 1 or 2.

2. The compound of claim 1, or a pharmaceutically acceptable salt thereof, wherein
$R_1$ is —OH;
$R_3$ is H or $C_{1-6}$ alkyl;
Z is O;
$L_2$ is a bivalent radical is selected from —$(C(R_4)(R_5))_n$—$(C_{0-3}$ alkylene), or —$C(R_4)(R_5))_n$—$(C_{0-3}$ alkylene)-N(R$_5$)—;
wherein each $R_4$ is H or $C_{1-6}$ alkyl;
each $R_5$ is independently H or $C_{1-6}$ alkyl;
$L_3$ is a bivalent radical —$(C_{2-6}$ alkynylene)-;
$L_4$ is a bivalent radical selected from a bond, —C(=O)—, —C(=O)O—, —C(=O)NR$^e$—, —N(R$^e$)C(=O)—, or —$(C_{1-4}$ alkylene)-;

G$_1$ and G$_2$ are each independently, at each occurrence, a bivalent radical selected from —(C$_{6-14}$ arylene)- or -(5- to 14-membered heteroarylene)-;

G$_3$ is H, C$_{1-6}$ alkyl, C$_{3-7}$ cycloalkyl, C$_{3-10}$ heterocycloalkyl, C$_{6-14}$ aryl, 5- to 14-membered heteroaryl, (C$_{1-4}$ alkylene)-(C$_{1-4}$ heteroalkyl), (C$_{3-10}$ heterocycloalkylene)-(C$_{1-4}$ alkyl), or (C$_{3-10}$ heterocycloalkylene)-(C$_{1-4}$ heteroalkyl);

R$^c$ and R$^e$ are each independently, at each occurrence, H or C$_{1-6}$ alkyl; and n is 1 or 2.

3. The compound of claim 1, or a pharmaceutically acceptable salt thereof, wherein L$_2$ is a bivalent radical selected from —(C(R$_4$)(R$_5$))$_n$—(C$_{0-3}$ alkylene)-C(=O)NR$_5$)—, —(C(R$_4$)(R$_5$))$_n$—(C$_{0-3}$ alkylene)-N(R$_5$)C(=O)—, or —(C(R$_4$)(R$_5$))$_n$—(C$_{0-3}$ alkylene)-N(R$_5$)—;

L$_3$ is a bivalent radical —(C$_{2-6}$ alkynylene)-;

L$_4$ is a bivalent radical selected from a bond, —C(=O)—, —(C(=O)O)—, —(C(=O)NR$^e$)—, —N(R$^e$)C(=O)—, or —(C$_{1-4}$ alkylene)-;

G$_1$ and G$_2$ are each independently, at each occurrence, a bivalent radical selected from —(C$_6$ arylene)- or -(5- to 6-membered heteroarylene)-; and G$_3$ is H, C$_{1-6}$ alkyl, C$_{3-7}$ cycloalkyl, C$_{3-10}$ heterocycloalkyl, 5- to 6-membered heteroaryl, (C$_{1-4}$ alkylene)-(C$_{1-4}$ heteroalkyl), (C$_{3-10}$ heterocycloalkylene)-(C$_{1-4}$ alkyl), or (C$_{3-10}$ heterocycloalkylene)-(C$_{1-4}$ heteroalkyl).

4. A compound of Formula IX:

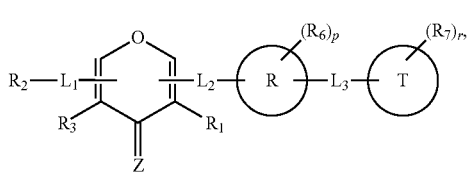

IX or a pharmaceutically acceptable salt thereof, wherein:

R$_1$ is H, C$_{1-6}$ alkyl, —OH, —NH$_2$, or SH;
R$_2$ is H;
R$_3$ is H, C$_{1-6}$ alkyl, —OH, —NH$_2$, or SH;
R$_6$ and R$_7$ are each independently, at each occurrence, —OH, —NH$_2$, —CN, —NO$_2$, —C(=O)OR$^b$, —C(=O) N(R$^b$)$_2$, —N(R$^b$)C(=O)OR$^b$, halo, C$_{1-6}$ alkyl, C$_{1-6}$ alkoxy, or =O;
ring R is C$_{3-7}$ cycloalkyl, C$_{3-10}$ heterocycloalkyl, C$_{6-14}$ aryl, or a 5- to 14-membered heteroaryl;
ring T is C$_{3-7}$ cycloalkyl, C$_{3-10}$ heterocycloalkyl, C$_{6-14}$ aryl, or a 5- to 14-membered heteroaryl;
Z is O or S;
L$_1$ is a bond;
L$_2$ is a bivalent radical selected from —(C(R$_4$)(R$_5$))$_n$—(C$_{0-3}$ alkylene)-, —(C(R$_4$)(R$_5$))$_n$—C$_{0-3}$ alkylene)-(CH—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-(C(=O)NR$_5$)—, —(C(R$_4$)(R$_5$))$_n$—(C$_{0-3}$ alkylene)-N(R$_5$)C(=O)—, —(C(R$_4$)(R$_5$))$_n$—(C$_{0-3}$ alkylene)-O—, or —(C(R$_4$)(R$_5$))$_n$—(C$_{0-3}$ alkylene)-N(R$_5$)—;
wherein each R$_4$ is H or optionally substituted C$_{1-6}$ alkyl; and
each R$_5$ is independently H, an optionally substituted C$_{1-6}$ alkyl, an optionally substituted C$_{2-6}$ alkenyl, an optionally substituted C$_{2-6}$ alkynyl, an optionally substituted C$_{6-14}$ aryl, an optionally substituted 5- to 14-membered heteroaryl, an optionally substituted C$_3$-C$_8$ cycloalkyl, on optionally substituted —(C$_{0-4}$ alkylene)-OR$^f$, —(C$_{0-4}$ alkylene)-(C$_{2-4}$ alkene), —(C$_{0-4}$ alkylene)-(C$_{2-4}$ alkyne), C$_2$-C$_7$ heterocycle, —(C$_{0-4}$ alkylene)-C(=O)—(C$_1$-C$_6$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene)-N(R$^f$)$_2$, —(C$_{0-4}$ alkylene)-S(=O)$_2$—(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)-C(=O)NR$^b$R$^f$ or —(C$_{0-4}$ alkylene)-NR$^b$C(=O)R$^f$;
wherein each R$^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;
L$_3$ is a bivalent radical;
R$^b$ and R$^c$ are each independently, at each occurrence, H or C$_{1-6}$ alkyl;
n is 1 or 2;
p is 0, 1, 2, or 3; and
r is 0, 1, 2, or 3,
provided that R$_1$ or R$_3$ is —OH, —NH$_2$, or SH.

5. A method of modulating the activity of UDP-{3-O—[(R)-3-hydroxymyristoyl]}-N-acetylglucosamine deacetylase in a subject in need thereof comprising administering a therapeutically effective amount of a compound of claim 1, or a pharmaceutically acceptable salt thereof.

6. A method of treating a gram-negative bacterial infection in a subject comprising administering to the subject a pharmaceutical composition comprising the compound of claim 1, or a pharmaceutically acceptable salt thereof.

7. A pharmaceutical composition comprising a therapeutically effective amount of the compound of claim 1, and a pharmaceutically acceptable excipient.

8. A method of modulating the activity of UDP-{3-O—[(R)-3-hydroxymyristoyl]}-N-acetylglucosamine deacetylase in a subject in need thereof comprising administering a therapeutically effective amount of a compound of claim 4, or a pharmaceutically acceptable salt thereof.

9. A method of treating a gram-negative bacterial infection in a subject comprising administering to the subject a pharmaceutical composition comprising the compound of claim 4, or a pharmaceutically acceptable salt thereof.

10. A pharmaceutical composition comprising a therapeutically effective amount of the compound of claim 4, and a pharmaceutically acceptable excipient.

11. The compound of claim 1, or a pharmaceutically acceptable salt thereof, having the structure of Formula VIIIC:

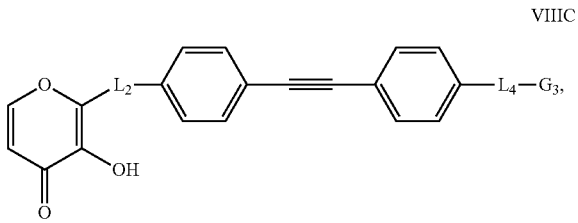

VIIIC or a pharmaceutically acceptable salt thereof.

12. The compound of claim 1, or a pharmaceutically acceptable salt thereof, having the structure of Formula VIIID:

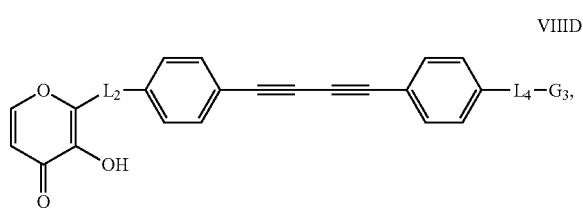

VIIID or a pharmaceutically acceptable salt thereof.

13. The compound of claim 1, or a pharmaceutically acceptable salt thereof, wherein $G_3$ is $C_{1-6}$ alkyl, $C_{3-7}$ cycloalkyl, $C_{3-10}$ heterocycloalkyl, 5- to 6-membered heteroarylene, $(C_{1-4}$ alkylene)-$(C_{1-4}$ heteroalkyl), $(C_{3-10}$ heterocycloalkylene)-$(C_{1-4}$ alkyl), or $(C_{3-10}$ heterocycloalkylene)-$(C_{1-4}$ heteroalkyl).

14. The compound of claim 1, selected from:

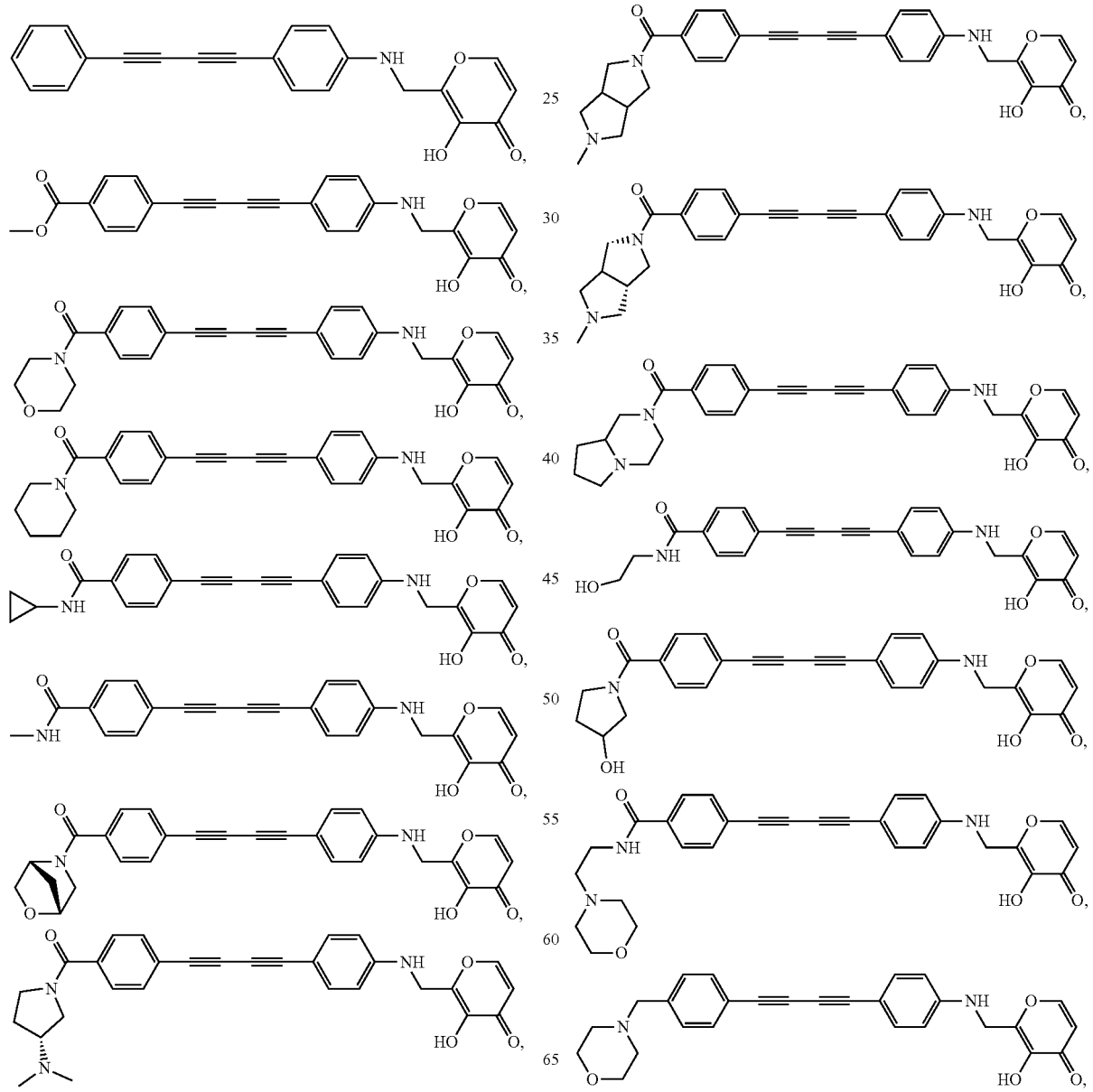

-continued
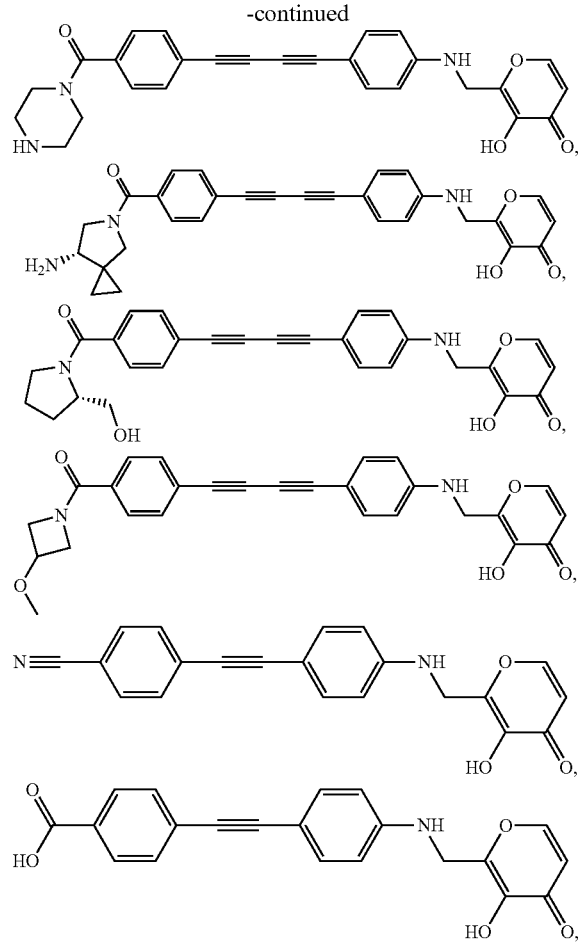
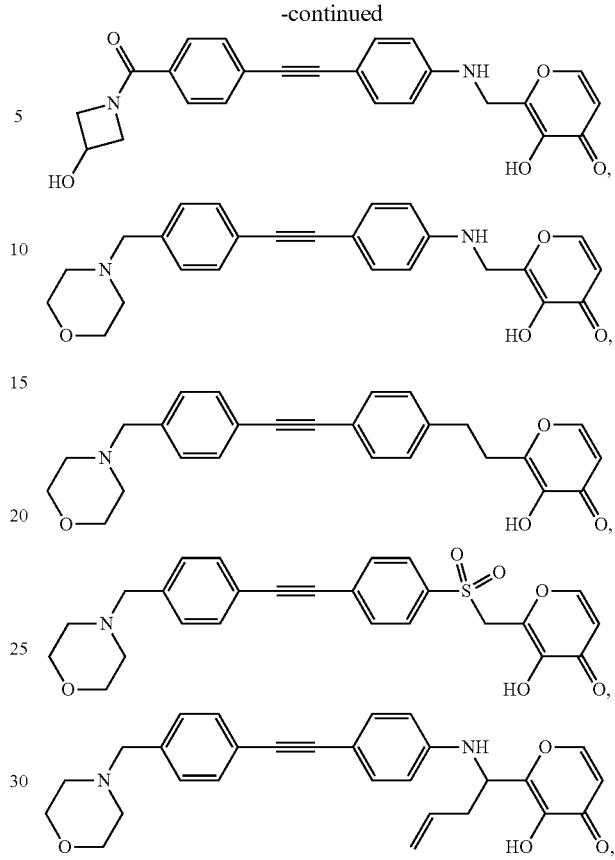
or a pharmaceutically acceptable salt thereof.
* * * * *

UNITED STATES PATENT AND TRADEMARK OFFICE
CERTIFICATE OF CORRECTION

PATENT NO.        : 10,611,747 B2
APPLICATION NO.   : 15/773976
DATED             : April 7, 2020
INVENTOR(S)       : Min Teng et al.

It is certified that error appears in the above-identified patent and that said Letters Patent is hereby corrected as shown below:

In the Claims

• Claim 1: Column 64, Line 4: "$L_2$ is a bivalent radical selected from $(C(R_4)CR_5))_n$-" should read -- $L_2$ is a bivalent radical selected from the group consisting of $(C(R_4)(R_5))_n$- --.

• Claim 1: Column 64, Line 5: "-$(C(R_4)(R_5))_n$-$C_{0-3}$ alkylene)-(CH-OR$^e$)-," should read -- -$(C(R_4)(R_5))_n$-$(C_{0-3}$ alkylene)-(CH-OR$^e$)-, --.

• Claim 1: Column 64, Line 13: "or –$(C(R_4)(R_5)_n$" should read -- and –$(C(R_4)(R_5)_n$ --.

• Claim 1: Column 64, Line 22: "on optionally substituted" should read -- an optionally substituted --.

• Claim 1: Column 64, Line 42: "selected from a bond" should read -- selected from the group consisting of a bond --.

• Claim 1: Column 64, Line 43: "-N(R$^e$)C(=O)-, or -($C_{1-4}$ alkylene)-;" should read -- -N(R$^e$)C(=O)-, and -($C_{1-4}$ alkylene)-; --.

• Claim 1: Column 64, Lines 45-46: "a bivalent radical selected from -($C_{6-14}$ arylene)- or -(5- to 14-membered heteroarylene)-" should read -- a bivalent radical selected from the group consisting of -($C_{6-14}$ arylene)- and -(5- to 14-membered heteroarylene)- --.

• Claim 2: Column 64, Lines 59-60: "$L_2$ is a bivalent radical is selected from -$(C(R_4)(R_5))_n$-$(C_{0-3}$ alkylene), or -$C(R_4)(R_5))_n$-$(C_{0-3}$ alkylene)-N(R$_5$)-" should read -- $L_2$ is a bivalent radical is selected from the group consisting of -$(C(R_4)(R_5))_n$-$(C_{0-3}$ alkylene), and –$(C(R_4)(R_5))_n$-$(C_{0-3}$ alkylene)-N(R$_5$)- --.

• Claim 2: Column 64, Lines 65-67: "$L_4$ is a bivalent radical selected from a bond, -C(=O)-, -(C(=O)O)-, -(C(=O)NR$^e$)-, -N(R$^e$)C(=O)-, or -($C_{1-4}$ alkylene)-;" should read -- $L_4$ is a bivalent radical Signed and Sealed this
Eighteenth Day of May, 2021

Drew Hirshfeld
*Performing the Functions and Duties of the
Under Secretary of Commerce for Intellectual Property and
Director of the United States Patent and Trademark Office* selected from the group consisting of a bond, -C(=O)-, -(C(=O)O)-, -(C(=O)NR$^e$)-, -N(R$^e$)C(=O)-, and -(C$_{1-4}$ alkylene)-; --.

• Claim 2: Column 65, Lines 2-3: "bivalent radical selected from -(C$_{6-14}$ arylene)- or -(5- to 14-membered heteroarylene)-;" should read -- bivalent radical selected from the group consisting of -(C$_{6-14}$ arylene)- and -(5- to 14-membered heteroarylene)-; --.

• Claim 3: Column 65, Line 14: "L$_2$ is a bivalent radical selected from -(C(R$_4$)(R$_5$))$_n$-" should read -- L$_2$ is a bivalent radical selected from the group consisting of -(C(R$_4$)(R$_5$))$_n$- --.

• Claim 3: Column 65, Line 16: "or -(C(R$_4$)(R$_5$))$_n$,-" should read -- and -(C(R$_4$)(R$_5$))$_n$- --.

• Claim 3: Column 65, Lines 19-21: "L$_4$ is a bivalent radical selected from a bond, -C(=O)-, -(C(=O)O)-, -(C(=O)NR$^e$)-, -N(R$^e$)C(=O)-, or -(C$_{1-4}$ alkylene)-;" should read -- L$_4$ is a bivalent radical selected from the group consisting of a bond, -C(=O)-, -(C(=O)O)-, -(C(=O)NR$^e$)-, -N(R$^e$)C(=O)-, and -(C$_{1-4}$ alkylene)-; --.

• Claim 3: Column 65, Lines 23-24: "bivalent radical selected from -(C$_6$ arylene)- or -(5- to 6-membered heteroarylene)-; and" should read -- bivalent radical selected from the group consisting of -(C$_6$ arylene)- and -(5- to 6-membered heteroarylene)-; and --.

• Claim 4: Column 65, Line 55: "L$_2$ is a bivalent radical selected from -(C(R$_4$)(R$_5$))$_n$-" should read -- L$_2$ is a bivalent radical selected from the group consisting of -(C(R$_4$)(R$_5$))$_n$- --.

• Claim 4: Column 65, Line 56: "(C(R$_4$)(R$_5$))$_n$-C$_{0-3}$ alkylene)" should read -- (C(R$_4$)(R$_5$))$_n$-(C$_{0-3}$ alkylene) --.

• Claim 4: Column 65, Line 61: "-(C(R$_4$)(R$_5$))$_n$-(C$_{0-3}$ alkylene)-O-, or" should read -- -(C(R$_4$)(R$_5$))$_n$-(C$_{0-3}$ alkylene)-O-, and --.

• Claim 4: Column 66, Line 2: "on optionally substituted" should read -- an optionally substituted --.

• Claim 4: Column 66, Line 20: "L$_3$ is a bivalent radical;" should read -- L$_3$ is a bivalent radical -(C$_{2-6}$ alkynylene)-; --.